(12) United States Patent
Charrier et al.

(10) Patent No.: US 8,969,356 B2
(45) Date of Patent: Mar. 3, 2015

(54) COMPOUNDS USEFUL AS INHIBITORS OF ATR KINASE

(75) Inventors: Jean-Damien Charrier, Wantage (GB); Steven John Durrant, Abingdon (GB); Ronald Marcellus Alphonsus Knegtel, Abingdon (GB); Joanne Pinder, Didcot (GB); Stephen Young, Oxford (GB); Philip Michael Reaper, Shillingford (GB)

(73) Assignee: Vertex Pharmaceuticals Incorporated, Boston, MA (US)

( * ) Notice: Subject to any disclaimer, the term of this patent is extended or adjusted under 35 U.S.C. 154(b) by 138 days.

(21) Appl. No.: 13/106,167

(22) Filed: May 12, 2011

(65) Prior Publication Data

US 2012/0178756 A1  Jul. 12, 2012

Related U.S. Application Data

(60) Provisional application No. 61/333,849, filed on May 12, 2010.

(51) Int. Cl.
| | |
|---|---|
| A61K 31/497 | (2006.01) |
| A61K 31/4965 | (2006.01) |
| C07D 241/20 | (2006.01) |
| C07D 401/06 | (2006.01) |
| C07D 403/06 | (2006.01) |
| C07D 409/06 | (2006.01) |
| C07D 401/04 | (2006.01) |
| C07D 401/12 | (2006.01) |
| C07D 405/12 | (2006.01) |

(52) U.S. Cl.
CPC ............ *C07D 241/20* (2013.01); *C07D 401/04* (2013.01); *C07D 401/06* (2013.01); *C07D 401/12* (2013.01); *C07D 403/06* (2013.01); *C07D 405/12* (2013.01); *C07D 409/06* (2013.01)
USPC ................. 514/255.05; 514/255.06; 544/336; 544/405

(58) Field of Classification Search
CPC .. C07D 241/20; C07D 401/06; C07D 403/06; C07D 409/06
USPC ................................................. 544/336, 405
See application file for complete search history.

(56) References Cited

U.S. PATENT DOCUMENTS

| | | | |
|---|---|---|---|
| 4,309,430 | A | 1/1982 | Bock et al. |
| 5,143,824 | A | 9/1992 | Yamakawa et al. |
| 6,660,753 | B2 | 12/2003 | Van Wagenen et al. |
| 6,858,600 | B2 | 2/2005 | Hamilton et al. |
| 6,992,087 | B2 | 1/2006 | Verhoest et al. |
| 7,041,672 | B2 | 5/2006 | Verhoest et al. |
| 7,199,123 | B2 | 4/2007 | Munchhof |
| 7,452,993 | B2 | 11/2008 | Arnold et al. |
| 7,622,583 | B2 | 11/2009 | Ungashe et al. |
| 7,626,021 | B2 | 12/2009 | Arnold et al. |
| 7,700,601 | B2 | 4/2010 | Chan et al. |
| 7,704,995 | B2 | 4/2010 | Buhr et al. |
| 7,829,558 | B2 | 11/2010 | Arnold et al. |
| 7,872,031 | B2 | 1/2011 | Lauffer et al. |
| 7,902,197 | B2 | 3/2011 | Elworthy et al. |
| 7,932,254 | B2 | 4/2011 | Dubois et al. |

(Continued)

FOREIGN PATENT DOCUMENTS

| | | |
|---|---|---|
| EP | 313724 A2 | 5/1989 |
| EP | 1217000 A1 | 6/2002 |

(Continued)

OTHER PUBLICATIONS

Nakamura et al. Bimodal chemiluminescence of 8-chlorostyryl-6-phenylethynylimidazopyrazinone: Large bathochromic shift caused by a styryl group at 8-position, 1998, Tetrahedron Letters, 39, 301-304.*

(Continued)

*Primary Examiner* — Brian McDowell
(74) *Attorney, Agent, or Firm* — Rory C. Stewart

(57) ABSTRACT

The present invention relates to pyrazine and pyridine compounds useful as inhibitors of ATR protein kinase. The invention also relates to pharmaceutically acceptable compositions comprising the compounds of this invention; methods of treating various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors.

The compounds of this invention have formula I:

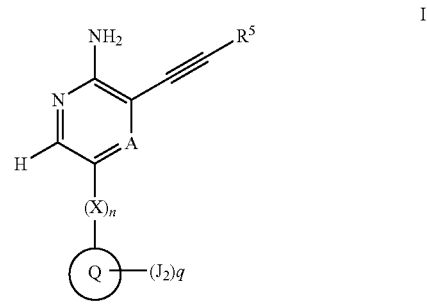

wherein the variables are as defined herein.

37 Claims, No Drawings

(56) References Cited

U.S. PATENT DOCUMENTS

| | | | |
|---|---|---|---|
| 7,939,531 B2 | 5/2011 | Bamberg et al. | |
| 7,981,893 B2 | 7/2011 | Mortensen et al. | |
| 8,063,032 B2 | 11/2011 | Chytil et al. | |
| 8,410,112 B2 | 4/2013 | Charrier et al. | |
| 2003/0008882 A1 | 1/2003 | Hamilton et al. | |
| 2003/0055085 A1 | 3/2003 | Wagenen et al. | |
| 2004/0034037 A1 | 2/2004 | Harbeson et al. | |
| 2004/0180905 A1 | 9/2004 | Munchhof | |
| 2006/0211709 A1 | 9/2006 | Buhr et al. | |
| 2007/0037794 A1 | 2/2007 | Ungashe et al. | |
| 2007/0254868 A1 | 11/2007 | Lauffer et al. | |
| 2007/0270420 A1 | 11/2007 | Harbeson et al. | |
| 2007/0287711 A1 | 12/2007 | Arnold et al. | |
| 2009/0005381 A1 | 1/2009 | Brown et al. | |
| 2009/0215724 A1 | 8/2009 | Dubois et al. | |
| 2009/0215750 A1 | 8/2009 | Bamberg et al. | |
| 2009/0215785 A1 | 8/2009 | Dubois et al. | |
| 2009/0215788 A1 | 8/2009 | Elworthy et al. | |
| 2009/0306087 A1 | 12/2009 | Ibrahim et al. | |
| 2010/0036118 A1 | 2/2010 | Arnold et al. | |
| 2010/0168138 A1 | 7/2010 | DeGoey et al. | |
| 2010/0204214 A1 | 8/2010 | Chytil et al. | |
| 2010/0222318 A1 | 9/2010 | Charrier et al. | |
| 2010/0233091 A1 | 9/2010 | Neumann et al. | |
| 2011/0015231 A1 | 1/2011 | Al-Abed et al. | |
| 2011/0288067 A1 | 11/2011 | Hendricks et al. | |
| 2011/0288097 A1 | 11/2011 | Hendricks et al. | |
| 2012/0027874 A1 | 2/2012 | Charrier et al. | |
| 2012/0035407 A1 | 2/2012 | Charrier et al. | |
| 2012/0035408 A1 | 2/2012 | Charrier et al. | |
| 2012/0040020 A1 | 2/2012 | Charrier et al. | |
| 2012/0046295 A1 | 2/2012 | Charrier et al. | |
| 2012/0065247 A1 | 3/2012 | Thompson et al. | |
| 2012/0115874 A1 | 5/2012 | Wang et al. | |
| 2012/0122884 A1 | 5/2012 | Charrier et al. | |
| 2012/0177748 A1 | 7/2012 | Charrier et al. | |
| 2012/0178756 A1 | 7/2012 | Charrier et al. | |
| 2013/0017273 A1 | 1/2013 | Everitt et al. | |
| 2013/0018035 A1 | 1/2013 | MacCormick et al. | |
| 2013/0034616 A1 | 2/2013 | Storck et al. | |
| 2013/0089624 A1 | 4/2013 | Charrier et al. | |
| 2013/0089625 A1 | 4/2013 | Charrier et al. | |
| 2013/0089626 A1 | 4/2013 | Pollard et al. | |
| 2013/0095193 A1 | 4/2013 | Charrier et al. | |
| 2013/0096139 A1 | 4/2013 | Charrier et al. | |
| 2013/0115310 A1 | 5/2013 | Charrier et al. | |
| 2013/0115311 A1 | 5/2013 | Charrier et al. | |
| 2013/0115312 A1 | 5/2013 | Charrier et al. | |
| 2013/0115313 A1 | 5/2013 | Charrier et al. | |
| 2013/0115314 A1 | 5/2013 | Charrier et al. | |
| 2013/0172273 A1 | 7/2013 | Aizpurua Iparraguirre et al. | |
| 2013/0184292 A1 | 7/2013 | Charrier et al. | |

FOREIGN PATENT DOCUMENTS

| | | | |
|---|---|---|---|
| EP | 2157090 A1 | 2/2010 | |
| WO | 9842701 A1 | 10/1998 | |
| WO | 0004014 A1 | 1/2000 | |
| WO | 0144206 A1 | 6/2001 | |
| WO | 0209648 A2 | 2/2002 | |
| WO | 03004472 A1 | 1/2003 | |
| WO | 03004475 A1 | 1/2003 | |
| WO | 03045924 A1 | 6/2003 | |
| WO | 03076422 A1 | 9/2003 | |
| WO | 03080610 A1 | 10/2003 | |
| WO | 03087057 A1 | 10/2003 | |
| WO | 03092686 A1 | 11/2003 | |
| WO | 03093297 A2 | 11/2003 | |
| WO | 03101968 A1 | 12/2003 | |
| WO | 2004000318 A2 | 12/2003 | |
| WO | 2004033431 A2 | 4/2004 | |
| WO | 2004055005 A1 | 7/2004 | |
| WO | 2004055006 A1 | 7/2004 | |
| WO | 2004084813 A2 | 10/2004 | |
| WO | 2004084824 A2 | 10/2004 | |
| WO | 2004085409 A2 | 10/2004 | |
| WO | 2004103279 A2 | 12/2004 | |
| WO | 2005028475 A2 | 3/2005 | |
| WO | 2005079802 A1 | 9/2005 | |
| WO | 2005123672 A2 | 12/2005 | |
| WO | 2006015124 A2 | 2/2006 | |
| WO | 2006053342 A2 | 5/2006 | |
| WO | 2006058074 A1 | 6/2006 | |
| WO | 2006067462 A1 | 6/2006 | |
| WO | 2006071548 A2 | 7/2006 | |
| WO | 2006075152 A1 | 7/2006 | |
| WO | 2006088837 A2 | 8/2006 | |
| WO | 2006114180 A1 | 11/2006 | |
| WO | 2006120573 A2 | 11/2006 | |
| WO | 2007015632 A1 | 2/2007 | |
| WO | 2007058850 A2 | 5/2007 | |
| WO | 2007063012 A1 | 6/2007 | |
| WO | 2007066805 A1 | 6/2007 | |
| WO | 2007076360 A1 | 7/2007 | |
| WO | 2007096151 A2 | 8/2007 | |
| WO | 2007096764 A2 | 8/2007 | |
| WO | 2007096765 A1 | 8/2007 | |
| WO | 2007102770 A1 | 9/2007 | |
| WO | 2007111904 A2 | 10/2007 | |
| WO | 2007126964 A2 | 12/2007 | |
| WO | 2007147874 A1 | 12/2007 | |
| WO | 2008037477 A1 | 4/2008 | |
| WO | 2008038010 A1 | 4/2008 | |
| WO | 2008040651 A1 | 4/2008 | |
| WO | 2008060907 A2 | 5/2008 | |
| WO | 2008071456 A2 | 6/2008 | |
| WO | 2008074997 A1 | 6/2008 | |
| WO | 2008079291 A2 | 7/2008 | |
| WO | 2008079903 A1 | 7/2008 | |
| WO | 2008079906 A1 | 7/2008 | |
| WO | 2008103277 A2 | 8/2008 | |
| WO | 2008106692 A1 | 9/2008 | |
| WO | 2008122375 A2 | 10/2008 | |
| WO | 2008124850 A1 | 10/2008 | |
| WO | 2008141065 A1 | 11/2008 | |
| WO | 2008144463 A1 | 11/2008 | |
| WO | 2008144464 A1 | 11/2008 | |
| WO | 2008157191 A2 | 12/2008 | |
| WO | 2009007390 A2 | 1/2009 | |
| WO | 2009012482 A2 | 1/2009 | |
| WO | 2009014637 A2 | 1/2009 | |
| WO | 2009016460 A2 | 2/2009 | |
| WO | 2009024825 A1 | 2/2009 | |
| WO | 2009037247 A1 | 3/2009 | |
| WO | 2009053737 A2 | 4/2009 | |
| WO | 2009106885 A1 | 9/2009 | |
| WO | 2010015803 A1 | 2/2010 | |
| WO | 2010048131 A1 | 4/2010 | |
| WO | 2010054398 A1 | 5/2010 | |
| WO | 2010063634 A1 | 6/2010 | |
| WO | 2010068483 A2 | 6/2010 | |
| WO | 2010071837 A1 | 6/2010 | |
| WO | 2011008830 A1 | 1/2011 | |
| WO | 2011117145 A2 | 9/2011 | |
| WO | 2011124998 A1 | 10/2011 | |
| WO | 2011130689 A1 | 10/2011 | |
| WO | 2011143399 A1 | 11/2011 | |
| WO | 2011143419 A1 | 11/2011 | |
| WO | 2011143422 A1 | 11/2011 | |
| WO | 2011143423 A2 | 11/2011 | |
| WO | 2011143425 A1 | 11/2011 | |
| WO | 2011143426 A1 | 11/2011 | |
| WO | 2011144584 A1 | 11/2011 | |
| WO | 2011144585 A1 | 11/2011 | |
| WO | 2012158785 A1 | 11/2012 | |
| WO | 2013049726 A2 | 4/2013 | |

OTHER PUBLICATIONS

Ammar, et al., "3-Ethoxycarbonylmethylenequinoxalin-2-one in Heterocyclic Synthesis. Part 1: Synthesis of New Substituted and Condensed Quinoxalines", Afinidad (2005), 62, pp. 151-160.

(56) References Cited

OTHER PUBLICATIONS

Charrier, et al, "Discovery of Potent and Selective Inhibitors of Ataxia Telangiesctasia Mutated and Rad3 Related (ATR) Protein Kinase as Potential Anticancer Agents" J. Med. Chem. (Apr. 14, 2011) 54(7), pp. 2320-2330.
El-Emary, "Synthesis and Biological Activity of Some New Pyrazolo[3,4-b]pyrazines", J. Chin. Chem. Soc. (2006), 53, pp. 391-401.
Fernandes, et al., "Synthesis and Biological Activity of Heterocyclic Derivatives derived from Ethyl-2-hydroxy-quinoxaline-3-carboxylate", J. Indian Chem. Soc. (1986), 63, pp. 427-429.
Hickson, et al., "Identification and Characterization of a Novel and Specific Inhibitor of the Ataxia-Telangiectasia Mutated Kinase ATM", Cancer Research (2004), 64, pp. 9152-9159.
Hilton, et al., "Identification and characterisation of 2-aminopyridine inhibitors of checkpoint kinase 2", Bioorg. Med. Chem., (2010) 18, pp. 707-718.
Klicnar, et al., "Studien in der Chinoxalinreihe III. Syntheses, Reaktionen and ir-spektren einiger 3-hydroxy-2-carboxymethylchinoxalin-derivative", Collection Czechoslav. Chem. Commun. (1965), 30, pp. 3092-3101.
Kim, et al., "Substrate Specificities and Identification of Putative Substrates of ATM Kinase Family Members", J. Biol. Chem. (1999) 274, pp. 37538-37543.
Kurasawa, et al., "Revised Structure for the Product from the Reaction of 3-Hydrazinocarbonylmethylene-2-oxo-1,2,3,4-tetrahydroquinoxaline with Nitrous Acid", Chem. Pharm. Bull. (1984), 32(10), pp. 4140-3.
Reaper, et al, "Selective Killing of ATM- or p53-deficient cancer cells through inhibition of ATR" Nature Communications (2011), 7, pp. 428-430.
Sarkaria, et al., "Inhibition of ATM and ATR Kinase Activities by the Radiosensitizing Agent, Caffeine", Cancer Research (1999) 59, pp. 4375-4382.
Sugimoto, et al., "Imidazopteridines. I. Synthesis of Imidazo[1,2-c]pteridine and Its Alkyl Derivatives", Bull. Chem. Soc. Japan (1977) 50(10), pp. 2744-2747.
Ward and Chen, "Histone H2AX Is Phosphorylated in an ATR-dependent Manner in Response to Replicational Stress", J. Biol. Chem. (2001), 51, pp. 47759-47762.
Abdel-Magid, A., "Inhibitors of Atr Kinase for Treatment on Cancer", ACS Medicinal Chemistry Letters, 4(8), (2013), pp. 688-689.
Charrier, J.D., "Discovery of potent and selective inhibitors of Ataxia Telangiectasia mutated and Rad3 related (Atr) protein kinase as potential anticancer agents", Presentation, ACS Denver 2011, Aug. 28, 2011.
Charrier, J.D., et al., "Discovery of Potent and Selective Inhibitors of ATR (Ataxia Telangiectasia Mutated and Rad3 Related) as Potential Anticancer Agents", Supplementary Information, Apr. 14, 2011.
Clark, B.A.J., et al., "Mass Spectrometry of Pyrroloa2,3-Btipyrazines and Pyrazinoä2,3-Mindole", Organic Mass Spectrometry, 12(7), (1997), pp. 421-423.
Curtin, N.J., "Inhibiting the DNA damage response as a therapeutic manoeuvre in cancer", British Journal of Pharmacology, (2013), pp. 1-52.
Finlay, M.R., et al., "Modulation of DNA repair by pharmacological inhibitors of the PIKK protein kinase family", Bioorg. Med. Chem. Letters, 22(17) (2012), pp. 5352-5359.
Fokas, E., et al., "Targeting ATR in vivo using the novel inhibitor VE-822 results in selective sensitization of pancreatic tumors to radiation", Cell Death and Disease, 3 (2012), pp. 1-5 (DOI: 10.1038/cddis.2012.181).
Fokas, E., et al., "Targeting ATR in DNA damage response and cancer therapeutics", Cancer Treatment Reviews (2013), (DOI: 10.1016/j.ctrv.2013.03.002).
Gentili, F., et al., "Alpha2-Adrenoreceptors Profile Modulation. 4. From Antagonist to Agonist Behavior", J. Med. Chem., 51(14), Jun. 25, 2008), pp. 4289-4299.
Hall-Jackson, C.A., et al., "ATR is a caffeine-sensitive, DNA-activated protein kinase with a substrate specificity distinct from DNA-PK", Oncogene, 18(48) (1999), pp. 6707-6713.
Jiang, B., et al., "Synthesis and cytotoxicity evaluation of novel indolylpyrimidiens and indolylpyrazines as potential antitummor agents", Bioorganic & Medicinal Chemistry, 9 (2001), pp. 1149-1154.
Luo, et al., "Molecular dynamics-based self-organizing molecular field analysis on 3-amino-6-arypyrazines as the ataxia telangiectasia mutated and Rad3 related (ATR) protein kinase inhibitors", Medicinal Chemistry Research, (2013), pp. 1-12.
McKenna, G., et al., "Evaluation of the first potent and highly selective inhibitor of ATR kinase: an approach to selectively sensitize cancer cells to ionizing radiation and hypoxia", Abstract, Mar. 31, 2012.
McKenna, G., et al., "Evaluation of the first potent and highly selective inhibitor of ATR inhibitor, VE-821: an approach to selectively sensitize cancer cells to ionizing radiation and hypoxia", Poster, Mar. 31, 2012.
Middleton, F. and Curtin, N.J., "ATR as a Therapeutic Target", Advances in DNA Repair in Cancer, Northern Institute for Cancer Research, Newcastle University (2013), pp. 211-228.
Nakamura, H., et al., "Bimodal chemiluminescence of 8-chlorostyryl-6-phenylethynylimidazopyrazinone: Large bathochromic shift caused by a styryl group at 8-position", Tetrahedron Letters, 39, (1998), pp. 301-304.
Pires, I.M., et al., "Targeting radiation-resisitant hypoxic tumour cells thorugh ATR inhibition", British Journal of Cancer, Jun. 19, 2012, pp. 1-9.
Pollard, J., "Inhibition of the DNA Damage Response Kinase, ATR, as a Promising Anti-Cancer Approach", Presentation, Mar. 8, 2012.
Qi, et al., "Chemi- and bio-luminescence of coelenterazine analogs with phenyl homologs at the C-2 position", Journal of the Chemical Society, Perkin Transactions 1: Organic and Bio-Organic Chemistry,13, (1992), pp. 1607-1611.
Reaper, P.M., et al., "Selective Killing of ATM- or p53-deficient cancer cells through inhibition of ATR", Supplementary Information, Apr. 13, 2011.
Reaper, P.M., et al., "Selective Killing of ATM- or p53-deficient cancer cells through inhibition of ATR", Presentation, Nov. 21, 2011.
Reaper, P.M., et al., "Selective Killing of ATM- or p53-deficient cancer cells through inhibition of ATR", Presentation, Nov. 29, 2011.
Reaper, P.M., et al., "Evaluation of a potent and highly selective inhibitor of ATR kinase: an approach to selectively sensitize cancer cells to genotoxic drugs", Abstract, Mar. 31, 2012.
Reaper, P.M., et al., "Evaluation of a Potent and Highly Selective Inhibitor of ATR Kinase: An Approach to Selectively Sensitize Cancer Cells to Genotoxic Drugs", Poster, Mar. 31, 2012.
Katritzky, A.R., et al., "Efficient synthesis of 3,5-functionalized isoxazoles and isoxazolines via 1,3-dipolar cycloaddition reactions of 1-propargyl- and 1-allylbenzotriazoles", J. Heterocyclic Chem., 37(6), (2000), pp. 1505-1510.
Kumpaty, H.J., et al., "Synthesis of N-Methyl Secondary Amines", Synth. Commun., 33(8), (2003), pp. 1411-1416.
March, J., March's Advanced Organic Chemistry, 2007, John Wiley and Sons, Chapter 16.
Saito, R., et al., "Synthesis and in vitro evaluation of botryllazine B analogues as a new class of inhibitor against human aldose reductase", Tetrahedron, 65 (2009), pp. 3019-3026.
Wuts, P.G.M., Greene's Protective Groups in Organic Synthesis, 4th Edition, 2006, John Wiley and Sons, Chapter 4.
Wuts, P.G.M., Greene's Protective Groups in Organic Synthesis, 4th Edition, 2006, John Wiley and Sons, Chapter 7.
Non-Final Office Action dated Sep. 28, 2013 in U.S. Appl. No. 13/631,727.
Non-Final Office Action dated Sep. 28, 2013 in U.S. Appl. No. 13/631,732.

* cited by examiner

COMPOUNDS USEFUL AS INHIBITORS OF ATR KINASE

CROSS REFERENCE TO RELATED APPLICATIONS

This present application claims the benefit, under 35 U.S.C. §119, to U.S. Provisional Application No. 61/333,849, filed on May 12, 2010, the entire contents of which are incorporated herein by reference.

SEQUENCE LISTING

The instant application contains a Sequence Listing in .txt format which has been submitted via EFS-Web and is hereby incorporated by reference in its entirety. The Sequence Listing, created on Sep. 28, 2014, is named VPI10-134US.txt and is 744 bytes in size.

BACKGROUND OF THE INVENTION

ATR ("ATM and Rad3 related") kinase is a protein kinase involved in cellular responses to DNA damage. ATR kinase acts with ATM ("ataxia telangiectasia mutated") kinase and many other proteins to regulate a cell's response to DNA damage, commonly referred to as the DNA Damage Response ("DDR"). The DDR stimulates DNA repair, promotes survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

Healthy cells can rely on a host of different proteins for DNA repair including the DDR kinase ATR. In some cases these proteins can compensate for one another by activating functionally redundant DNA repair processes. On the contrary, many cancer cells harbour defects in some of their DNA repair processes, such as ATM signaling, and therefore display a greater reliance on their remaining intact DNA repair proteins which include ATR.

In addition, many cancer cells express activated oncogenes or lack key tumour suppressors, and this can make these cancer cells prone to dysregulated phases of DNA replication which in turn cause DNA damage. ATR has been implicated as a critical component of the DDR in response to disrupted DNA replication. As a result, these cancer cells are more dependent on ATR activity for survival than healthy cells. Accordingly, ATR inhibitors may be useful for cancer treatment, either used alone or in combination with DNA damaging agents, because they shut down a DNA repair mechanism that is more important for cellular survival in many cancer cells than in healthy normal cells.

In fact, disruption of ATR function (e.g. by gene deletion) has been shown to promote cancer cell death both in the absence and presence of DNA damaging agents. This suggests that ATR inhibitors may be effective both as single agents and as potent sensitizers to radiotherapy or genotoxic chemotherapy.

ATR peptide can be expressed and isolated using a variety of methods known in the literature (see e.g., Ünsal-Kaçmaz et al, *PNAS* 99: 10, pp 6673-6678, May 14, 2002; see also Kumagai et al. *Cell* 124, pp 943-955, Mar. 10, 2006; Unsal-Kacmaz et al. *Molecular and Cellular Biology*, February 2004, p 1292-1300; and Hall-Jackson et al. *Oncogene* 1999, 18, 6707-6713).

For all of these reasons, there is a need for the development of potent and selective ATR inhibitors for the treatment of cancer, either as single agents or as combination therapies with radiotherapy or genotoxic chemotherapy.

SUMMARY OF THE INVENTION

The present invention relates to pyrazine and pyridine compounds useful as inhibitors of ATR protein kinase. The invention also relates to pharmaceutically acceptable compositions comprising the compounds of this invention; methods of treating various diseases, disorders, and conditions using the compounds of this invention; processes for preparing the compounds of this invention; intermediates for the preparation of the compounds of this invention; and methods of using the compounds in in vitro applications, such as the study of kinases in biological and pathological phenomena; the study of intracellular signal transduction pathways mediated by such kinases; and the comparative evaluation of new kinase inhibitors. These compounds have an unexpected ability to treat cancer as single agents. These compounds also show surprising synergy with other cancer agents, such as cisplatin, in combination therapies.

DETAILED DESCRIPTION OF THE INVENTION

One aspect of this invention provides a compound of Formula I

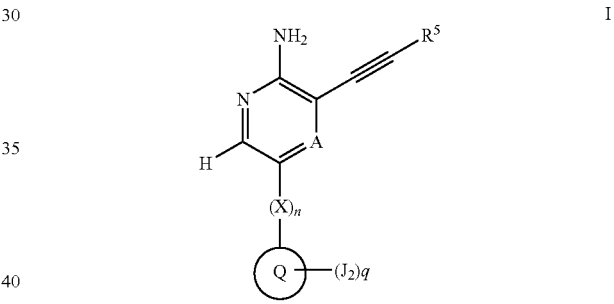

or a pharmaceutically acceptable salt thereof, wherein
A is CH or N;
X is O, NR", S, C(O)NR", NR"CO, C(O)O, —C(R")=C(R")—, or —C≡C—;
n is 0 or 1;
Q is a 5-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur;
$R^5$ is H, $C_{1-6}$aliphatic, a 3-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur; $R^5$ is optionally substituted with 1-5 $J^5$ groups;
$J^5$ is halo, oxo, CN, $NO_2$, X'—R, or —$(X^1)_p$-$Q^4$;
$X^1$ is $C_{1-10}$aliphatic; wherein 1-3 methylene units of said $C_{1-10}$aliphatic are optionally replaced with —NR'—, —O—, —S—, C(O), $S(O)_2$, or S(O); wherein $X^1$ is optionally and independently substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, CO($C_{1-4}$ aliphatic), $CO_2H$, $CO_2(C_{1-4}$aliphatic), $C(O)NH_2$, $C(O)NH$ $(C_{1-4}$aliphatic), $C(O)N(C_{1-4}$aliphatic)$_2$, $SO(C_{1-4}$aliphatic), $SO_2(C_{1-4}$aliphatic), $SO_2NH(C_{1-4}$aliphatic), $SO_2N(C_{1-4}$aliphatic)$_2$, $NHC(O)(C_{1-4}$aliphatic), $N(C_{1-4}$aliphatic)$C(O)$ $(C_{1-4}$aliphatic), $NHSO_2(C_{1-4}$aliphatic), or $N(C_{1-4}$aliphatic)$SO_2(C_{1-4}$aliphatic), wherein said $C_{1-4}$aliphatic is optionally substituted with 1-3 occurrences of halo;

$Q^4$ is a 3-8 membered saturated, partially unsaturated, or fully unsaturated monocyclic ring having 0-4 heteroatoms independently selected from nitrogen, oxygen, or sulfur, or a 8-10 membered saturated, partially unsaturated, or unsaturated bicyclic ring having 0-6 heteroatoms independently selected from nitrogen, oxygen, or sulfur; each $Q^4$ is optionally substituted with 1-5 $J^{Q4}$;

$J^{Q4}$ is halo, CN, or $C_{1-4}$alkyl wherein up to 2 methylene units are optionally replaced with O, NR*, S, C(O), S(O), or $S(O)_2$;

R is H or $C_{1-4}$alkyl wherein said $C_{1-4}$alkyl is optionally substituted with 1-4 halo;

$J^2$ is halo, CN, or V, or $(V)_t$—$R^1$;

V is a $C_{1-10}$aliphatic group wherein up to 2 methylene units are optionally replaced with O, NR", C(O), S, S(O), or $S(O)_2$; wherein said $C_{1-10}$aliphatic group is optionally substituted with 1-3 halo or CN;

$R^1$ is 3-7 membered aromatic or nonaromatic monocyclic ring having 0-3 heteroatoms selected from oxygen, nitrogen, or sulfur; wherein said monocyclic ring is optionally substituted with 1-3 occurrences of $C_{1-6}$aliphatic wherein up to 3 methylene units can be replaced with NR', O, S, CO, halo, CN, or a $C_{3-6}$cycloalkyl;

q is 0, 1, or 2;

p is 0 or 1;

t is 0 or 1;

R', R", and R* are each independently H or $C_1$-$C_4$ alkyl.

One aspect of this invention provides a compound of Formula I

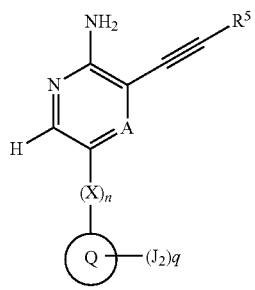

I or a pharmaceutically acceptable salt thereof, wherein

A is CH or N;

X is O, NR", S, C(O)NR", NR"CO, C(O)O, —C(R")=C(R")—, —C≡C—;

n is 0 or 1;

Q is a 5-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur;

$R^5$ is H, $C_{1-6}$aliphatic, a 3-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur; $R^5$ is optionally substituted with 1-5 $J^5$ groups;

$J^5$ is halo, oxo, CN, $NO_2$, $X^1$—R, or —$(X^1)_p$-$Q^4$;

$X^1$ is $C_{1-10}$aliphatic; wherein 1-3 methylene units of said $C_{1-10}$aliphatic are optionally replaced with —NR'—, —O—, —S—, C(O), $S(O)_2$, or S(O); wherein $X^1$ is optionally and independently substituted with 1-4 occurrences of $NH_2$, $NH(C_{1-4}$aliphatic), $N(C_{1-4}$aliphatic)$_2$, halogen, $C_{1-4}$aliphatic, OH, $O(C_{1-4}$aliphatic), $NO_2$, CN, $CO(C_{1-4}$aliphatic), $CO_2H$, $CO_2(C_{1-4}$aliphatic), $C(O)NH_2$, $C(O)NH(C_{1-4}$aliphatic), $C(O)N(C_{1-4}$aliphatic)$_2$, $SO(C_{1-4}$aliphatic), $SO_2(C_{1-4}$aliphatic), $SO_2NH(C_{1-4}$aliphatic), $SO_2N(C_{1-4}$aliphatic)$_2$, $NHC(O)(C_{1-4}$aliphatic), $N(C_{1-4}$aliphatic)$C(O)$ $(C_{1-4}$aliphatic), $NHSO_2(C_{1-4}$aliphatic), or $N(C_{1-4}$aliphatic)$SO_2(C_{1-4}$aliphatic), wherein said $C_{1-4}$aliphatic is optionally substituted with 1-3 occurrences of halo;

$Q^4$ is a 3-8 membered saturated, partially unsaturated, or fully unsaturated monocyclic ring having 0-4 heteroatoms independently selected from nitrogen, oxygen, or sulfur, or a 8-10 membered saturated or unsaturated bicyclic ring having 0-6 heteroatoms independently selected from nitrogen, oxygen, or sulfur; each $Q^4$ is optionally substituted with 1-5 $J^{Q4}$;

$J^{Q4}$ is halo, CN, or $C_{1-4}$alkyl wherein up to 2 methylene units are optionally replaced with O, NR*, S, C(O), S(O), or $S(O)_2$;

R is H or $C_{1-4}$alkyl wherein said $C_{1-4}$alkyl is optionally substituted with 1-4 halo;

$J^2$ is halo, CN, or V, or $(V)_t$—$R^1$;

V is a $C_{1-10}$aliphatic group wherein up to 2 methylene units are optionally replaced with O, NR", C(O), S, S(O), or $S(O)_2$; wherein said $C_{1-10}$aliphatic group is optionally substituted with 1-3 halo or CN;

$R^1$ is 3-7 membered aromatic or nonaromatic monocyclic ring having 0-3 heteroatoms selected from oxygen, nitrogen, or sulfur; wherein said monocyclic ring is optionally substituted with 1-3 occurrences of $C_{1-6}$aliphatic wherein up to 3 methylene units can be replaced with NR', O, S, CO, halo, CN, or a $C_{3-6}$cycloalkyl;

q is 0, 1, or 2;

p is 0 or 1;

t is 0 or 1;

R', R", and R* are each independently H or $C_1$-$C_4$ alkyl.

In some embodiments A is N. In some embodiments, $R^5$ is optionally substituted $C_{1-6}$aliphatic, 3-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur.

In one embodiment, n is 0. In some embodiments, Q is tetrahydropyrid-4-yl or pyri-2-on-5-yl. In other embodiments, Q is an aromatic ring. In some embodiments, Q is a 5-6 membered ring. In other embodiments, Q is phenyl. In some embodiments, q is 1. In other embodiments, q is 1 and Ring Q is a 6-membered aromatic ring substituted in the para position with $J_2$.

In some embodiments, $J_2$ is V. In certain embodiments, V is a $C_{1-6}$aliphatic group wherein one methylene unit is optionally replaced with $S(O)_2$. In some embodiments, V is —$S(O)_2(C_{1-4}$alkyl). In other embodiments, V is $S(O)_2CH(CH_3)_2$. In some embodiments, $J_2$ is CN and substituted in the ortho position.

In other embodiments, $J_2$ is —$(V)_t$—$R^1$. In some embodiments, V is —$S(O)_2$. In other embodiments, R' is a 4-6 membered nonaromatic monocyclic ring having 1 heteroatom selected from oxygen, nitrogen, or sulfur. In some embodiments, the heteroatom is nitrogen or oxygen. In other embodiments, $J_2$ is —$S(O)_2$-piperidine or —$S(O)_2$-tetrahydropyran. In yet other embodiments, $J_2$ is $S(O)_2(C_{1-6}$alkyl). In some embodiments, $J_2$ is $S(O)_2CH(CH_3)_2$. In another embodiment, $R^5$ is a 3-7 membered monocyclic fully saturated, partially unsaturated, or aromatic ring containing 0-4 heteroatoms independently selected from nitrogen, oxygen, or sulfur. In some embodiments, $R^5$ is an aromatic ring containing 1-2 heteroatoms selected from oxygen, nitrogen, or sulfur. In some embodiments, $R^5$ is phenyl, naphthyl, imidazolyl, indazolyl, pyridyl, or thienyl. In certain embodiments, $R^5$ is phenyl, naphthyl, thienyl, or pyridinyl. In some embodiments, $R^5$ is phenyl. In some embodiments, $R^5$ is optionally substituted phenyl. In some embodiments, $R^5$ is substituted in the meta position with $J^5$. In some embodiments, $R^5$ is substituted with one occurrence of $J^5$. In some embodiments, $J^5$ is in the meta position of $R^5$.

In another embodiment $R^5$ is H, $C_{1-6}$alkyl, phenyl, naphthyl, cyclopropyl, cyclohexyl, imidazolyl, indazolyl, pyridyl, thienyl, or $CH_2Ph$, wherein said $C_{1-6}$alkyl is optionally substituted with OH or methyl.

In another embodiment, $J^5$ is halo, oxo, CN, $X^1$—R, or —$(X^1)_p$-$Q^4$; wherein
  $X^1$ is $C_{1-10}$aliphatic; wherein 1-2 methylene units of said $C_{1-10}$aliphatic are optionally replaced with C(O), —NR'— or —O—;
  $Q^4$ is a 3-8 membered saturated, partially unsaturated, or fully unsaturated monocyclic ring having 0-4 heteroatoms independently selected from nitrogen, oxygen, or sulfur; each $Q^4$ is optionally substituted with 1-5 $J^{Q4}$;
  $J^{Q4}$ is halo, CN, or $C_{1-4}$alkyl; and
  R is H or $C_{1-4}$alkyl wherein said $C_{1-4}$alkyl is optionally substituted with 1-4 halo.

In some embodiments, $J^5$ is halo, CN, $C_{1-4}$alkyl, OH, O($C_{1-4}$alkyl), —NH($C_{1-4}$alkyl), —O—($C_{1-4}$alkyl)-NH($C_{1-4}$alkyl), —O—($C_{1-4}$alkyl)-N($C_{1-4}$alkyl)$_2$, —O—($C_{1-4}$alkyl)-NH$_2$, —($C_{1-4}$alkyl)-NH($C_{1-4}$alkyl), —($C_{1-4}$alkyl)-NH$_2$, —($C_{1-4}$alkyl)-N($C_{1-4}$alkyl)$_2$, or —O—($C_{1-4}$alkyl)-(morpholinyl). In other embodiments, $J^5$ is halo, $C_{1-4}$alkyl, OH, NH$_2$, phenyl, —NH($C_{1-4}$alkyl), or O($C_{1-4}$alkyl). In yet other embodiments, $J^5$ is OH or NH$_2$. According to another embodiment, $R^5$ is phenyl and $J^5$ is fluoro, chloro, methyl, cyano, OH, OCH$_3$, —O(CH$_2$)$_2$N(CH$_3$)$_2$, —O(CH$_2$)$_3$N(CH$_3$)$_2$, CH$_2$NH(CH$_3$), NH$_2$, CH(CH$_3$)OH, NHC(O)CH$_3$, NHC(O)CH$_2$NH$_2$, —C(O)NH$_2$, CH$_2$OH, CH(OH)CH$_2$NH$_2$, piperazinyl, or —O—(CH$_2$)$_2$-(morpholinyl). In some embodiments, $J^5$ is substituted in the meta position of $R^5$.

In some embodiments, $Q^4$ is a 3-8 membered saturated or unsaturated monocyclic ring. In some embodiments, $Q^4$ is cyclopropyl or morpholinyl.

In some embodiments, $R^5$ is a 3-6 membered cycloalkyl ring.

Another embodiments provides a compound of Formula Ia:

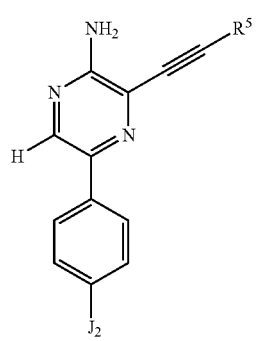

Ia wherein
  $R^5$ is an aromatic ring optionally containing 1-3 heteroatoms selected from nitrogen or sulfur;

$J_2$ is V or —$(V)_t$—$R^1$;
V is a $C_{1-6}$aliphatic group wherein one methylene unit is optionally replaced with $S(O)_2$;
$R^1$ is a 5-6 membered nonaromatic monocyclic ring having 1 heteroatom selected from oxygen, nitrogen, or sulfur;
t is 0 or 1.

According to another embodiment, $R^5$ is optionally substituted phenyl and $J^2$ is $S(O)_2CH(CH_3)_2$. In some embodiments, $R^5$ is substituted in the meta position with $J^5$.

Another embodiment provides a compound from the following Table:

TABLE 1

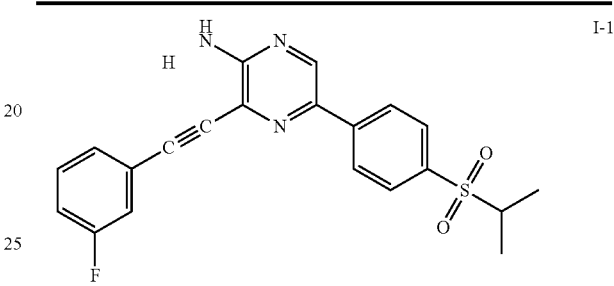

I-1

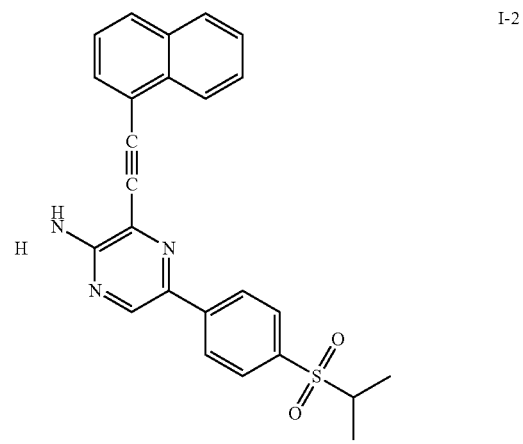

I-2

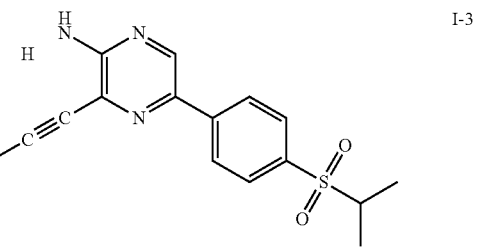

I-3

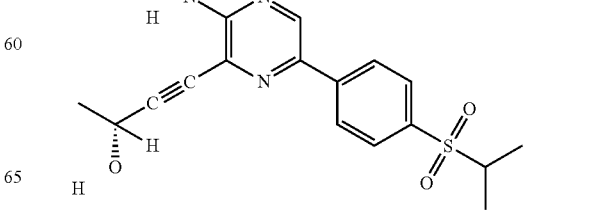

I-4

TABLE 1-continued
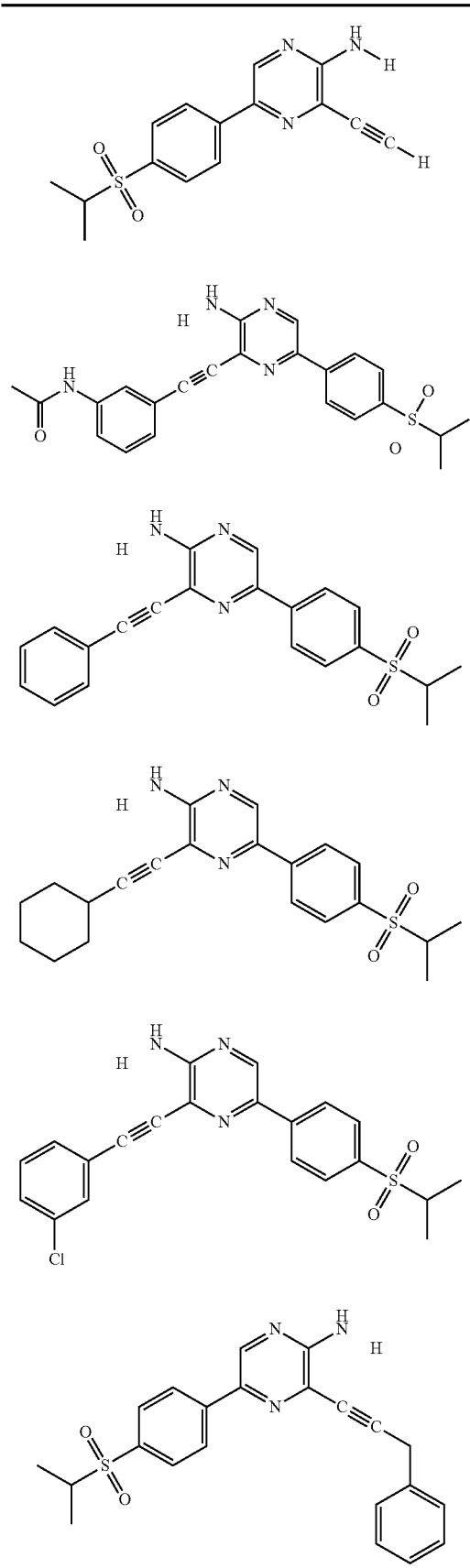
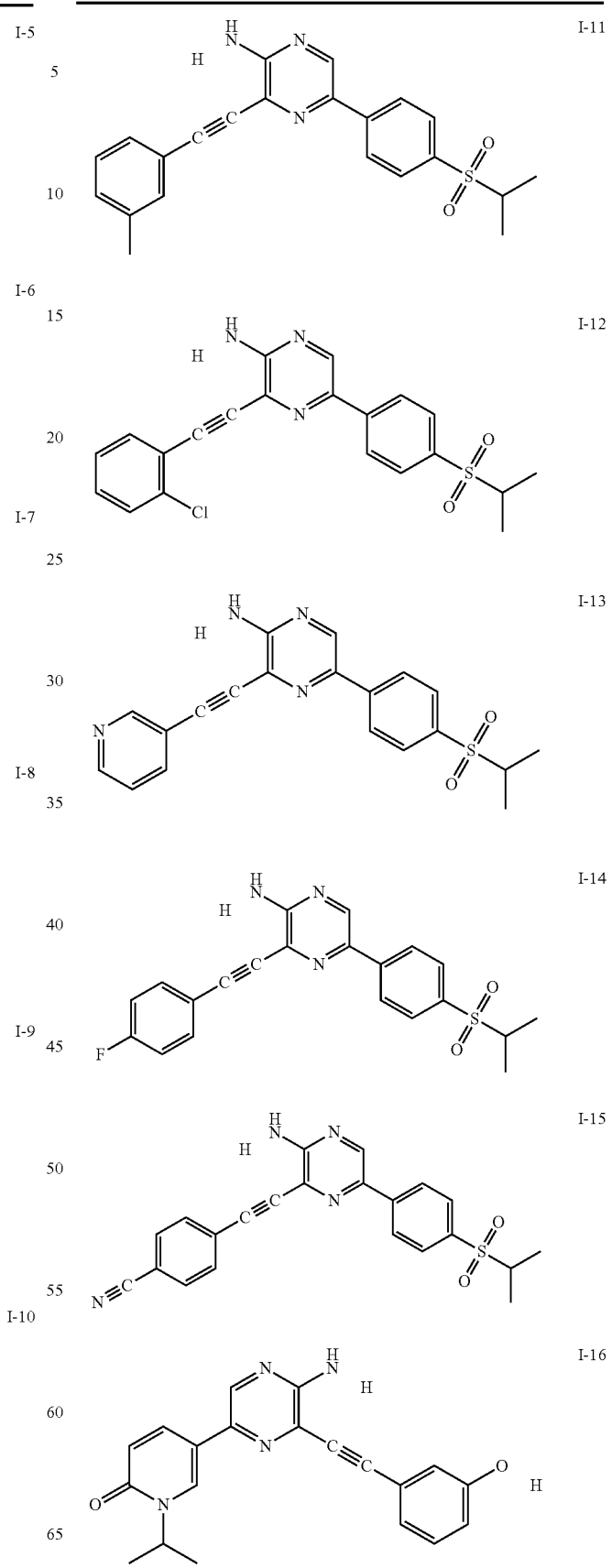

TABLE 1-continued
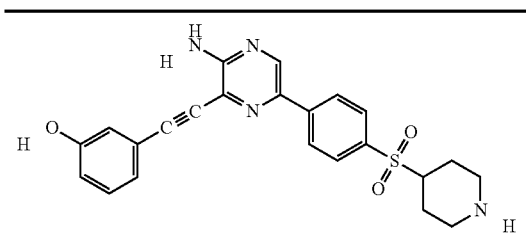 I-17
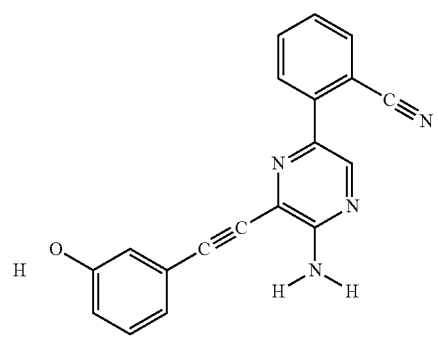 I-18
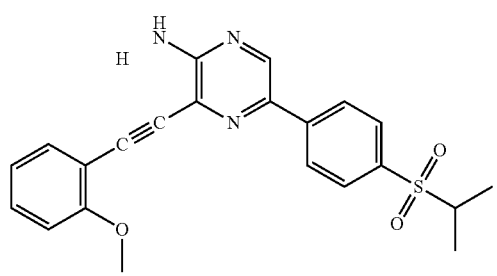 I-19
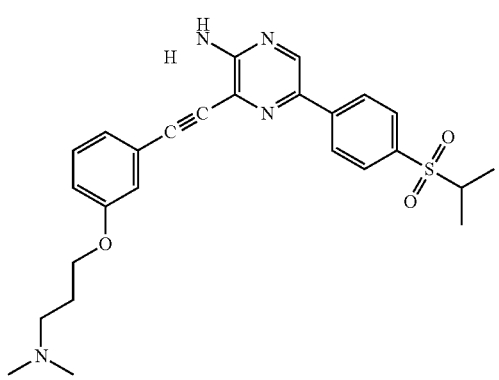 I-20
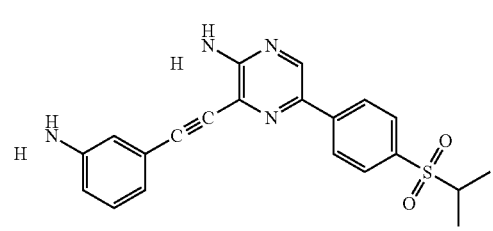 I-21
TABLE 1-continued
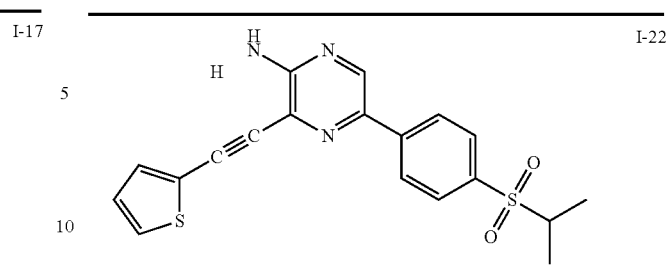 I-22
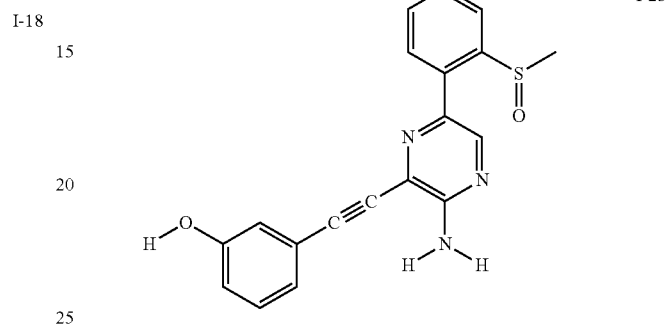 I-23
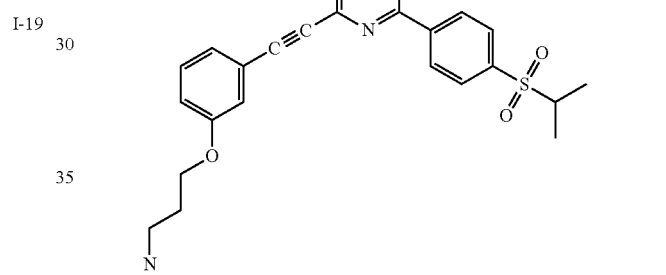 I-24
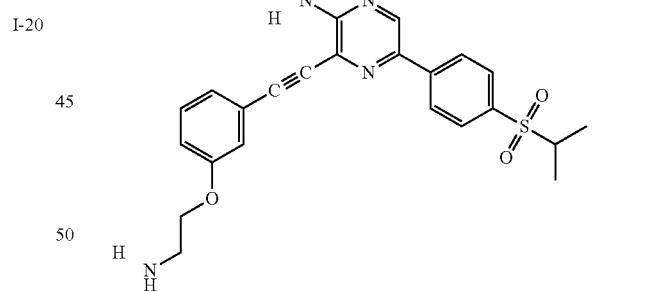 I-25
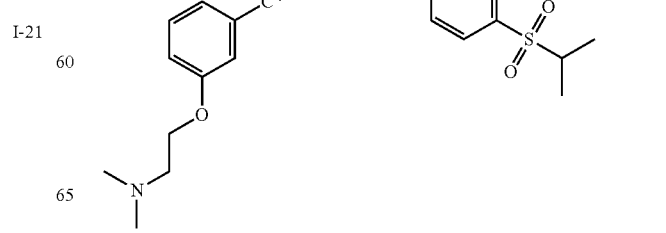 I-26

TABLE 1-continued
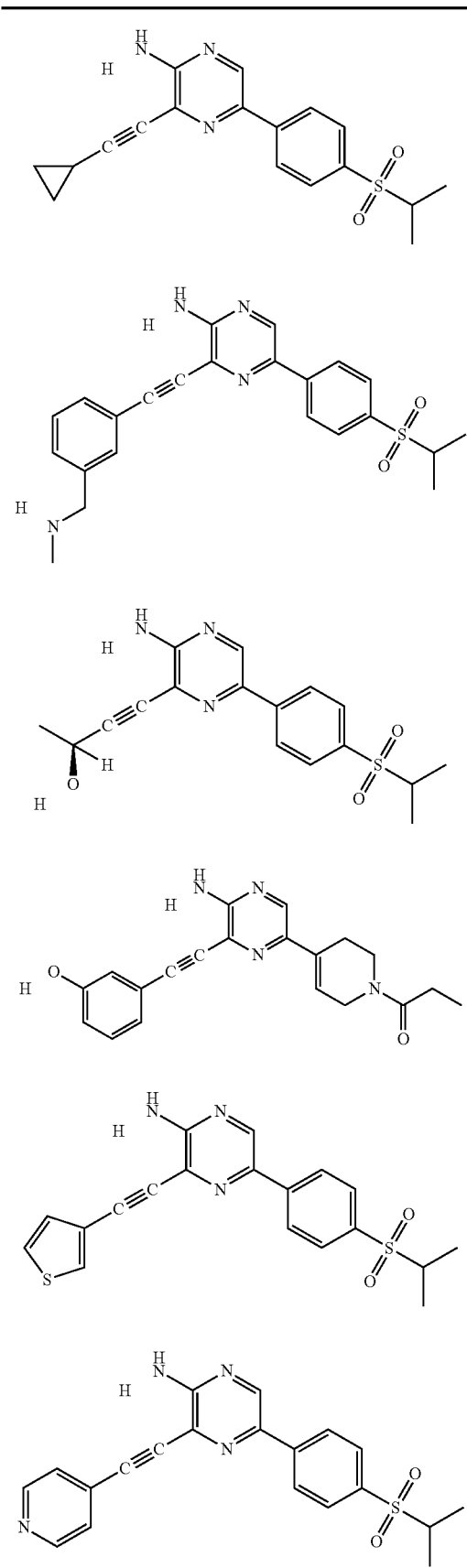
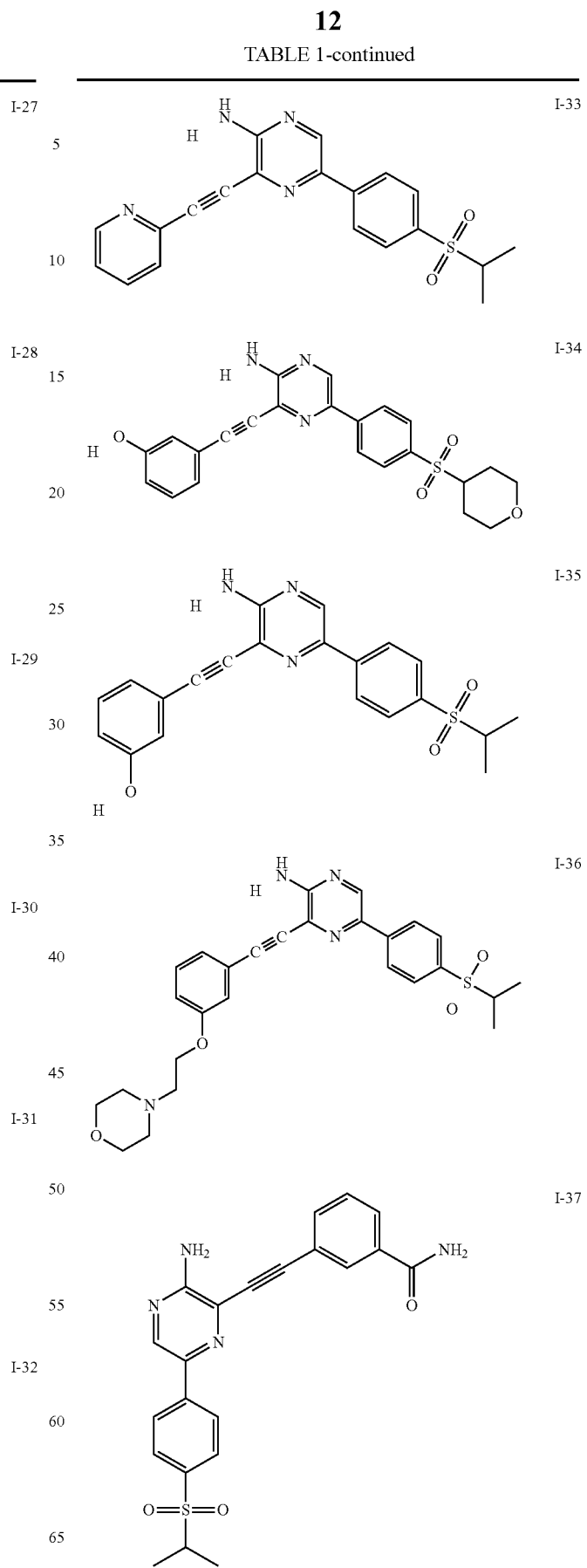

TABLE 1-continued
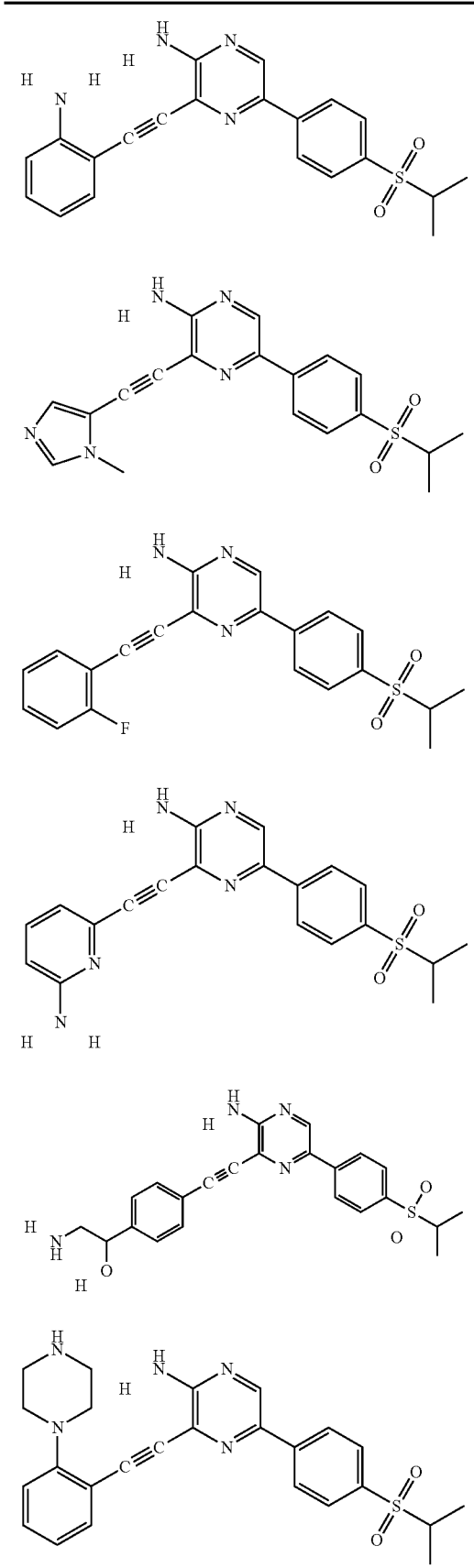
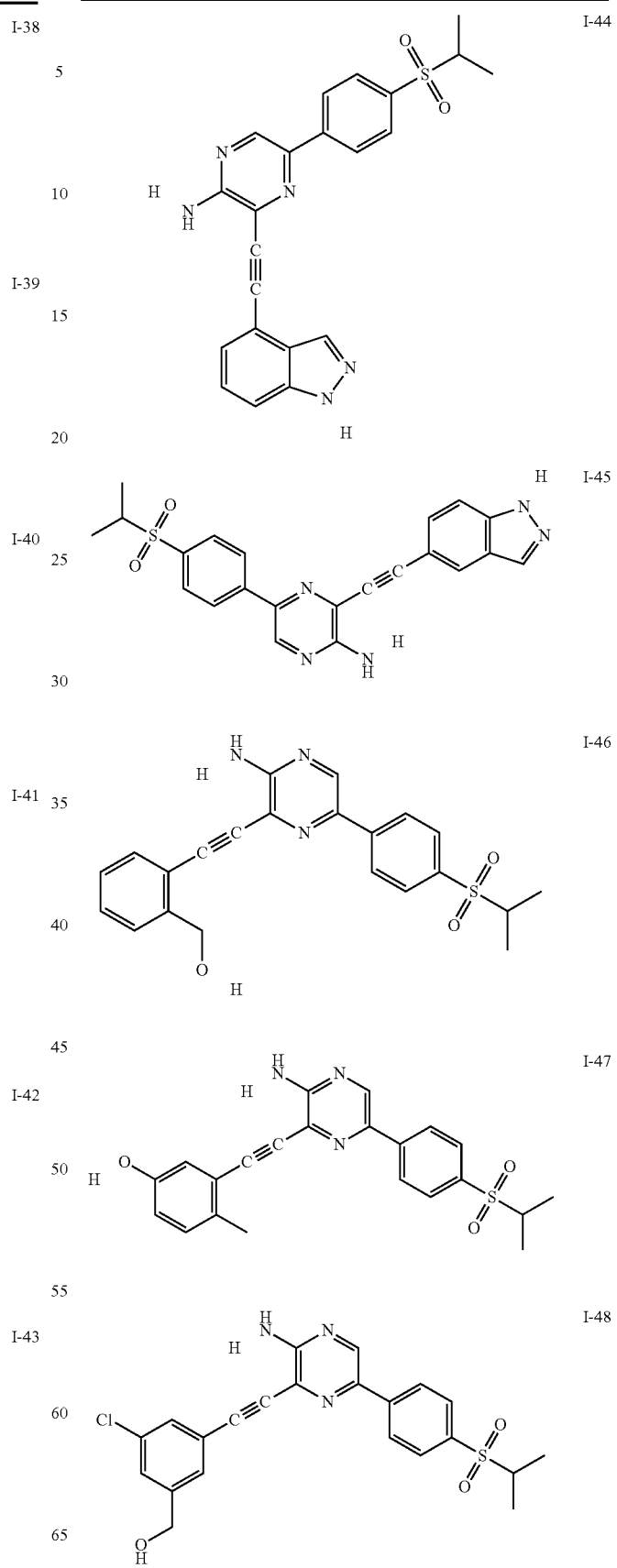

TABLE 1-continued

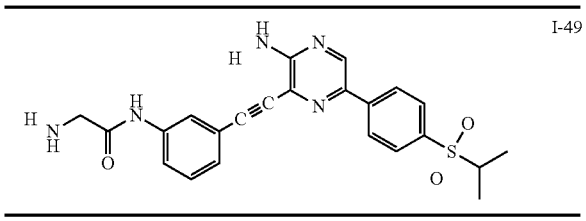

I-49

In some embodiments, the variables are as depicted in the compounds of the disclosure including compounds in the tables above.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, J$^1$ can be bonded to any position on the pyridyl ring. For bicyclic rings, a bond drawn through both rings indicates that the substituent can be bonded from any position of the bicyclic ring. In example ii below, for instance, J$^1$ can be bonded to the 5-membered ring (on the nitrogen atom, for instance), and to the 6-membered ring.

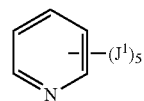

i

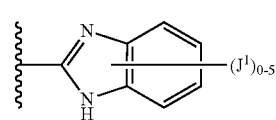

ii

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —CH$_2$-cyclopropyl, CH$_2$CH$_2$CH(CH$_3$)-cyclohexyl.

The term "cycloaliphatic" (or "carbocycle" or "carbocyclyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

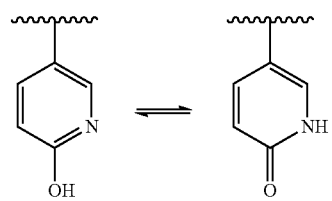 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH₃)₂], a nitrogen atom (e.g. NR) replacing the first recited "methylene unit" would result in dimethylamine [—N(CH₃)₂]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a $C_3$ aliphatic can be optionally replaced by 2 nitrogen atoms to form —C—N=N. The optional replacements can also completely replace all of the carbon atoms in a chain. For example, a $C_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH₂CH₂CH₃ were optionally replaced with —O—, the resulting compound could be —OCH₂CH₃, —CH₂OCH₃, or —CH₂CH₂OH. It should be understood that if the terminal atom does not contain any free valence electrons, then a hydrogen atom is not required at the terminal end (e.g., —CH₂CH₂CH=O or —CH₂CH₂C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

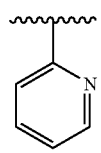

also represents

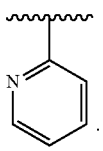

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Pharmaceutically Acceptable Salts

The compounds of this invention can exist in free form for treatment, or where appropriate, as a pharmaceutically acceptable salt.

A "pharmaceutically acceptable salt" means any non-toxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of the ATR protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

ABBREVIATIONS

The following abbreviations are used:
DMSO dimethyl sulfoxide
ATP adenosine triphosphate
$^1$HNMR proton nuclear magnetic resonance
HPLC high performance liquid chromatography
LCMS liquid chromatography-mass spectrometry
TLC thin layer chromatography
Rt retention time
Compound Uses One aspect of this invention provides compounds that are inhibitors of ATR kinase, and thus are useful for treating or lessening the severity of a disease, condition, or disorder where ATR is implicated in the disease, condition, or disorder.

Another aspect of this invention provides compounds that are useful for the treatment of diseases, disorders, and conditions characterized by excessive or abnormal cell proliferation. Such diseases include, a proliferative or hyperproliferative disease. Examples of proliferative and hyperproliferative diseases include, without limitation, cancer and myeloproliferative disorders.

In some embodiments, said compounds are selected from the group consisting of a compound of formula I. The term "cancer" includes, but is not limited to the following cancers. Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

Thus, the term "cancerous cell" as provided herein, includes a cell afflicted by any one of the above-identified conditions. In some embodiments, the cancer is selected from colorectal, thyroid, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Pharmaceutically Acceptable Derivatives or Prodrugs

In addition to the compounds of this invention, pharmaceutically acceptable derivatives or prodrugs of the compounds of this invention may also be employed in compositions to treat or prevent the herein identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensitizers.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

Examples of DNA-damaging agents that may be used in combination with compounds of this invention include, but are not limited to Platinating agents, such as Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mercaptopurine, 5-Fluorouracil (5FU) and relatives); Alkylating agents, such as Nitrogen mustards (Cyclophosphamide, Melphalan, Chlorambucil, mechlorethamine, Ifosfamide and relatives); nitrosoureas (eg Carmustine); Triazenes (Dacarbazine, temozolomide); Alkyl sulphonates (eg Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); Streptomyces family (Bleomycin, Mitomycin C, actinomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepeside); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iminotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Compositions for Administration into a Subject

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other anti-proliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent

Depending upon the particular protein kinase-mediated conditions to be treated or prevented, additional drugs, which are normally administered to treat or prevent that condition, may be administered together with the compounds of this invention.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satraplatin and other derivatives; Topo I inhibitors, such as Camptothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); Streptomyces family (Bleomycin, Mitomycin C, actinomycin) and Ultraviolet light.

Biological Samples

As inhibitors of ATR kinase, the compounds and compositions of this invention are also useful in biological samples. One aspect of the invention relates to inhibiting ATR kinase activity in a biological sample, which method comprises contacting said biological sample with a compound described herein or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. The term "compounds described herein" includes compounds of formula I.

Inhibition of ATR kinase activity in a biological sample is useful for a variety of purposes that are known to one of skill in the art. Examples of such purposes include, but are not limited to, blood transfusion, organ-transplantation, and biological specimen storage.

Study of Protein Kinases

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of ATR is set forth in the Examples below.

Another aspect of the invention provides a method for modulating enzyme activity by contacting a compound described herein with ATR kinase.

Methods of Treatment

In one aspect, the present invention provides a method for treating or lessening the severity of a disease, condition, or disorder where ATR kinase is implicated in the disease state. In another aspect, the present invention provides a method for treating or lessening the severity of an ATR kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the ATR kinase. Another aspect provides a method for treating or lessening the severity of a kinase disease, condition, or disorder by inhibiting enzymatic activity of ATR kinase with an ATR kinase inhibitor.

One aspect of the invention relates to a method of inhibiting ATR kinase activity in a patient, which method comprises administering to the patient a compound described herein, or a composition comprising said compound. In some embodiments, said method is used to treat or prevent a condition selected from proliferative and hyperproliferative diseases, such as cancer.

Another aspect of this invention provides a method for treating, preventing, or lessening the severity of proliferative or hyperproliferative diseases comprising administering an effective amount of a compound, or a pharmaceutically acceptable composition comprising a compound, to a subject in need thereof. In some embodiments, said subject is a patient. The term "patient", as used herein, means an animal, preferably a human.

In some embodiments, said method is used to treat or prevent cancer. In some embodiments, said method is used to treat or prevent a type of cancer with solid tumors. In yet another embodiment, said cancer is selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In some embodiments, the cancer is selected from the cancers described herein. In some embodiments, said cancer is lung cancer, head and neck cancer, pancreatic cancer, gastric cancer, or brain cancer.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

One aspect provides a method for inhibiting ATR in a patient comprising administering a compound described herein as described herein. Another embodiment provides a method of treating cancer comprising administering to a patient a compound described herein, wherein the variables are as defined herein.

Some embodiments comprising administering to said patient an additional therapeutic agent selected from a DNA-damaging agent; wherein said additional therapeutic agent is appropriate for the disease being treated; and said additional therapeutic agent is administered together with said compound as a single dosage form or separately from said compound as part of a multiple dosage form.

In some embodiments, said DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonates, an antimetabolite, or an antibiotic. In other embodiments, said DNA-damaging agent is selected from ionizing radiation, a platinating agent, a Topo I inhibitor, a Topo II inhibitor, or an antibiotic.

Examples of Platinating agents include Cisplatin, Oxaliplatin, Carboplatin, Nedaplatin, Satraplatin and other derivatives. Other platinating agents include Lobaplatin, and Triplatin. Other platinating agents include Tetranitrate, Picoplatin, Satraplatin, ProLindac and Aroplatin.

Examples of Topo I inhibitor include Camptothecin, Topotecan, irinotecan/SN38, rubitecan and other derivatives. Other Topo I inhibitors include Belotecan.

Examples of Topo II inhibitors include Etoposide, Daunorubicin, Doxorubicin, Aclarubicin, Epirubicin, Idarubicin, Amrubicin, Pirarubicin, Valrubicin, Zorubicin and Teniposide.

Examples of Antimetabolites include members of the Folic family, Purine family (purine antagonists), or Pyrimidine family (pyrimidine antagonists). Examples of the Folic family include methotrexate, pemetrexed and relatives; examples of the Purine family include Thioguanine, Fludarabine, Cladribine, 6-Mercaptopurine, and relatives; examples of the Pyrimidine family include Cytarabine, gemcitabine, 5-Fluorouracil (5FU) and relatives.

Some other specific examples of antimetabolites include Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, Azacitidine and Hydroxyurea.

Examples of alkylating agents include Nitrogen mustards, Triazenes, alkyl sulphonates, Procarbazine and Aziridines.

Examples of Nitrogen mustards include Cyclophosphamide, Melphalan, Chlorambucil and relatives; examples of nitrosoureas include Carmustine; examples of triazenes include Dacarbazine and temozolomide; examples of alkyl sulphonates include Busulfan.

Other specific examples of alkylating agents include Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin and Plicamycin.

Examples of antibiotics include Mitomycin, Hydroxyurea; Anthracyclines, Anthracenediones, Streptomyces family. Examples of Anthracyclines include doxorubicin, daunorubicin, epirubicin and other derivatives; examples of Anthracenediones include Mitoxantrone and relatives; examples of Streptomyces family inclue Bleomycin, Mitomycin C, and actinomycin.

In certain embodiments, said platinating agent is Cisplatin or Oxaliplatin; said Topo I inhibitor is Camptothecin; said Topo II inhibitor is Etoposide; and said antibiotic is Mitomycin. In other embodiments, said platinating agent is selected from Cisplatin, Oxaliplatin, Carboplatin, Nedaplatin, or Satraplatin; said Topo I inhibitor is selected from Camptothecin, Topotecan, irinotecan/SN38, rubitecan; said Topo II inhibitor is selected from Etoposide; said antimetabolite is selected from a member of the Folic Family, the Purine Family, or the Pyrimidine Family; said alkylating agent is selected from nitrogen mustards, nitrosoureas, triazenes, alkyl sulfonates, Procarbazine, or aziridines; and said antibiotic is selected from Hydroxyurea, Anthracyclines, Anthracenediones, or Streptomyces family.

Another embodiment provides a method of promoting cell death in cancer cells comprising administering to a patient a compound described herein, or a composition comprising said compound.

Yet another embodiment provides a method of preventing cell repair of DNA damage in cancer cells comprising administering to a patient a compound described herein, or a composition comprising said compound. Yet another embodiment provides a method of preventing cell repair caused by of DNA damage in cancer cells comprising administering to a patient a compound of formula I, or composition comprising said compound.

Another embodiment provides a method of sensitizing cells to DNA damaging agents comprising administering to a patient a compound described herein, or a composition comprising said compound.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1 or H2AX. In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

Yet another embodiment provides use of a compound described herein as a radio-sensitizer or a chemo-sensitizer.

Yet other embodiment provides use of a compound of formula I as a single agent (monotherapy) for treating cancer. In some embodiments, the compounds of formula I are used for treating patients having cancer with a DNA-damage response (DDR) defect. In other embodiments, said defect is a mutation or loss of ATM, p53, CHK2, MRE11, RAD50, NBS1, 53BP1, MDC1, or H2AX.

SCHEMES

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). Below are a set of generic schemes that illustrate generally how to prepare the compounds of the present disclosure.

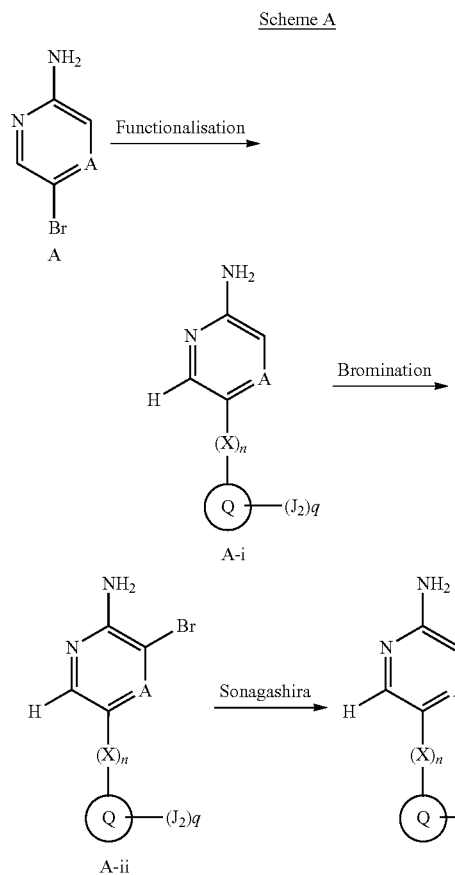

Scheme A depicts a general method for making compounds of Formula I. Compound A is functionalised via either an SNAr reaction or a range of known metal mediated reactions such as, but not limited to, Suzuki reactions, Stille couplings, Buchwald-Hartwig reactions and carbonylation reactions to give compounds of Formula A-i. $J^2$ substituents on ring Q can undergo further functionalisation by known reactions such as, but not limited to, Mitsunobu reactions and acylation. These compounds are then brominated under standard conditions known to those skilled in the art such as, but not limited to, treatment with N-bromosuccinimide to give compounds of Formula A-ii. Reaction of these compounds under Sonagashira conditions gives rise to compounds of the Formula I. $J^5$ substituents on $R^5$ can undergo further function-alisation by reactions known to those skilled in the art such as, but not limited to, Mitsunobu reactions and acylation.

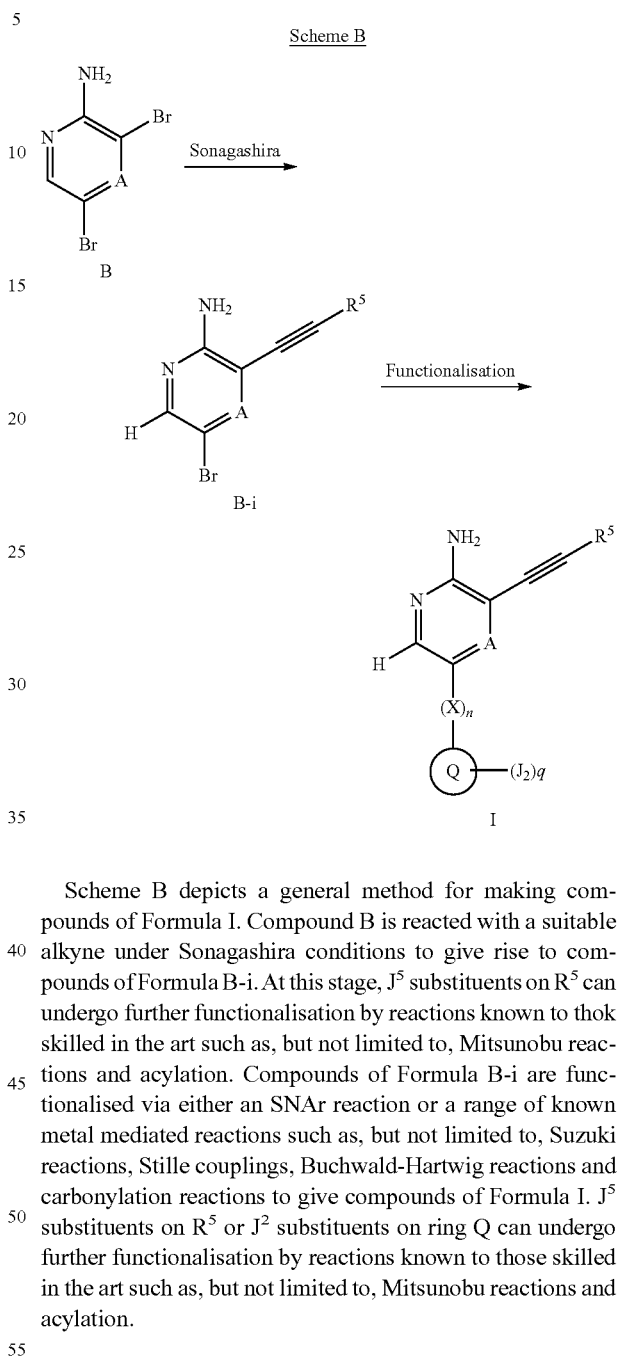

Scheme B depicts a general method for making compounds of Formula I. Compound B is reacted with a suitable alkyne under Sonagashira conditions to give rise to compounds of Formula B-i. At this stage, $J^5$ substituents on $R^5$ can undergo further functionalisation by reactions known to thok skilled in the art such as, but not limited to, Mitsunobu reactions and acylation. Compounds of Formula B-i are functionalised via either an SNAr reaction or a range of known metal mediated reactions such as, but not limited to, Suzuki reactions, Stille couplings, Buchwald-Hartwig reactions and carbonylation reactions to give compounds of Formula I. $J^5$ substituents on $R^5$ or $J^2$ substituents on ring Q can undergo further functionalisation by reactions known to those skilled in the art such as, but not limited to, Mitsunobu reactions and acylation.

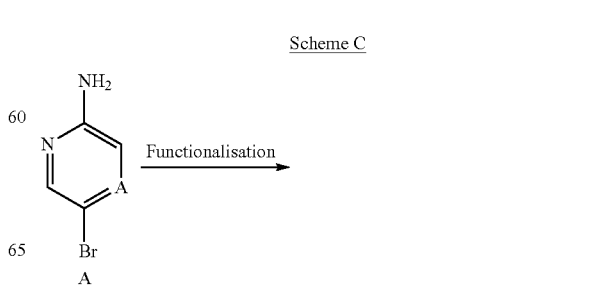

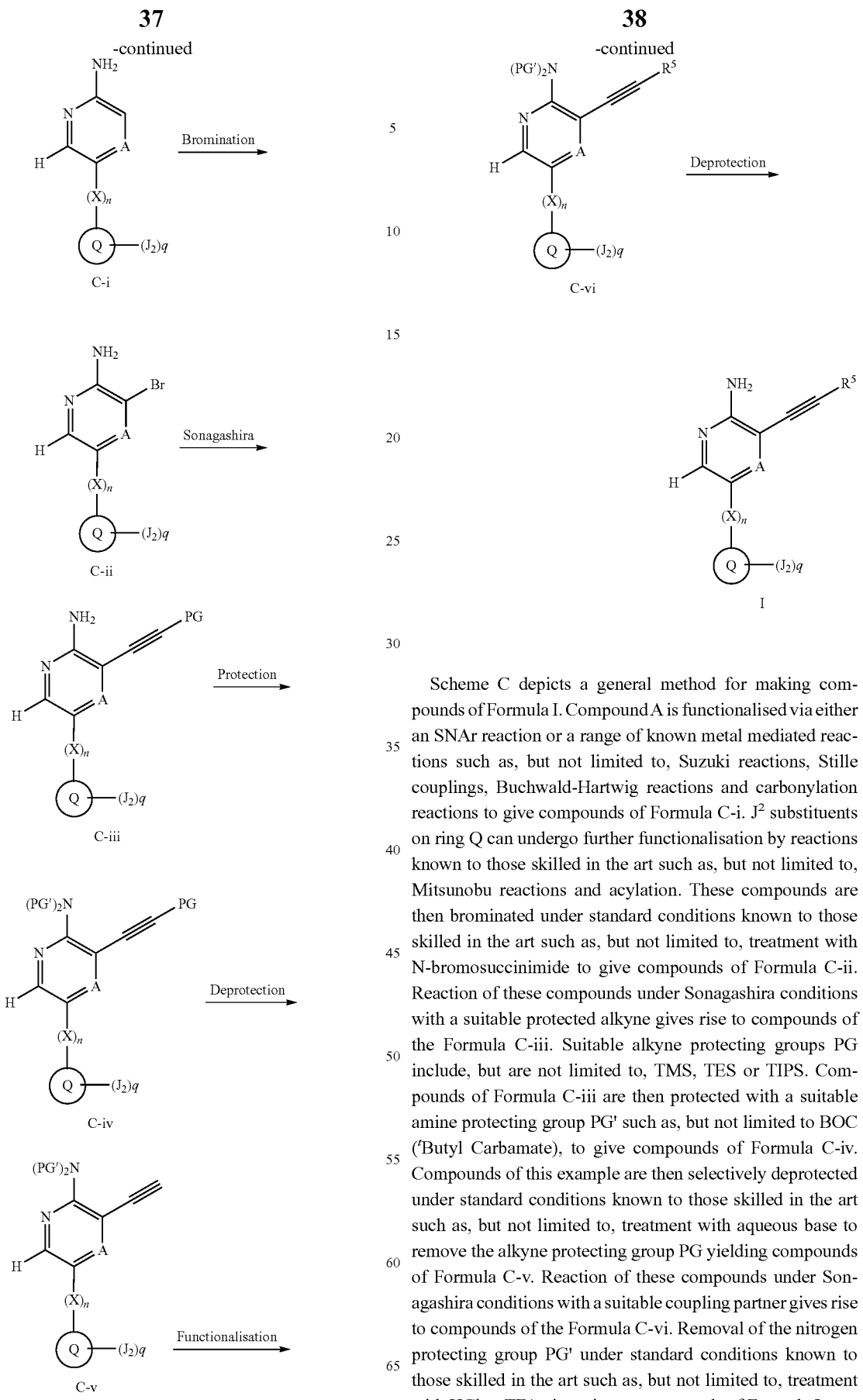

Scheme C depicts a general method for making compounds of Formula I. Compound A is functionalised via either an SNAr reaction or a range of known metal mediated reactions such as, but not limited to, Suzuki reactions, Stille couplings, Buchwald-Hartwig reactions and carbonylation reactions to give compounds of Formula C-i. $J^2$ substituents on ring Q can undergo further functionalisation by reactions known to those skilled in the art such as, but not limited to, Mitsunobu reactions and acylation. These compounds are then brominated under standard conditions known to those skilled in the art such as, but not limited to, treatment with N-bromosuccinimide to give compounds of Formula C-ii. Reaction of these compounds under Sonagashira conditions with a suitable protected alkyne gives rise to compounds of the Formula C-iii. Suitable alkyne protecting groups PG include, but are not limited to, TMS, TES or TIPS. Compounds of Formula C-iii are then protected with a suitable amine protecting group PG' such as, but not limited to BOC ($^t$Butyl Carbamate), to give compounds of Formula C-iv. Compounds of this example are then selectively deprotected under standard conditions known to those skilled in the art such as, but not limited to, treatment with aqueous base to remove the alkyne protecting group PG yielding compounds of Formula C-v. Reaction of these compounds under Sonagashira conditions with a suitable coupling partner gives rise to compounds of the Formula C-vi. Removal of the nitrogen protecting group PG' under standard conditions known to those skilled in the art such as, but not limited to, treatment with HCl or TFA gives rise to compounds of Formula I.

Scheme D

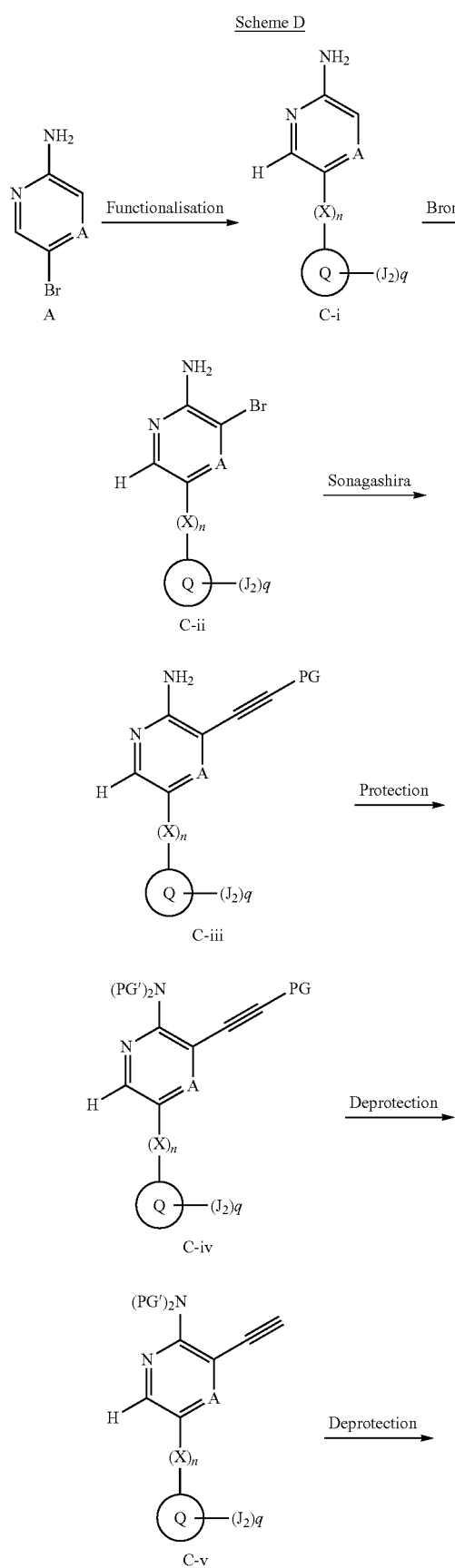

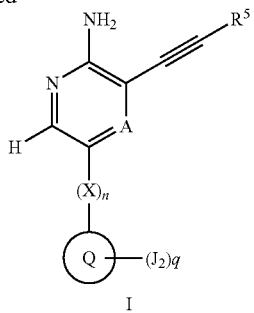

Scheme D depicts a general method for making compounds of Formula I wherein $R^5$ is H. Following the procedures outlined in Scheme C above, compounds of Formula C-v are synthesised from Compound A. The nitrogen protecting group PG', which can be but is not limited to BOC ('Butyl Carbamate), can be removed under standard conditions known to those skilled in the art such as, but not limited to, treatment with HCl or TFA to give rise to compounds of Formula I.

Scheme E

Scheme E depicts an alternative general method for making compounds of Formula C-v (wherein $R^5$ is H). Compound B is reacted with a suitably protected alkyne under Sonagashira conditions gives rise to compounds of the Formula E-i. Suitable alkyne protecting groups PG include, but are not limited to, TMS, TES or TIPS. Compounds of Formula E-i are then protected with a suitable amine protecting group PG' such as, but not limited to BOC (ᵗButyl Carbamate), to give compounds of Formula E-ii. Compounds of Formula E-ii are functionalised via either an SNAr reaction or a range of known metal mediated reactions such as, but not limited to, Suzuki reactions, Stille couplings, Buchwald-Hartwig reactions and carbonylation reactions. Under these reaction conditions the alkyne protecting group PG is removed to give compounds of Formula C-v. These compounds can be further functionalised as described in Scheme C to give compounds of Formula I.

EXAMPLES

In order that this invention be more fully understood, the following preparative and testing examples are set forth. These examples are for the purpose of illustration only and are not to be construed as limiting the scope of the invention in any way. ¹H-NMR spectra were recorded at 400 MHz using a Bruker DPX 400 instrument. Mass spec. samples were analyzed on a MicroMass Quattro Micro mass spectrometer operated in single MS mode with electrospray ionization.

Example 1

3-[2-[3-Amino-6-(4-isopropylsulfonylphenyl)pyrazin-2-yl]ethynyl]phenol (Compound I-35)

SCHEME I

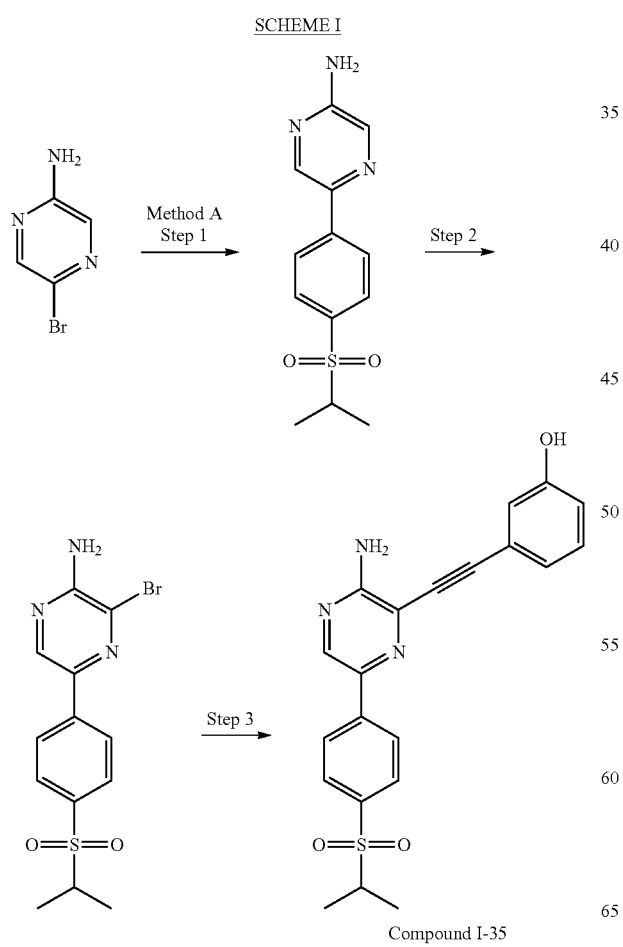

Compound I-35

Method A

Step 1:
5-(4-(Isopropylsulfonyl)phenyl)pyrazin-2-amine

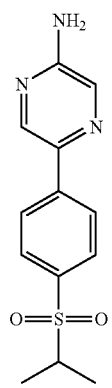

5-Bromopyrazin-2-amine (5 g, 28.74 mmol), (4-isopropylsulfonylphenyl)boronic acid (7.866 g, 34.49 mmol) and K₃PO₄ (12.20 g, 57.48 mmol) were combined in MeCN (100 mL)/Water (25 mL) and Pd[P(tBu)₃]₂ (734.4 mg, 1.437 mmol) was added. The reaction was heated at 60° C. for 1 hour. The reaction mixture was cooled to ambient temperature and diluted with EtOAc and water. The layers were separated and the aqueous layer extracted with EtOAc (×3). The combined organic layers were dried (MgSO₄), filtered and concentrated in vacuo. The residue was triturated from DCM and isolated by filtration to give the sub-title compound as an orange solid (6.43 g, 76% Yield). ¹H NMR (400.0 MHz, DMSO) δ 1.17 (d, 6H), 3.43 (sept, 1H), 6.86 (s, 2H), 7.87 (d, 2H), 8.00 (s, 1H), 8.20 (d, 2H) and 8.67 (s, 1H) ppm; MS (ES⁺) 278.2.

Step 2: 3-Bromo-5-(4-(isopropylsulfonyl)phenyl)pyrazin-2-amine

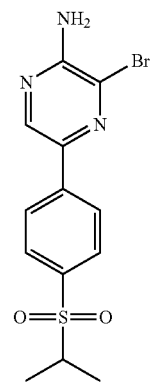 [SMILES: CC(C)S(=O)(=O)c1ccc(-c2cnc(N)c(Br)n2)cc1]

5-(4-(Isopropylsulfonyl)phenyl)pyrazin-2-amine (10 g, 36.06 mmol) was dissolved in dry DMF (70 mL) and N-bromosuccinimide (6.418 g, 36.06 mmol) was added portionwise. The mixture was stirred at ambient temperature for 2 hours. The reaction mixture was poured into water (200 mL) and stirred for 5 minutes. The solid was isolated by filtration and washed with water. The wet solid was dissolved in ethyl acetate and any insoluble material removed by filtration. The aqueous layer was separated and the organic phase washed with saturated aqueous $Na_2S_2O_3$ (×1) and dried ($MgSO_4$). The organic extracts were filtered through a plug of Florisil (200 mesh), eluting with ethyl acetate. The filtrate was concentrated to ca. 50 mL and resultant precipitate isolated by filtration and washed with Petroleum Ether. The solid was further dried under high vacuum to give the sub-title compound as a pale orange solid (8.0 g, 62% Yield)). $^1$HNMR (400.0 MHz, DMSO) δ 1.17 (d, 6H), 3.41-3.49 (m, 1H), 7.16 (br s, 2H), 7.89 (d, 2H), 8.17 (d, 2H) and 8.76 (s, 1H) ppm; MS (ES$^+$) 356.1.

Step 3: 3-[2-[3-Amino-6-(4-isopropylsulfonylphenyl)pyrazin-2-yl]ethynyl]phenol

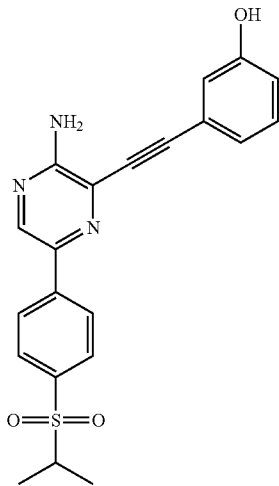 [SMILES: CC(C)S(=O)(=O)c1ccc(-c2cnc(N)c(C#Cc3cccc(O)c3)n2)cc1]

3-Ethynylphenol (187.0 mg, 103.7 μL, 1.583 mmol) was added to a solution of 3-bromo-5-(4-(isopropylsulfonyl)phenyl)pyrazin-2-amine (500 mg, 1.319 mmol), $Et_3N$ (1.335 g, 1.839 mL, 13.19 mmol), Copper(I) iodide (30.15 mg, 0.1583 mmol) and Pd(PPh$_3$)$_4$ (76.21 mg, 0.06595 mmol) in DMF (5 mL) and the resulting solution heated at 100° C. for 90 minutes in a sealed tube. The reaction mixture was cooled to ambient temperature and diluted with EtOAc and 1MHCl/brine (1:1). The layers were separated and the aqueous layer was extracted with ethyl acetate (×2). The combined organics extracts were washed with brine, dried over (MgSO$_4$) and concentrated in vacuo. The residue was purified by column chromatography (ISCO Companion™, 40 g column, eluting with 0 to 100% EtOAc/Petroleum Ether) to give the title product as a yellow solid (352 mg, 68% Yield). $^1$H NMR (400.0 MHz, DMSO) δ 1.18 (d, 6H), 3.44 (sept, 1H), 6.87-6.90 (m, 1H), 7.13-7.15 (m, 3H), 7.19-7.21 (m, 1H), 7.27 (t, 1H), 7.90 (d, J=8.6 Hz, 2H), 8.24 (d, J=8.6 Hz, 2H), 8.75 (s, 1H) and 9.77 (s, 1H) ppm; MS (ES$^+$) 394.2.

The following compounds were also prepared using a sequence similar to that outlined in Method A:

Compound I-1: 3-[2-(3-Fluorophenyl)ethynyl]-5-(4-isopropylsulfonylphenyl)pyrazin-2-amine

MS (ES$^+$) 396.

Compound I-2: 5-(4-Isopropylsulfonylphenyl)-3-[2-(1-naphthyl)ethynyl]pyrazin-2-amine $^1$H NMR (400.0 MHz, DMSO) δ 1.19 (d, 6H), 3.46 (sept, 1H), 7.21 (s, 2H), 7.61-7.68 (m, 2H), 7.72-7.76 (m, 1H), 7.93 (d, 2H), 8.05-8.14 (m, 3H), 8.29 (d, 2H) and 8.40; MS (ES$^+$) 428.1.

Compound I-3: 5-(4-Isopropylsulfonylphenyl)-3-[2-(3-methoxyphenyl)ethynyl]pyrazin-2-amine $^1$H NMR (400.0 MHz, DMSO) δ 1.18 (d, 6H), 3.45 (sept, 1H), 3.82 (s, 3H), 7.04-7.07 (m, 1H), 7.18 (br s, 2H), 7.36-7.41 (m, 3H), 7.91 (d, 2H), 8.24 (d, 2H) and 8.76 (s, 1H) ppm; MS (ES$^+$) 408.5.

Compound 1-4: (2R)-4-[3-Amino-6-(4-isopropylsulfonylphenyl)pyrazin-2-yl]but-3-yn-2-ol $^1$H NMR (400.0 MHz, DMSO) δ 1.17 (d, 6H), 1.44 (d, 3H), 3.44 (sept, 1H), 4.69 (q, 1H), 5.62 (s, 1H), 6.96 (s, 2H), 7.88 (d, 2H), 8.20 (d, 2H) and 8.72 (s, 1H) ppm; MS (ES$^+$) 346.1.

Compound I-6: N-[3-[2-[3-Amino-6-(4-isopropylsulfonylphenyl)pyrazin-2-yl]ethynyl]phenyl]acetamide $^1$HNMR (400.0 MHz, DMSO) δ 1.18 (d, 6H), 2.08 (s, 3H), 3.45 (t, 1H), 7.16 (s, 2H), 7.40 (t, 1H), 7.47 (t, 1H), 7.49 (s, 1H), 7.89-7.91 (m, 2H), 8.01 (d, 1H), 8.25 (dd, 2H), 8.76 (s, 1H) and 10.11 (s, 1H) ppm; MS (ES$^+$) 435.26.

Compound I-7: 5-(4-Isopropylsulfonylphenyl)-3-(2-phenylethynyl)pyrazin-2-amine $^1$H NMR (400.0 MHz, DMSO) δ 1.19 (d, 6H), 3.41-3.50 (m, 1H), 7.14 (br s, 2H), 7.48-7.49 (m, 3H), 7.78-7.81 (m, 2H), 7.91 (d, 2H), 8.24 (d, 2H) and 8.76 (s, 1H) ppm; MS (ES$^+$) 378.2.

Compound I-8: 3-(2-Cyclohexylethynyl)-5-(4-isopropylsulfonylphenyl)pyrazin-2-amine

MS (ES$^+$) 384.1.

Compound I-9: 3-[2-(3-Chlorophenyl)ethynyl]-5-(4-isopropylsulfonylphenyl)pyrazin-2-amine $^1$H NMR (400.0 MHz, DMSO) δ 1.18 (d, 6H), 3.45 (t, 1H), 7.25 (s, 2H), 7.48-7.57 (m, 2H), 7.73 (dt, 1H), 7.91 (d, 2H), 8.00 (t, 1H), 8.24 (dd, 2H) and 8.78 (s, 1H) ppm; MS (ES$^+$) 412.8.

Compound I-10: 5-(4-isopropylsulfonylphenyl)-3-(3-phenylprop-1-ynyl)pyrazin-2-amine $^1$H NMR (400.0 MHz, DMSO) δ 1.19 (d, 6H), 3.45 (m, 1H), 4.19 (s, 2H), 6.47 (s, 1H), 7.25-7.28 (m, 1H), 7.35 (d, 4H), 7.95 (d, 2H), 8.39 (d, 2H), 8.89 (s, 1H) and 12.25 (s, 1H) ppm; MS (ES$^+$) 392.21.

Compound I-11: 5-(4-Isopropylsulfonylphenyl)-3-[2-(m-tolyl)ethynyl]pyrazin-2-amine $^1$H NMR (400.0 MHz, DMSO) δ 1.18 (d, 6H), 2.36 (s, 3H), 3.45 (sept, 1H), 7.14 (s, 2H), 7.29-7.30 (m, 1H), 7.36 (t, 1H), 7.58 (d, 1H), 7.64 (s, 1H), 7.91 (d, 2H), 8.24 (d, 2H) and 8.76 (s, 1H) ppm; MS (ES⁺) 392.4.

Compound I-12: 3-[2-(2-Chlorophenyl)ethynyl]-5-(4-isopropylsulfonylphenyl)pyrazin-2-amine ¹H NMR (400.0 MHz, DMSO) δ 1.18 (d, 6H), 3.45 (t, 1H), 7.15 (br s, 2H), 7.46-7.54 (m, 2H), 7.65 (dd, 1H), 7.90-7.97 (m, 3H), 8.24 (dd, 2H) and 8.81 (s, 1H) ppm; MS (ES⁺) 412.18.

Compound I-13: 5-(4-Isopropylsulfonylphenyl)-3-[2-(3-pyridyl)ethynyl]pyrazin-2-amine ¹H NMR (400.0 MHz, DMSO) δ 1.18 (d, 6H), 3.45 (t, 1H), 7.27 (s, 2H), 7.52 (dd, 1H), 7.91 (d, 2H), 8.20-8.25 (m, 3H), 8.64 (d, 1H), 8.79 (s, 1H) and 8.97 (s, 1H) ppm; MS (ES⁺) 379.18.

Compound I-14: 3-[2-(4-Fluorophenyl)ethynyl]-5-(4-isopropylsulfonylphenyl)pyrazin-2-amine

MS (ES⁺) 396.

Compound I-15: 4-[2-[3-Amino-6-(4-isopropylsulfonylphenyl)pyrazin-2-yl]ethynyl]benzonitrile

MS (ES⁺) 403.

Compound I-19: 5-(4-Isopropylsulfonylphenyl)-3-[2-(2-methoxyphenyl)ethynyl]pyrazin-2-amine

MS (ES⁺) 408.1.

Compound I-21: 3-[2-(3-Aminophenyl)ethynyl]-5-(4-isopropylsulfonylphenyl)pyrazin-2-amine ¹H NMR (400.0 MHz, DMSO) δ 1.18 (d, 6H), 3.44 (sept, 1H), 5.39 (br s, 2H), 6.66-6.69 (m, 1H), 6.93 (d, 2H), 7.06-7.13 (m, 3H), 7.90 (d, 2H), 8.24 (d, 2H) and 8.74 (s, 1H) ppm; MS (ES⁺) 393.1.

Compound I-22: 5-(4-Isopropylsulfonylphenyl)-3-[2-(2-thienyl)ethynyl]pyrazin-2-amine ¹H NMR (400.0 MHz, DMSO) δ 1.18 (d, 6H), 3.45 (sept, 1H), 7.19 (br s, 2H), 7.18-7.21 (m, 1H), 7.67-7.69 (m, 1H), 7.70-7.79 (m, 1H), 7.90 (d, 2H), 8.23 (d, 2H) and 8.76 (s, 1H) ppm; MS (ES⁺) 384.1.

Compound I-27: 3-(2-Cyclopropylethynyl)-5-(4-isopropylsulfonylphenyl)pyrazin-2-amine ¹H NMR (400.0 MHz, DMSO) δ 0.94-0.97 (m, 4H), 1.17 (d, 6H), 1.65-1.71 (m, 1H), 3.43 (sept, 1H), 6.89 (s, 2H), 7.87 (d, 2H), 8.18 (d, 2H) and 8.65 (s, 1H) ppm; MS (ES⁺) 342.2.

Compound I-29: (2S)-4-[3-Amino-6-(4-isopropylsulfonylphenyl)pyrazin-2-yl]but-3-yn-2-ol ¹H NMR (400.0 MHz, DMSO) δ 1.17 (d, 6H), 1.44 (d, 3H), 3.43 (sept, 1H), 4.69 (q, 1H), 5.61 (br s, 2H), 6.97 (br s, 2H), 7.88 (dd, 2H), 8.20 (dd, 2H) and 8.72 (s, 1H) ppm; MS (ES⁺) 346.1.

Compound I-31: 5-(4-Isopropylsulfonylphenyl)-3-[2-(3-thienyl)ethynyl]pyrazin-2-amine

MS (ES⁺) 384.

Compound I-32: 5-(4-Isopropylsulfonylphenyl)-3-[2-(4-pyridyl)ethynyl]pyrazin-2-amine ¹H NMR (400.0 MHz, DMSO) δ 1.18 (d, 6H), 3.45 (sept, 1H), 7.32 (s, 2H), 7.76 (d, 2H), 7.91 (d, 2H), 8.24 (d, 2H), 8.68 (d, 2H) and 8.82 (s, 1H) ppm; MS (ES⁺) 379.1.

Compound I-33: 5-(4-Isopropylsulfonylphenyl)-3-[2-(2-pyridyl)ethynyl]pyrazin-2-amine ¹H NMR (400.0 MHz, DMSO) δ 1.18 (d, 6H), 3.45 (s, 1H), 7.23 (s, 2H), 7.50 (d, 1H), 7.89-7.96 (m, 4H), 8.25-8.27 (m, 2H), 8.66 (s, 1H) and 8.82 (s, 1H) ppm; MS (ES⁺) 379.18.

Compound I-37: 3-((2-aminophenyl)ethynyl)-5-(4-(isopropylsulfonyl)phenyl)pyrazin-2-amine ¹H NMR (400.0 MHz, DMSO) δ 1.18 (d, J=6.9 Hz, 6H), 3.44 (t, J=6.8 Hz, 1H), 5.67 (s, 2H), 6.59 (t, J=7.5 Hz, 1H), 6.77 (d, J=8.0 Hz, 1H), 7.07 (s, 2H), 7.15 (dd, J=1.5, 15.4 Hz, 1H), 7.43 (dd, J=1.4, 7.7 Hz, 1H), 7.90 (d, J=8.5 Hz, 2H), 8.25 (d, J=8.5 Hz, 2H) and 8.72 (s, 1H) ppm; MS (ES⁺) 393.0

Compound I-38: 5-(4-(isopropylsulfonyl)phenyl)-3-(1-methyl-1H-imidazol-5-yl)ethynyl)pyrazin-2-amine ¹H NMR (400.0 MHz, DMSO) δ 1.18 (d, J=6.8 Hz, 6H), 3.43-3.46 (m, 1H), 3.78 (s, 3H), 7.12 (s, 2H), 7.53 (br s, 1H), 7.86 (br s, 1H), 7.90 (d, J=8.5 Hz, 2H), 8.23 (d, J=8.5 Hz, 2H) and 8.77 (s, 1H) ppm; MS (ES⁺) 382.0

Compound I-39: 3-((2-fluorophenyl)ethynyl)-5-(4-(isopropylsulfonyl)phenyl)pyrazin-2-amine ¹H NMR (400.0 MHz, DMSO) δ 1.18 (d, J=6.8 Hz, 6H), 3.45 (t, J=6.8 Hz, 1H), 7.15 (s, 2H), 7.33 (td, J=7.5, 2.8 Hz, 2H), 7.55 (s, 1H), 7.90-7.93 (m, 3H), 8.24 (d, J=8.5 Hz, 2H) and 8.80 (s, 1H) ppm; MS (ES⁺) 396.3

Example 2

5-(4-Isopropylsulfonylphenyl)-3-[2-[3-(2-morpholinoethoxy)phenyl]ethynyl]pyrazin-2-amine (Compound I-36)

SCHEME II

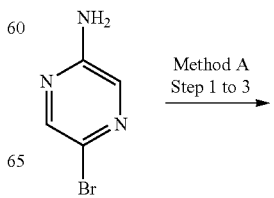

Method A
Step 1 to 3

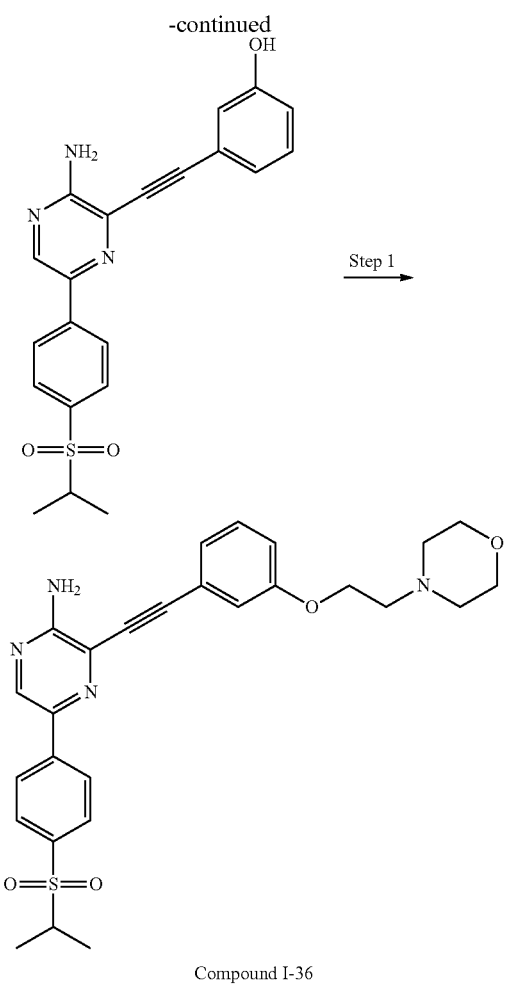

Compound I-36

Method B

Step 1: 5-(4-Isopropylsulfonylphenyl)-3-[2-[3-(2-morpholinoethoxy)phenyl]ethynyl]pyrazin-2-amine

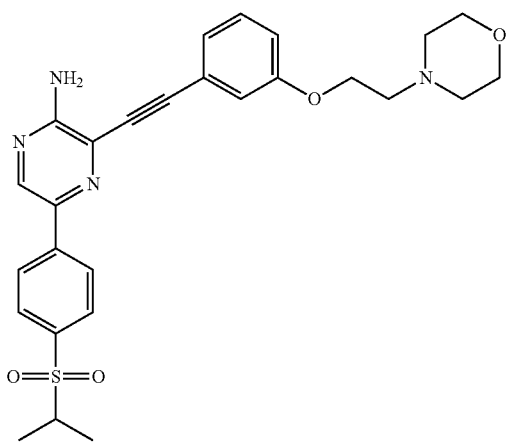 [SMILES: CC(C)S(=O)(=O)c1ccc(-c2cnc(N)c(C#Cc3cccc(OCCN4CCOCC4)c3)n2)cc1]

4-(2-Chloroethyl)morpholine hydrochloride (31.93 mg, 0.1716 mmol) was added to a stirred solution of 3-[2-[3-amino-6-(4-isopropylsulfonylphenyl)pyrazin-2-yl]ethynyl] phenol (45 mg, 0.1144 mmol) and $K_2CO_3$ (39.53 mg, 0.2860 mmol) in DMF (1 mL) and the reaction mixture warmed to 65° C. for 16 hours. The reaction mixture was partitioned between DCM and saturated aqueous $NaHCO_3$ and stirred for 5 minutes. The layers were separated by filtration through a phase separation cartridge and the aqueous layer retained was washed with DCM (×2). The combined organic extracts were passed through a 5 g SCX-2 cartridge and washed with MeOH. The product was eluted by washing the cartridge with 2M $NH_3$ in MeOH. The solvent was removed in vacuo and the material was purified by reverse phase preparative HPLC [Waters Sunfire C18, 10 μM, 100 Å column, gradient 10%-95% B (solvent A: 0.05% TFA in water; solvent B: $CH_3CN$) over 16 minutes at 25 mL/min]. The fractions were collected and freeze-dried to give the mono-TFA salt of the title compound as a yellow solid (29 mg, 41% Yield). $^1$H NMR (400.0 MHz, DMSO) δ 1.09 (d, 6H), 3.22-3.25 (m, 2H), 3.41-3.74 (m, 7H), 4.01 (d, 2H), 4.43 (s, 2H), 6.98 (s, 2H), 7.14 (d, 1H), 7.41-7.48 (m, 3H), 7.92 (d, 2H), 8.23 (d, 2H), 8.78 (s, 1H) and 9.88 (s, 1H) ppm; (ES$^+$) 507.3.

The following compounds were also prepared using a sequence similar to that outlined in Method B:

Compound I-20: 3-[2-[3-[3-(Dimethylamino)propoxy]phenyl]ethynyl]-5-(4-isopropylsulfonylphenyl)pyrazin-2-amine $^1$H NMR (400.0 MHz, DMSO) δ 1.18 (d, 6H), 2.11-2.15 (m, 2H), 2.84 (d, 6H), 3.21-3.27 (m, 2H), 3.45 (sept, 1H), 4.13 (t, 2H), 7.05-7.08 (m, 1H), 7.17 (s, 2H), 7.40 (d, 3H), 7.91 (d, 2H), 8.23 (d, 2H), 8.77 (s, 1H) and 9.34 (s, 1H) ppm; MS (ES$^+$) 479.3.

Compound I-26: 3-[2-[3-(2-Dimethylaminoethyloxy)phenyl]ethynyl]-5-(4-isopropylsulfonylphenyl)pyrazin-2-amine $^1$H NMR (400.0 MHz, DMSO) δ 1.20 (d, 6H), 2.91 (d, 6H), 3.45 (sept, 1H), 3.55-3.57 (m, 2H), 4.39-4.41 (m, 2H), 7.11-7.14 (m, 1H), 7.18 (s, 2H), 7.41-7.47 (m, 3H), 7.91 (d, 2H), 8.23 (d, 2H), 8.78 (s, 1H) and 9.60 (s, 1H) ppm; MS (ES$^+$) 465.3.

Example 3

3-[2-[3-(3-Aminopropoxy)phenyl]ethynyl]-5-(4-isopropylsulfonylphenyl)pyrazin-2-amine (Compound I-24)

SCHEME III

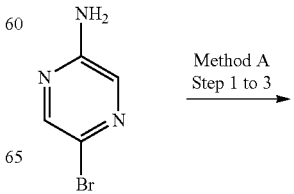

Method A
Step 1 to 3

49

-continued

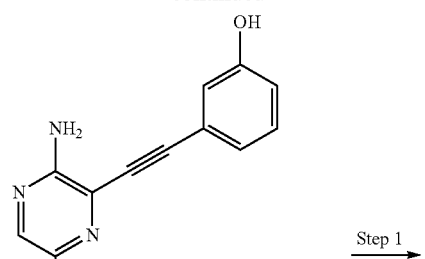

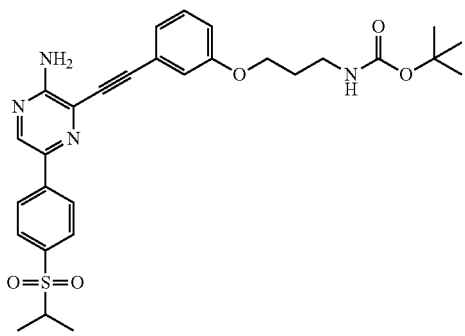 [SMILES: CC(C)S(=O)(=O)c1ccc(-c2cnc(N)c(C#Cc3cccc(OCCCNC(=O)OC(C)(C)C)c3)n2)cc1]

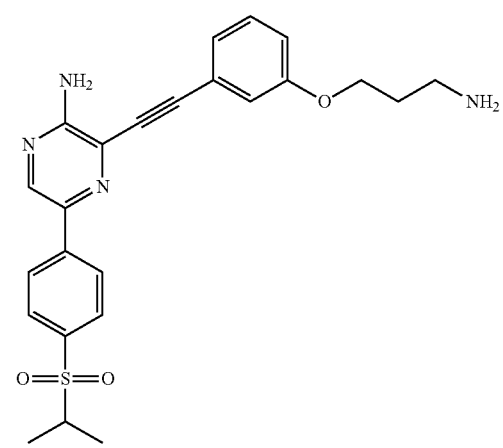 [SMILES: CC(C)S(=O)(=O)c1ccc(-c2cnc(N)c(C#Cc3cccc(OCCCN)c3)n2)cc1]

Compound I-24

50

Method C

Step 1: tert-Butyl (3-(3-((3-amino-6-(4-(isopropyl-sulfonyl)phenyl)pyrazin-2-yl)ethynyl)phenoxy)propyl)carbamate

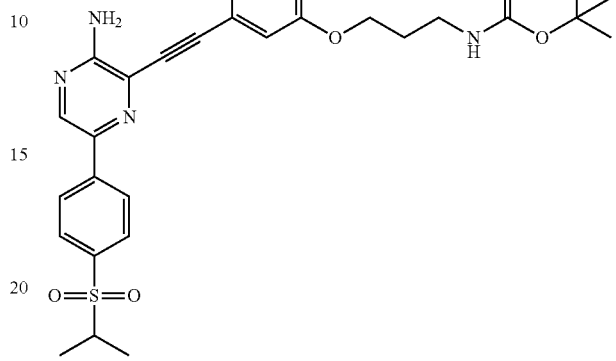

tert-Butyl N-(3-bromopropyl)carbamate (40.86 mg, 0.1716 mmol) was added to a stirred solution of 3-[2-[3-amino-6-(4-isopropylsulfonylphenyl)pyrazin-2-yl]ethynyl]phenol (45 mg, 0.1144 mmol) and $K_2CO_3$ (39.53 mg, 0.2860 mmol) in DMF (1 mL) and the reaction mixture warmed to 65° C. for 16 hours. The reaction mixture was partitioned between DCM and saturated aqueous $NaHCO_3$ and stirred for 5 minutes. The layers were separated by filtration through a phase separation cartridge and the aqueous layer retained was washed with DCM (×2). The combined organics were concentrated in vacuo and used directly in the next step.

Step 2: 3-[2-[3-(3-Aminopropoxy)phenyl]ethynyl]-5-(4-isopropylsulfonylphenyl)pyrazin-2-amine TFA (1 mL) was added to a stirred solution of tert-Butyl (3-(3-((3-amino-6-(4-(isopropylsulfonyl)phenyl)pyrazin-2-yl)ethynyl)phenoxy)propyl)carbamate (crude residue used directly from Step 1) in DCM (5 mL) at ambient temperature. The reaction was allowed to stir at this temperature for 6 hours. The solvent was removed in vacuo and the residue azeotroped with DCM (×2) and ether (×2). The reaction mixture was passed through a 5 g SCX-2 cartridge and washed with MeOH. The product was eluted by washing the cartridge with 2M $NH_3$ in MeOH. The solvent was removed in vacuo and the residue was purified by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The fractions were collected and freeze-dried to give the mono-TFA salt of the title compound as a yellow solid (24 mg, 37% Yield). $^1$H NMR (400.0 MHz, DMSO) δ 1.18 (d, 6H), 2.00-2.06 (m, 2H), 2.97-3.02 (m, 2H), 3.46 (sept, 1H), 4.13 (t, 2H), 7.05-7.08 (m, 1H), 7.17 (s, 2H), 7.39-7.41 (m, 3H), 7.71 (s, 3H), 7.91 (d, 2H), 8.23 (d, 2H) and 8.77 (s, 1H) ppm; MS (ES$^+$) 451.2.

The following compound was also prepared using a sequence similar to that outlined in Method C:

Compound I-25: 3-[2-[3-(2-Aminoethoxy)phenyl] ethynyl]-5-(4-isopropylsulfonylphenyl)pyrazin-2-amine $^1$H NMR (400.0 MHz, DMSO) δ 1.18 (d, 6H), 3.26-3.29 (m, 2H), 3.45 (sept, 1H), 4.24 (t, 2H), 7.09-7.12 (m, 1H), 7.18 (s, 2H), 7.42-7.44 (m, 3H), 7.91 (d, 2H), 7.95 (s, 3H), 8.24 (d, 2H) and 8.78 (s, 1H) ppm; MS (ES$^+$) 437.3.

Example 4

3-[2-[3-Amino-6-(2-methylsulfinylphenyl)pyrazin-2-yl]ethynyl]phenol (Compound I-23)

SCHEME IV

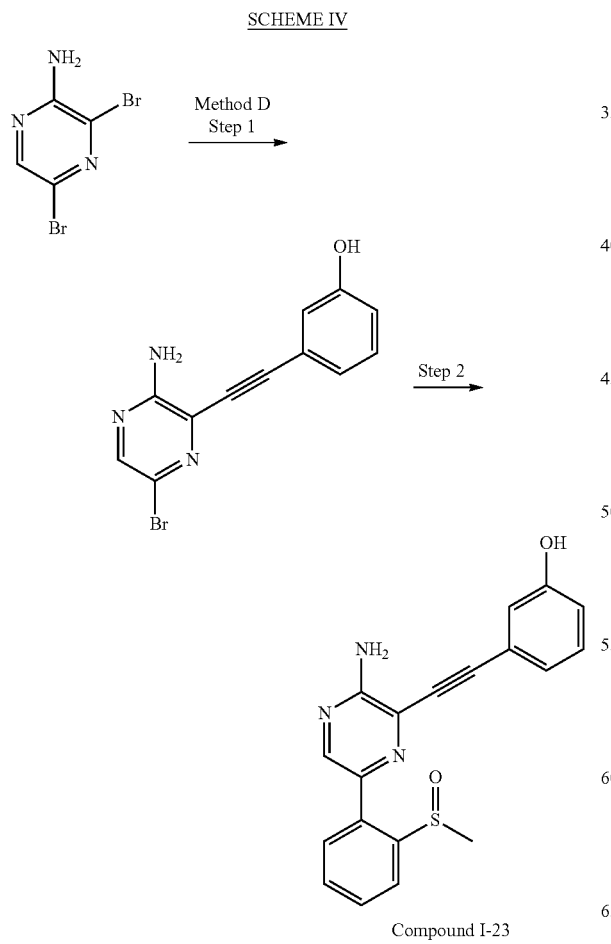

Compound I-23

Method D

Step 1:
3-[2-(3-Amino-6-bromo-pyrazin-2-yl)ethynyl]phenol

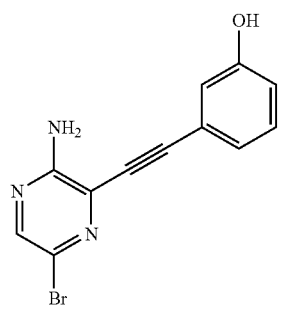 [SMILES: Nc1ncc(Br)nc1C#Cc1cccc(O)c1]

3-Ethynylphenol (560.5 mg, 310.9 μL, 4.745 mmol) was added dropwise to a solution of 3,5-dibromopyrazin-2-amine (1 g, 3.954 mmol), triethylamine (4.001 g, 5.511 mL, 39.54 mmol), copper (I) iodide (90.37 mg, 0.4745 mmol) and Pd(PPh$_3$)$_4$ (228.5 mg, 0.1977 mmol) in DMF (10 mL) and the resulting solution heated at 120° C. for 3 hours. The reaction mixture was cooled to ambient temperature and diluted with EtOAc and 1 M HCl/brine (1/1) and the layers separated. The aqueous layer was extracted with EtOAc (×2) and the combined organic extracts washed with brine (×2), dried (MgSO$_4$) and concentrated in vacuo. The residue was purified by column chromatography (ISCO Companion™, 120 g column, eluting with 0 to 40% EtOAc/Petroleum Ether, dry loaded) to give the sub-title product as a yellow solid (815 mg, 71% Yield). $^1$H NMR (400.0 MHz, DMSO) δ 6.88 (dd, 1H), 7.00 (br s, 2H), 7.11-7.11 (m, 1H), 7.17 (d, 1H), 7.25 (t, 1H), 8.12 (s, 1H) and 9.77 (s, 1H) ppm; MS (ES$^+$) 292.0.

Step 1: 3-[2-[3-Amino-6-(2-methylsulfinylphenyl) pyrazin-2-yl]ethynyl]phenol

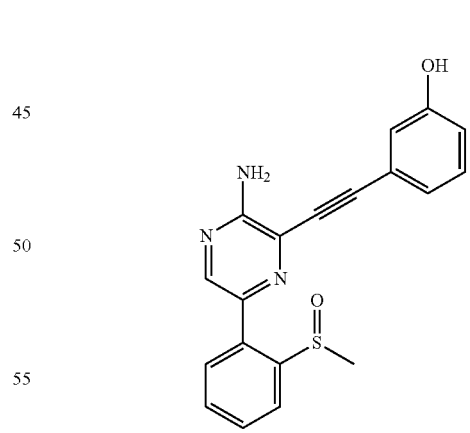

3-[2-(3-Amino-6-bromo-pyrazin-2-yl)ethynyl]phenol (72 mg, 0.2482 mmol), (2-methylsulfinylphenyl)boronic acid (54.80 mg, 0.2978 mmol) and K$_3$PO$_4$ (105.4 mg, 0.4964 mmol) were combined in MeCN (2 mL)/water and Pd [P($^t$Bu)$_3$]$_2$ (6.342 mg, 0.01241 mmol) was added. The reaction was heated at 60° C. for 15 hours. The reaction was cooled to ambient temperature and diluted with EtOAc and 1M HCl. The layers were separated and the aqueous layer extracted with EtOAc (×3). The combined organic layers were dried (MgSO$_4$), filtered and concentrated in vacuo. The residue was purified by column chromatography (ISCO Companion™, 12 g column, eluting with 0 to 100% EtOAc/Petroleum Ether, dry loaded) and freeze-dried to give the title product as a yellow solid (24 mg, 26% Yield). $^1$H NMR (400.0 MHz, DMSO) δ 3.34 (s, 3H), 5.15 (d, 1H), 6.88 (dd, 1H), 7.09 (br s, 2H), 7.19 (d, 1H), 7.27 (t, 1H), 7.60-7.69 (m, 2H), 7.89 (d, 1H), 8.17 (d, 1H), 8.60 (s, 1H) and 9.76 (s, 1H) ppm; MS (ES$^+$) 350.1.

The following compound was also prepared using a sequence similar to that outlined in Method D:

Compound I-18: 2-[5-Amino-6-[2-(3-hydroxyphenyl)ethynyl]pyrazin-2-yl]benzonitrile $^1$H NMR (400.0 MHz, DMSO) δ 6.89 (dd, 1H), 7.12 (d, 1H), 7.14 (br s, 2H), 7.18 (d, 1H), 7.25 (t, 1H), 7.59 (dt, 1H), 7.79 (dt, 1H), 7.85 (d, 1H), 7.94 (d, 1H), 8.46 (s, 1H) and 9.77 (s, 1H) ppm; MS (ES$^+$) 313.1.

Example 5

5-[5-Amino-6-[2-(3-hydroxyphenyl)ethynyl]pyrazin-2-yl]-1-isopropyl-pyridin-2-one (Compound I-16)

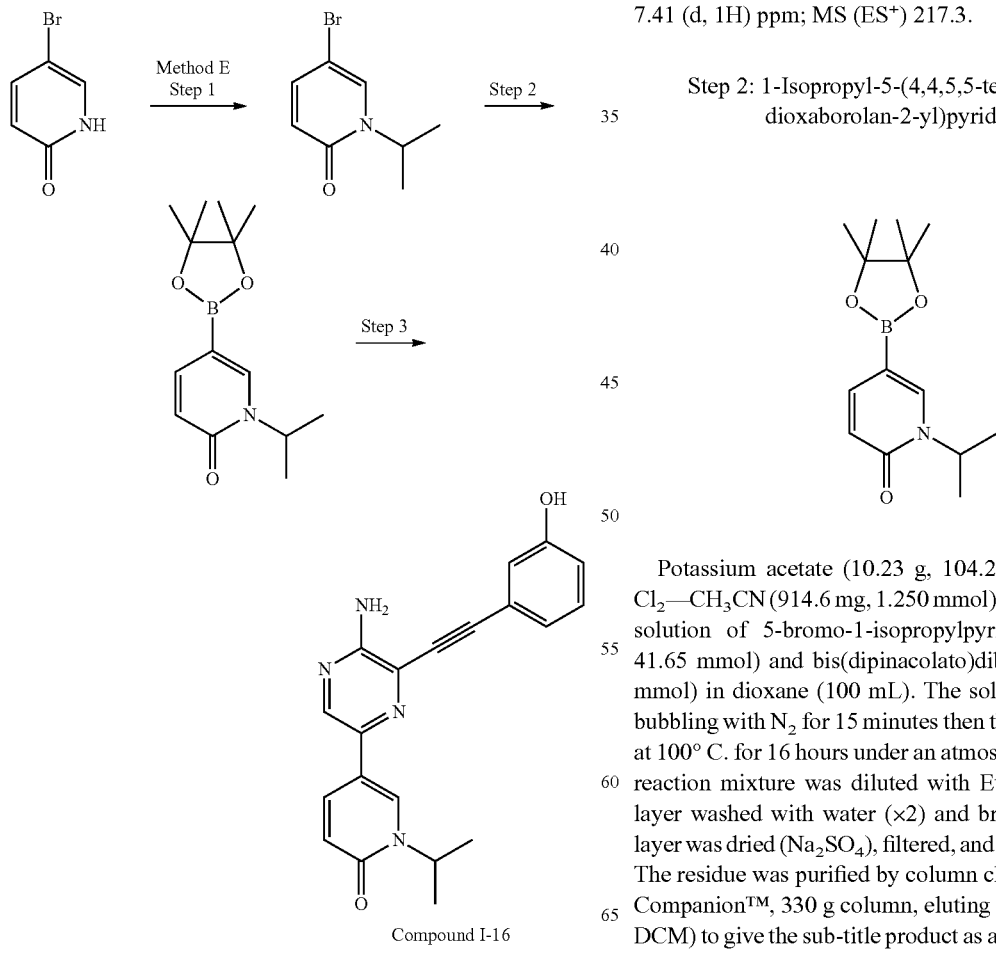

Compound I-16

Method E

Step 1: 5-Bromo-1-isopropylpyridin-2(1H)-one

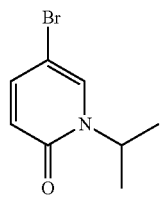

Potassium tert-butoxide (16.80 g, 18.63 mL, 142.2 mmol) was added to a suspension of 5-bromo-1H-pyridin-2-one (25 g, 142.2 mmol) in DME (247.5 mL) and the mixture stirred at ambient temperature for 30 minutes. To the mixture was added potassium carbonate (13.76 g, 99.54 mmol) and 2-bromopropane (34.98 g, 26.70 mL, 284.4 mmol) and the reaction mixture heated at reflux for 64 hours. The reaction mixture was filtered to remove the resultant precipitate and the filtrate concentrated in vacuo. The residue was recrystalised from DCM/hexane to give the sub-title product as an off-white solid (19.1 g 62% Yield). $^1$H NMR (400.0 MHz, CDCl$_3$) δ 1.36 (d, 6H), 5.22 (dt, 1H), 6.49 (d, 1H), 7.31 (dd, 1H) and 7.41 (d, 1H) ppm; MS (ES$^+$) 217.3.

Step 2: 1-Isopropyl-5-(4,4,5,5-tetramethyl-1,3,2-dioxaborolan-2-yl)pyridin-2-one Potassium acetate (10.23 g, 104.2 mmol) and Pd(dppf)Cl$_2$—CH$_3$CN (914.6 mg, 1.250 mmol) were added to a stirred solution of 5-bromo-1-isopropylpyridin-2(1H)-one (9 g, 41.65 mmol) and bis(dipinacolato)diboron (15.87 g, 62.50 mmol) in dioxane (100 mL). The solvent was degassed by bubbling with N$_2$ for 15 minutes then the reaction was heated at 100° C. for 16 hours under an atmosphere of nitrogen. The reaction mixture was diluted with EtOAc and the organic layer washed with water (×2) and brine (×1). The organic layer was dried (Na$_2$SO$_4$), filtered, and concentrated in vacuo. The residue was purified by column chromatography (ISCO Companion™, 330 g column, eluting with 5 to 60% EtOAc/DCM) to give the sub-title product as a light orange solid (7.9 g, 72% Yield). $^1$H NMR (400.0 MHz, CDCl$_3$) δ 1.31 (s, 12H), 1.39 (d, 6H), 5.26 (hept, 1H), 6.52 (d, 1H), 7.56 (dd, 1H) and 7.78 (s, 1H) ppm; MS (ES+) 264.3.

Step 3: 5-[5-Amino-6-[2-(3-hydroxyphenyl)ethynyl]pyrazin-2-yl]-1-isopropyl-pyridin-2-one

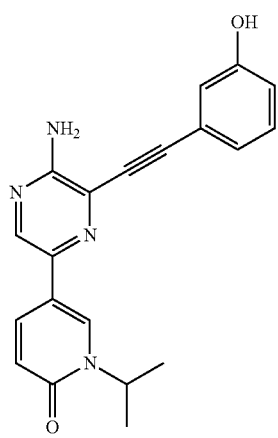 [SMILES: CC(C)n1cc(-c2cnc(N)c(C#Cc3cccc(O)c3)n2)ccc1=O]

3-[2-(3-Amino-6-bromo-pyrazin-2-yl)ethynyl]phenol (100 mg, 0.3447 mmol), 1-isopropyl-5-(4,4,5,5-tetramethyl-1,3,2-dioxaborolan-2-yl)pyridin-2-one (108.8 mg, 0.4136 mmol) and K₃PO₄ (146.3 mg, 0.6894 mmol) were combined in MeCN (2 mL)/water (0.5 mL) and Pd[P(ᵗBu)₃]₂ (8.811 mg, 0.01724 mmol) was added. The reaction was heated at 60° C. for 15 hours. The reaction was cooled to ambient temperature and diluted with EtOAc and 1M HCl. The layers were separated and the aqueous layer extracted with EtOAc (×3). The combined organic layers were dried (MgSO₄), filtered and concentrated in vacuo. The residue was purified by column chromatography (VARIAN 971-FP™, 8 g column, eluting with 0 to 10% MeOH/DCM, dry loaded) to give the title compound as a yellow solid (25.2 mg, 21% Yield). ¹H NMR (400.0 MHz, DMSO) δ 1.38 (d, 6H), 5.11 (sept, 1H), 6.49 (d, 1H), 6.77 (s, 2H), 6.87 (dd, 1H), 7.12 (s, 1H), 7.18 (d, 1H), 7.25 (t, 1H), 7.99 (dd, 1H), 8.20 (d, 1H), 8.55 (s, 1H) and 9.74 (s, 1H) ppm; MS (ES+) 347.1.

Example 6

1-[4-[5-Amino-6-[2-(3-hydroxyphenyl)ethynyl]pyrazin-2-yl]-3,6-dihydro-2H-pyridin-1-yl]propan-1-one (Compound I-30)

SCHEME VI

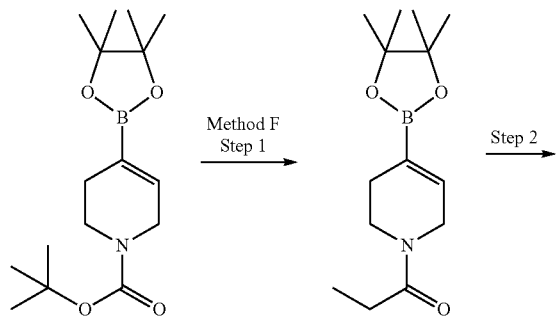

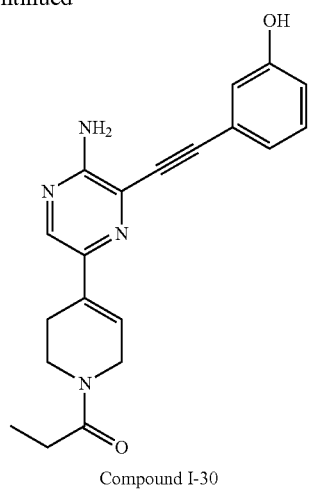

Compound I-30

Method F

Step 1: 1-[4-(4,4,5,5-Tetramethyl-1,3,2-dioxaborolan-2-yl)-3,6-dihydro-2H-pyridin-1-yl]propan-1-one

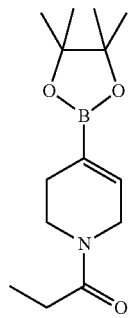 [SMILES: CCC(=O)N1CC=C(B2OC(C)(C)C(C)(C)O2)CC1]

TFA (14.75 g, 9.966 mL, 129.4 mmol) was added to a stirred solution of tert-butyl 4-(4,4,5,5-tetramethyl-1,3,2-dioxaborolan-2-yl)-3,6-dihydro-2H-pyridine-1-carboxylate (5000 mg, 16.17 mmol) in DCM (40 mL) at 0° C. and the reaction stirred at this temperature for 1.5 hours. The solvent was removed in vacuo and the residue azeotroped with MeCN (×3). The residue was re-dissolved in DCM (50 mL) and cooled to 0° C. Et₃N (6.545 g, 9.015 mL, 64.68 mmol) was added followed by a solution of propionyl chloride (1.646 g, 1.546 mL, 17.79 mmol) in DCM (5 mL). The reaction mixture was allowed to warm to ambient temperature over 1 hour. The mixture was diluted with DCM and washed with 1:1 1M HCl/brine (×2), dried (Na₂SO₄), filtered and concentrated in vacuo. The residue was purified by column chromatography (ISCO Companion™, 120 g column, eluting with 20 to 80% EtOAc/Petroleum Ether) to give the sub-title product as a white solid (3.87 g, 90% Yield). ¹H NMR (400.0 MHz, CDCl₃) δ 1.15 (t, 3H), 1.27 (s, 12H), 2.20-2.44 (m, 4H), 3.47 (t, 1H), 3.64 (s, 1H), 4.06 (d, 2H) and 6.48 (d, 1H) ppm; MS (ES+) 266.3.

Step 2: 1-[4-[5-Amino-6-[2-(3-hydroxyphenyl)ethy-nyl]pyrazin-2-yl]-3,6-dihydro-2H-pyridin-1-yl]pro-pan-1-one

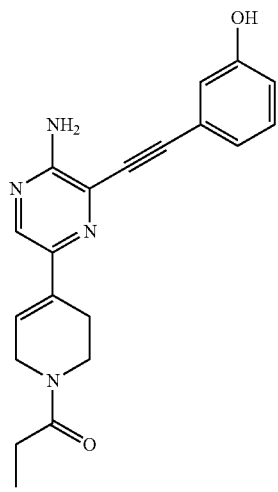 [SMILES: CCC(=O)N1CC=C(c2cnc(N)c(C#Cc3cccc(O)c3)n2)CC1]

3-[2-(3-Amino-6-bromo-pyrazin-2-yl)ethynyl]phe-nol (100 mg, 0.3447 mmol), 1-[4-(4,4,5,5-tetram-ethyl-1,3,2-dioxaborolan-2-yl)-3,6-dihydro-2H-pyri-din-1-yl]propan-1-one (109.7 mg, 0.4136 mmol) and $K_3PO_4$ (146.3 mg, 0.6894 mmol) were combined in MeCN (2 mL)/water (0.5 mL) and $Pd[P(tBu)_3]_2$ (8.811 mg, 0.01724 mmol) was added. The reaction was heated at 60° C. for 15 hours. The reaction was cooled to ambient temperature and diluted with EtOAc and 1M HCl. The layers were separated and the aqueous layer extracted with EtOAc (×3). The combined organic layers were dried ($MgSO_4$), filtered and concentrated in vacuo. The residue was purified by column chromatography (VARIAN 971-FP™, 8 g column, eluting with 0 to 10% MeOH/DCM, dry loaded) to give the title compound as a yellow solid (43 mg, 35% Yield). $^1$H NMR (400.0 MHz, DMSO) δ 1.03 (t, 3H), 1.29 (d, 2H), 2.32-2.43 (m, 2H), 3.60-3.67 (m, 2H), 4.14 (d, 2H), 6.47 (s, 1H), 6.74 (s, 2H), 6.86 (dd, 1H), 7.09 (s, 1H), 7.15 (d, 1H), 7.24 (t, 1H), 8.21 (s, 1H) and 9.74 (s, 1H) ppm; MS (ES$^+$) 349.1.

Example 7

3-[2-[3-Amino-6-(4-tetrahydropyran-4-ylsulfo-nylphenyl)pyrazin-2-yl]ethynyl]phenol (Compound I-34)

SCHEME VII

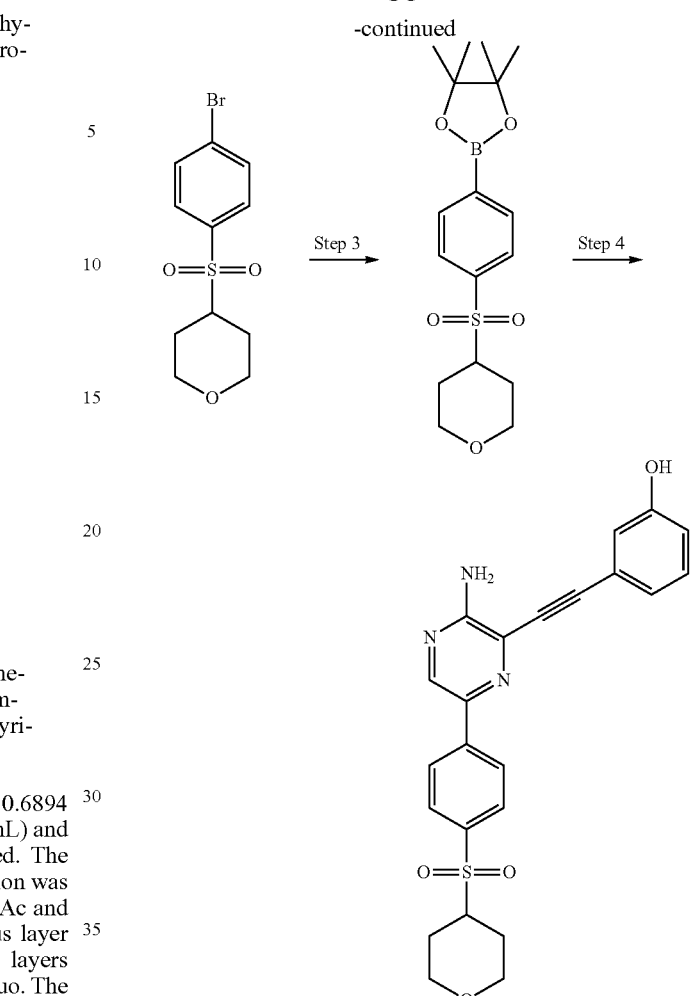

Compound I-34

Method G

Step 1: 4-(4-Bromophenyl)sulfanyltetrahydropyran

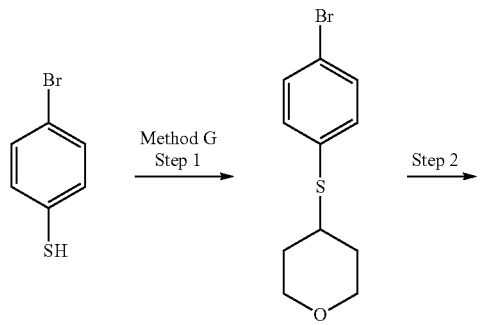

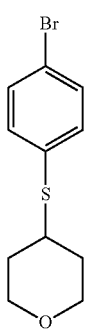

4-Iodotetrahydropyran (9 g, 42.45 mmol) was added to a stirred suspension of 4-bromobenzenethiol (7.296 g, 38.59 mmol) and potassium carbonate (10.67 g, 77.18 mmol) in DMF (15 mL) and the reaction stirred at ambient temperature for 3 hours. The mixture was diluted with $Et_2O$ and washed with water (×2) and brine (×1). The organic extracts was dried (MgSO$_4$) and concentrated in vacuo. Petroleum ether was added to the residue and the resultant precipitate removed by filtration. The filtrate was concentrated in vacuo to give the sub-title compound as a light yellow oil (9.0 g, 85% Yield). $^1$H NMR (400.0 MHz, CDCl$_3$) δ 1.63-1.73 (m, 2H), 1.89-1.93 (m, 2H), 3.23-3.30 (m, 1H), 3.45 (td, 2H), 3.99 (dt, 2H), 7.31 (d, 2H) and 7.45 (d, 2H) ppm.

Step 2: 4-(4-Bromophenyl)sulfonyltetrahydropyran

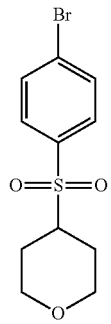

4-(4-Bromophenyl)sulfanyltetrahydropyran (9 g, 32.94 mmol) was dissolved in DCM (150 mL) and cooled to 0° C. mCPBA (14.21 g, 82.35 mmol) was added in portions over 15 minutes and the reaction mixture allowed to stir at 0° C. for 30 minutes then warmed to ambient temperature for 1 hour. The reaction was quenched by the addition of 50/50 saturated aqueous NaHCO$_3$/saturated aqueous Na$_2$S$_2$O$_4$ (50 mL) and stirred for 10 minutes. The organic layer was separated and washed with saturated aqueous NaHCO$_3$ (×2), water (×1) and brine (×1). The organic extracts were dried (MgSO4), filtered and concentrated in vacuo to give the sub-title compound as a white solid (9.05 g, 90% Yield). $^1$H NMR (400.0 MHz, CDCl$_3$) δ 1.80 (qd, 2H), 1.90-1.94 (m, 2H), 3.15 (tt, 1H), 3.34 (dt, 2H), 4.08 (dd, 2H) and 7.76 (4H, s) ppm.

Step 3: 4,4,5,5-Tetramethyl-2-(4-tetrahydropyran-4-ylsulfonylphenyl)-1,3,2-dioxaborolane

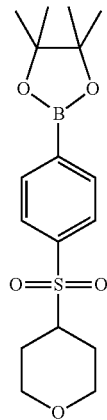

4-(4-Bromophenyl)sulfonyltetrahydropyran (10 g, 32.77 mmol) was dissolved in dioxane (179.2 mL) and bis(pinacolato)diboron (12.52 g, 49.32 mmol) and potassium acetate (9.681 g, 98.64 mmol) were added. The reaction was degassed and filled with nitrogen five times then Pd(dppf)Cl$_2$.DCM (2.676 g, 3.277 mmol) was added and the reaction heated to 90° C. for 2 hours. The reaction mixture was cooled to ambient temperature and diluted with DCM and water and the layers separated. The aqueous layer was extracted with DCM (×3) and the combined organic extracts washed with water (×1) and brine (×1), dried (MgSO$_4$) and concentrated in vacuo. The residue was passed through a pad of Fluorosil eluting with 30% EtOAc/Petroleum ether and the product containing fractions were combined and concentrated in vacuo to give the sub-title compound as a light brown solid (10.8 g 94% Yield). $^1$H NMR (400.0 MHz, CDCl$_3$) δ 1.4 (9H, s), 1.78-1.92 (4H, m), 3.1-3.2 (1H, m), 3.32 (2H, t), 4.02-4.1 (2H, m), 7.87 (2H, d) and 8.02 (2H, d) ppm.

Step 4: 3-[2-[3-Amino-6-(4-tetrahydropyran-4-ylsulfonylphenyl)pyrazin-2-yl]ethynyl]phenol

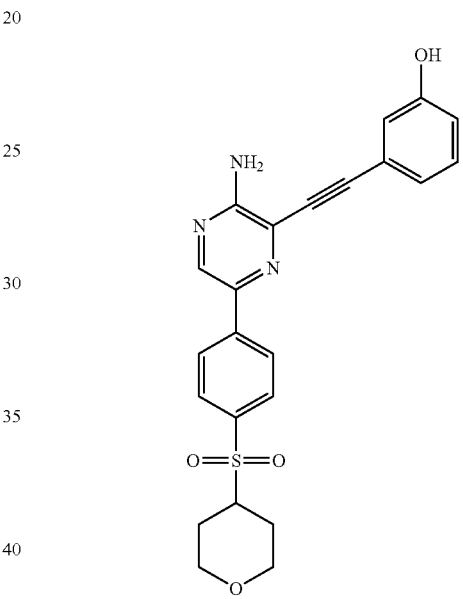

3-[2-(3-Amino-6-bromo-pyrazin-2-yl)ethynyl]phenol (50 mg, 0.1723 mmol), 4,4,5,5-tetramethyl-2-(4-tetrahydropyran-4-ylsulfonylphenyl)-1,3,2-dioxaborolane (85.70 mg, 0.2068 mmol) and K$_3$PO$_4$ (73.15 mg, 0.3446 mmol) were combined in MeCN (2 mL)/water (0.5 mL) and Pd[P($^t$Bu)$_3$]$_2$ (4.403 mg, 0.008615 mmol) was added. The reaction was heated at 60° C. for 15 hours. The reaction was cooled to ambient temperature and diluted with EtOAc and 1M HCl. The layers were separated and the aqueous layer extracted with EtOAc (×3). The combined organic layers were dried (MgSO$_4$), filtered and concentrated in vacuo. The residue was purified by column chromatography (ISCO Companion™, 12 g column, eluting with 0 to 100% EtOAc/Petroleum Ether, dry loaded) followed by purification by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The fractions were collected and freeze-dried to give the title compound as a yellow solid (14 mg, 17% Yield). $^1$H NMR (400.0 MHz, DMSO) δ 1.30-1.41 (m, 2H), 1.56 (d, 2H), 3.07-3.12 (m, 2H), 3.34-3.40 (m, 2H), 3.71 (dd, J=3.9, 11.4 Hz, 1H), 6.67-6.70 (m, 1H), 6.94 (br s, 2H), 6.95 (d, 1H), 7.01 (d, 1H), 7.07 (t, 1H), 7.70 (d, 2H), 8.05 (d, 2H), 8.55 (s, 1H) and 9.57 (s, 1H) ppm; MS (ES$^+$) 436.1.

Example 8

3-[2-[3-Amino-6-[4-(4-piperidylsulfonyl)phenyl]pyrazin-2-yl]ethynyl]phenol (Compound I-17)

SCHEME VIII

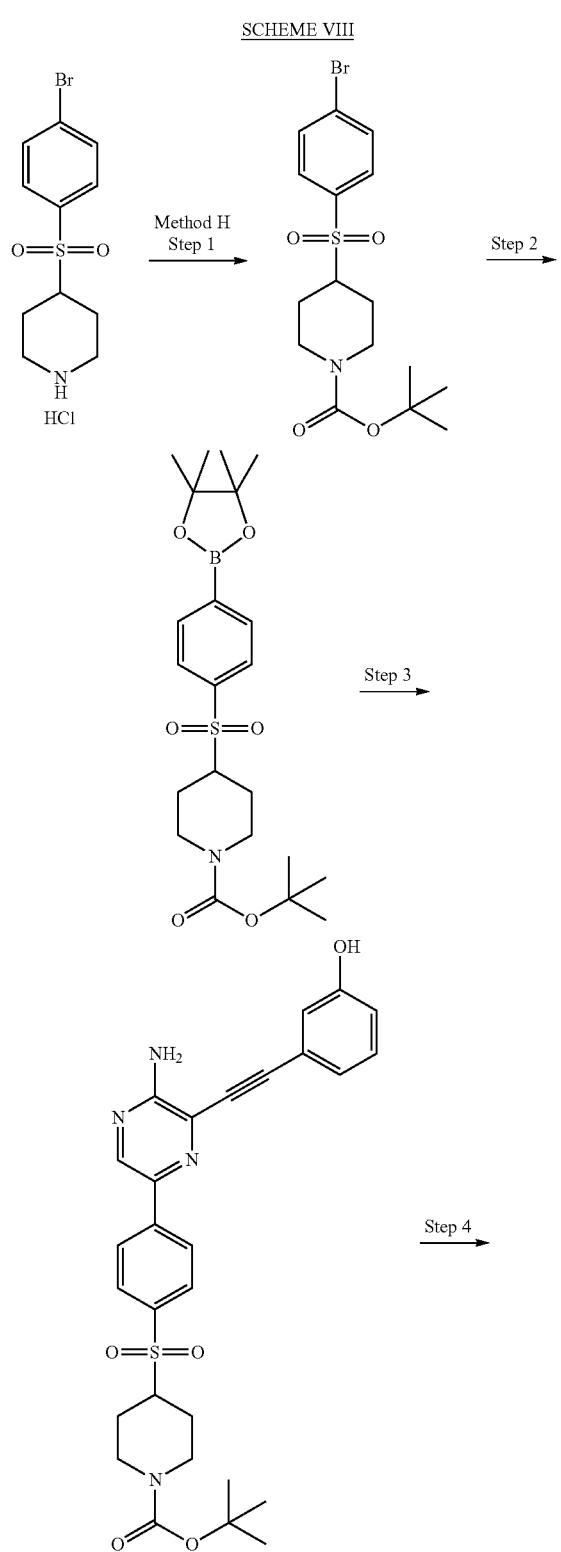

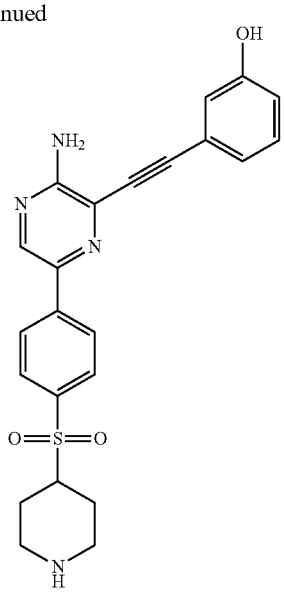

Method H

Step 1: tert-Butyl 4-(4-bromophenyl)sulfonylpiperidine-1-carboxylate

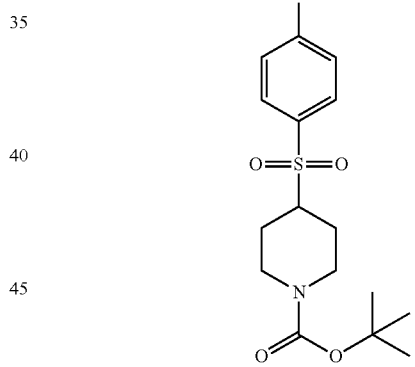

tert-Butoxycarbonyl tert-butyl carbonate (260.8 mg, 274.5 μL, 1.195 mmol) was added to a stirred suspension of 4-(4-bromophenyl)sulfonylpiperidine hydrochloride (370 mg, 1.086 mmol) and Et$_3$N (241.7 mg, 332.9 μL, 2.389 mmol) in DCM (10 mL) and the reaction mixture stirred at ambient temperature for 16 hours. The reaction mixture was washed in a 150 mL phase separation cartridge with saturated aqueous NaHCO$_3$ (×2) and brine (×1) and the organic extract dried (MgSO$_4$), filtered and concentrated in vacuo. The residue was purified by column chromatography (ISCO Companion™, 40 g column, eluting with 0 to 50% EtOAc/Petroleum Ether, loaded in DCM) to give the sub-title product as a colourless oil which crystallizes on standing to a white solid (375 mg, 85% Yield). $^1$H NMR (400.0 MHz, DMSO) δ 1.29 (dd, 2H), 1.37 (s, 9H), 1.83 (d, 2H), 2.73 (br s, 2H), 3.51-3.56 (m, 1H), 4.00 (br d, 2H), 7.78 (d, 2H) and 7.91 (d, 2H) ppm; MS (ES$^+$) 350.0.

Step 2: tert-Butyl 4-[4-(4,4,5,5-tetramethyl-1,3,2-dioxaborolan-2-yl)phenyl]sulfonylpiperidine-1-carboxylate

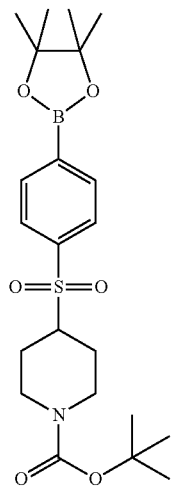 [SMILES: CC(C)(C)OC(=O)N1CCC(S(=O)(=O)c2ccc(B3OC(C)(C)C(C)(C)O3)cc2)CC1]

A mixture of tert-butyl 4-(4-bromophenyl)sulfonylpiperidine-1-carboxylate (374 mg, 0.9250 mmol), bis(pinocalato)diboron (281.9 mg, 1.110 mmol) and potassium acetate (272.3 mg, 2.775 mmol) in dioxane (5 mL) was degassed and placed under an atmosphere of nitrogen. Pd(dppf)Cl$_2$DCM (37.77 mg, 0.04625 mmol) was added in one portion and the reaction mixture heated at 95° C. for 15 hours. The reaction was cooled to ambient temperature and diluted with EtOAc/brine. The layers were separated and the aqueous layer extracted with EtOAc (×3). The combined organic extracts were dried (MgSO$_4$), filtered and concentrated in vacuo. The crude residue was passed through a pad of Fluorsil and eluted with 50% EtOAc/Petrol to give the sub-title compound as a white solid (399 mg, 96% Yield). $^1$H NMR (400.0 MHz, DMSO) δ 1.31 (d, 12H), 1.28-1.33 (m, 2H), 1.36 (s, 9H), 1.81 (br d, 2H), 2.68 (br s, 2H), 3.46-3.52 (m, 1H), 3.94-4.06 (m, 2H), 7.85 (d, 2H) and 7.94 (d, 2H) ppm; MS (ES$^+$) 314.1.

Step 3: tert-Butyl 4-[4-[5-amino-6-[2-(3-hydroxyphenyl)ethynyl]pyrazin-2-yl]phenyl]sulfonylpiperidine-1-carboxylate

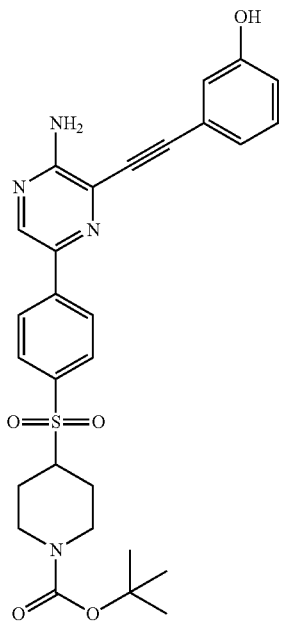 [SMILES: CC(C)(C)OC(=O)N1CCC(S(=O)(=O)c2ccc(-c3cnc(N)c(C#Cc4cccc(O)c4)n3)cc2)CC1]

3-[2-(3-Amino-6-bromo-pyrazin-2-yl)ethynyl]phenol (100 mg, 0.3447 mmol), tert-butyl 4-[4-(4,4,5,5-tetramethyl-1,3,2-dioxaborolan-2-yl)phenyl]sulfonylpiperidine-1-carboxylate (186.7 mg, 0.4136 mmol) and K$_3$PO$_4$ (146.3 mg, 0.6894 mmol) were combined in MeCN (2 mL)/water (0.5 mL) and Pd[P($^t$Bu)$_3$]$_2$ (8.811 mg, 0.01724 mmol) was added. The reaction was heated at 60° C. for 15 hours. The reaction was cooled to ambient temperature and diluted with EtOAc and 1M HCl. The layers were separated and the aqueous layer extracted with EtOAc (×3). The combined organic layers were dried (MgSO$_4$), filtered and concentrated in vacuo. The material was used directly in the next step without further purification.

Step 4: 3-[2-[3-Amino-6-[4-(4-piperidylsulfonyl)phenyl]pyrazin-2-yl]ethynyl]phenol

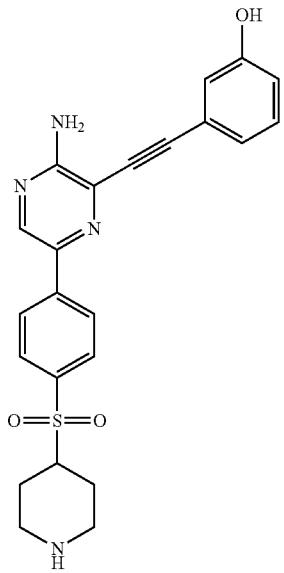 [SMILES: Nc1ncc(-c2ccc(S(=O)(=O)C3CCNCC3)cc2)nc1C#Cc1cccc(O)c1]

Crude tert-butyl 4-[4-[5-amino-6-[2-(3-hydroxyphenyl)ethynyl]pyrazin-2-yl]phenyl]sulfonylpiperidine-1-carboxylate (184.3 mg, 0.3447 mmol—assumed quantitative yield from Step 3) was dissolved in DCM (5 mL) and TFA (1 mL, 12.98 mmol) was added. The reaction mixture was stirred at ambient temperature for 4 hours. The solvent was removed in vacuo and the residue azeotroped with DCM (×2) and ether (×2). The material was purified by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The fractions were collected and freeze-dried to give the mono-TFA salt of the title compound as a yellow solid (10.3 mg, 5% Yield). $^1$H NMR (400.0 MHz, DMSO) δ 1.65-1.74 (m, 2H), 2.06 (d, 2H), 2.85-2.90 (m, 2H), 3.36 (d, 2H), 3.59-3.65 (m, 1H), 6.89 (dd, 1H), 7.14-7.21 (m, 2H), 7.27 (t, 1H), 7.90 (d, 2H), 8.23 (br s, 1H), 8.28 (d, 2H), 8.54 (br s, 1H), 8.77 (s, 1H) and 9.78 (s, 1H) ppm; MS (ES$^+$) 435.1.

Example 9

3-Ethynyl-5-(4-isopropylsulfonylphenyl)pyrazin-2-amine (Compound I-5)

SCHEME IX

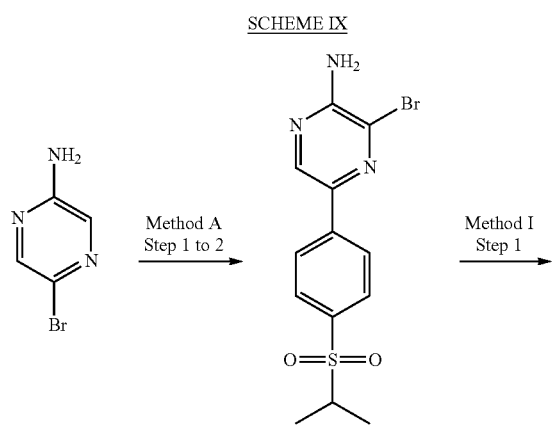

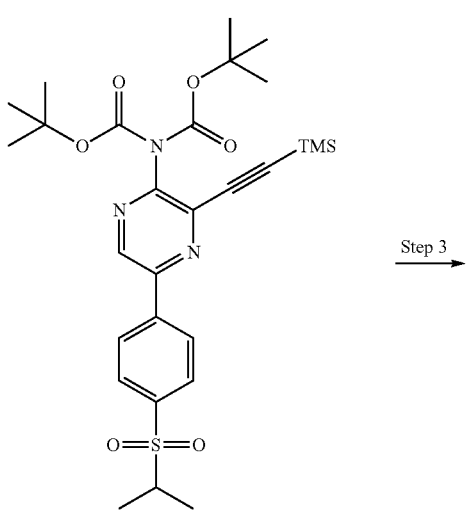

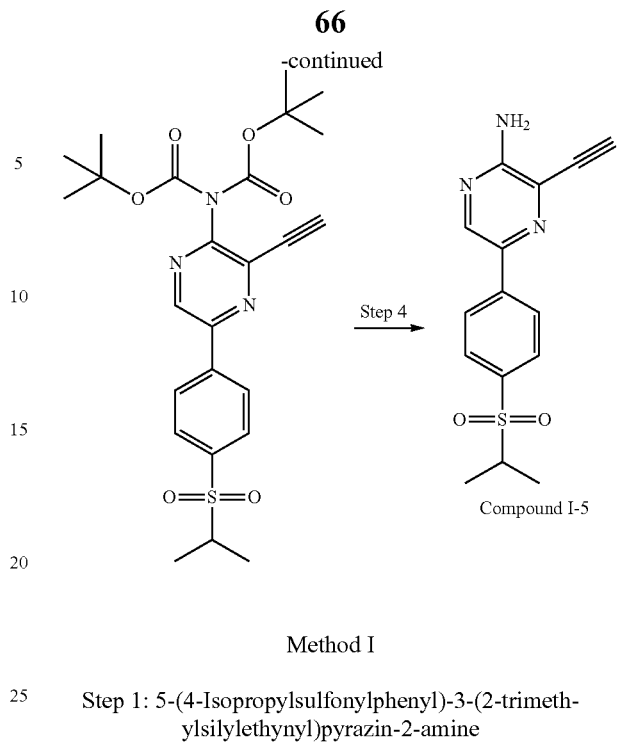

Method I

Step 1: 5-(4-Isopropylsulfonylphenyl)-3-(2-trimethylsilylethynyl)pyrazin-2-amine

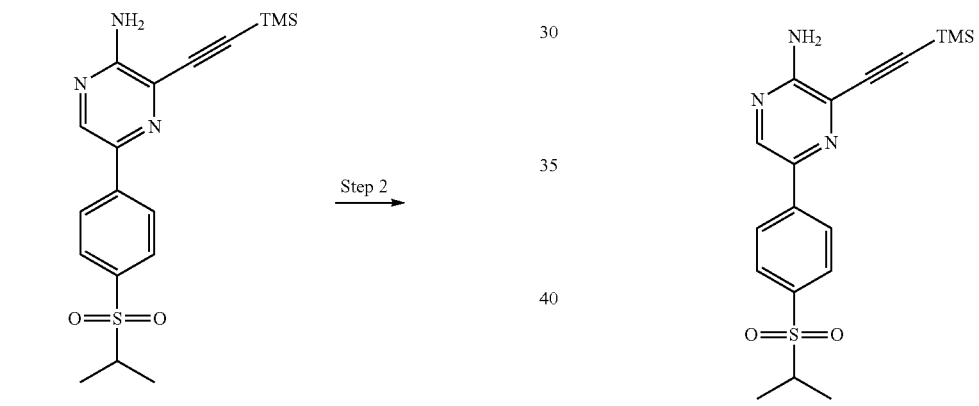

Triethylamine (47.58 g, 65.54 mL, 470.2 mmol) was added to a stirred suspension of 3-bromo-5-(4-isopropylsulfonylphenyl)pyrazin-2-amine (33.5 g, 94.04 mmol) in anhydrous DMF (234.5 mL). Copper(I) iodide (2.148 g, 11.28 mmol) was then added followed by Pd(PPh$_3$)$_4$ (5.433 g, 4.702 mmol). The stirred mixture was cooled to 0° C. in an ice-bath and (trimethylsilyl)acetylene (12.01 g, 17.28 mL, 122.3 mmol) was added dropwise over 10 minutes. The ice bath was then removed and the mixture allowed to warm to ambient temperature over 2 hours. The mixture was poured into EtOAc/water (500 mL/300 mL) and the mixture was filtered through a pad of celite. The organic phase was separated and the aqueous layer extracted with EtOAc. The combined organics were washed with water (×1) and brine (×1), dried (MgSO$_4$), filtered and concentrated in vacuo. The residue was purified by column chromatography (ISCO Companion™, 750 g column, eluting with 0 to 15% DCM/EtOAc, dry-loaded) to give the sub-title product as a dark yellow solid (28.0 g, 78% Yield). $^1$H NMR (400.0 MHz, DMSO) δ 0.15 (s, 9H), 1.03 (d, 6H), 3.29 (sept, 1H), 6.80 (br s, 2H), 7.74 (d, 2H), 8.05 (d, 2H) and 8.60 (s, 1H) ppm; MS (ES$^+$) 375.1.

Step 2: tert-Butyl N-tert-butoxycarbonyl-N-[5-(4-isopropylsulfonylphenyl)-3-(2-trimethylsilylethynyl)pyrazin-2-yl]carbamate

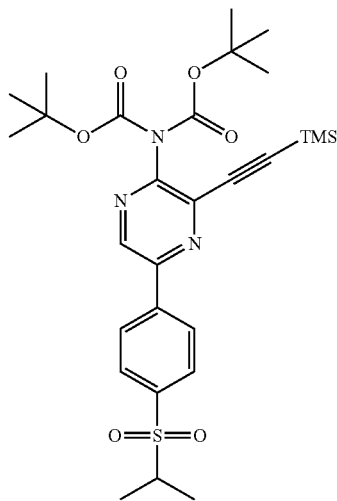 [SMILES: CC(C)S(=O)(=O)c1ccc(-c2cnc(N(C(=O)OC(C)(C)C)C(=O)OC(C)(C)C)c(C#C[Si](C)(C)C)n2)cc1]

Triethylamine (18.42 g, 25.37 mL, 182.0 mmol) was added to a stirred solution of 5-(4-isopropylsulfonylphenyl)-3-(2-trimethylsilylethynyl)pyrazin-2-amine (34 g, 91.02 mmol) in DCM (1.020 L). DMAP (1.112 g, 9.102 mmol) was added followed by tert-butoxycarbonyl tert-butyl carbonate (59.60 g, 62.74 mL, 273.1 mmol) in portions. The reaction mixture was stirred at ambient temperature for 16 hours. The reaction mixture was poured into water (500 mL) and the organic layer separated. The organic layer was washed with brine (×1), dried (MgSO$_4$), filtered and concentrated in vacuo. The residue was purified by silica gel chromatography eluting with 20-30% EtAOc/Petroleum Ether to give the sub-title product as an orange foam (42.6 g, 82% Yield). $^1$H NMR (400.0 MHz, CDCl$_3$) δ 0.15 (s, 9H), 1.19 (d, 6H), 1.28 (s, 18H), 3.10 (sept, 1H), 7.89 (d, 2H), 8.12 (d, 2H) and 8.75 (s, 1H) ppm; MS (ES$^+$) 574.1.

Step 3: tert-Butyl N-tert-butoxycarbonyl-N-[3-ethynyl-5-(4-isopropylsulfonylphenyl)pyrazin-2-yl]carbamate

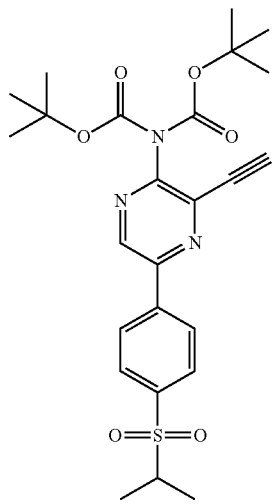 [SMILES: C#Cc1nc(-c2ccc(S(=O)(=O)C(C)C)cc2)cnc1N(C(=O)OC(C)(C)C)C(=O)OC(C)(C)C]

tert-Butyl N-tert-butoxycarbonyl-N-[5-(4-isopropylsulfonylphenyl)-3-(2-trimethylsilylethynyl)pyrazin-2-yl]carbamate (42.6 g, 74.25 mmol) was dissolved/suspended in methanol (510 mL) and 2M aqueous sodium carbonate (425.8 mL, 851.6 mmol) was added to the rapidly stirred mixture. An oil separated out and more methanol (100 mL) was added to dissolve. The mixture was stirred at ambient temperature for 1 hour. The slurry was poured into a mixture of EtOAc/water (800 mL/1 L). The organic phase was separated and the aqueous extracted with EtOAc (2×250 mL). The combined organic extracts were washed with brine, dried (MgSO$_4$), filtered and concentrated in vacuo. The residue was slurried in 5% EtOAc/Petrololeum Ether and stirred for 90 minutes at ambient temperature. The precipitate was isolated by filtration, washed with Petroleum Ether and dried to give the sub-title product as a white solid (33.1 g, 89% Yield). 1.18 (d, 6H), 1.37 (s, 18H), 3.50 (sept, 1H), 4.99 (s, 1H), 8.03 (d, 2H), 8.44 (d, 2H) and 9.35 (s, 1H) ppm; MS (ES$^+$) 502.1.

Step 4: 3-Ethynyl-5-(4-isopropylsulfonylphenyl)pyrazin-2-amine

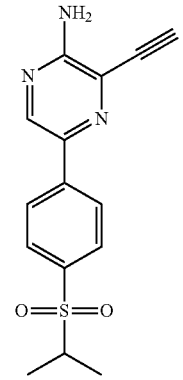 [SMILES: C#Cc1nc(-c2ccc(S(=O)(=O)C(C)C)cc2)cnc1N]

TFA (34.45 g, 23.28 mL, 302.1 mmol) was added to a stirred solution of tert-butyl N-tert-butoxycarbonyl-N-[3-ethynyl-5-(4-isopropylsulfonylphenyl)pyrazin-2-yl]carbamate (5 g, 9.968 mmol) in DCM (200 mL) and the reaction mixture stirred at ambient temperature for 1.5 hours. The solvent was removed in vacuo and the residue re-dissolved in DCM and stirred with saturated aqueous NaHCO$_3$ for 30 minutes. The layers were separated and the organic layer washed with saturated aqueous NaHCO$_3$ (×3). The combined aqueous layers were extracted with DCM (×3) and the combined organic extracts dried (MgSO$_4$), filtered and concentrated in vacuo. The residue was triturated from DCM and precipitate isolated by filtration and dried under vacuum to give the title product as a beige solid (2.8 g, 93% Yield). $^1$H NMR (400.0 MHz, DMSO) δ 1.18 (d, 6H), 3.44 (t, 1H), 4.76 (s, 1H), 7.01 (s, 2H), 7.89 (d, 2H), 8.20 (d, 2H) and 8.75 (s, 1H) ppm; MS (ES$^+$) 302.12.

Example 10

5-(4-Isopropylsulfonylphenyl)-3-[2-[3-(methylaminomethyl)phenyl]ethynyl]pyrazin-2-amine (Compound I-28)

SCHEME X

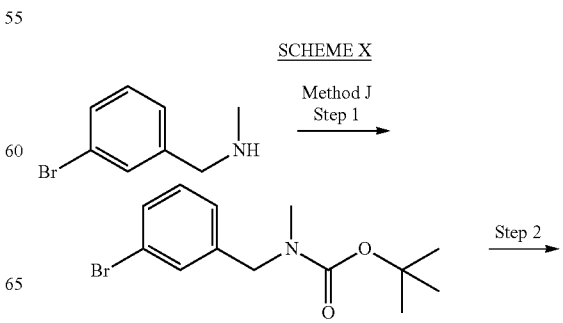

-continued

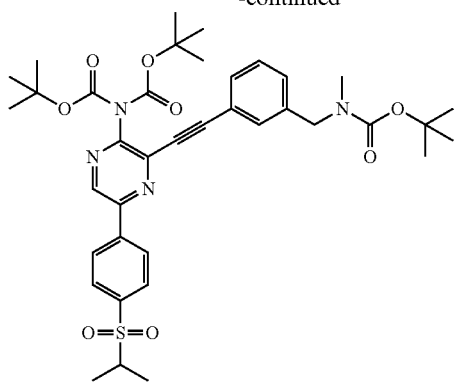

Step 3

Step 2: Di-tert-butyl 3-((3-((tert-butoxycarbonyl(methyl)amino)methyl)phenyl)ethynyl)-5-(4-(isopropylsulfonyl)phenyl)pyrazin-2-yliminodicarbonate

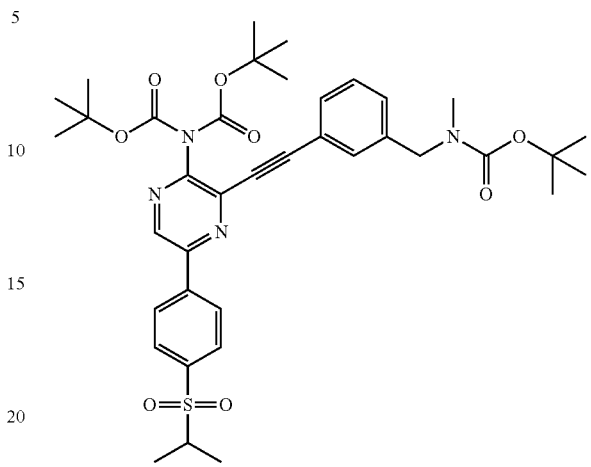

Triethylamine (234.1 mg, 322.5 μL, 2.313 mmol) was added to a stirred solution of tert-butyl N-[5-(4-(isopropylsulfonyl)phenyl)-3-ethynylpyrazin-2-yl]-N-tertbutoxycarbonyl-carbamate (116 mg, 0.2313 mmol), tert-butyl 3-bromobenzyl(methyl)carbamate (83.33 mg, 0.2776 mmol), copper (I) iodide (5.287 mg, 0.02776 mmol) and Pd(PPh$_3$)$_4$ (13.37 mg, 0.01157 mmol) in DMF (2 mL) and the reaction heated at 100° C. in a sealed tube for 1.5 hours. The reaction mixture was cooled to ambient temperature and diluted with EtOAc (20 mL) and 1 MHCl/brine (10 mL/10 mL). The layers were separated and the aqueous layer was extracted with EtOAc (2×20 mL). The combined organics extracts washed with brine (1×20 mL), dried over (MgSO$_4$) and concentrated in vacuo. The residue was purified by column chromatography (ISCO Companion™, 24 g column, eluting with 0 to 50% EtOAc/Petroleum Ether) to give the sub-title product as a yellow oil (60 mg, 36% Yield). $^1$H NMR (400.0 MHz, DMSO) δ 1.20 (d, 6H), 1.36-1.45 (2×s, 27H), 2.82 (s, 3H), 3.53 (sept, 1H), 4.43 (s, 2H), 7.39-7.41 (m, 1H), 7.46 (s, 1H), 7.53-7.55 (m, 2H), 8.06 (d, 2H), 8.48 (d, 2H) and 9.36 (s, 1H) ppm; MS (ES$^+$) 721.5.

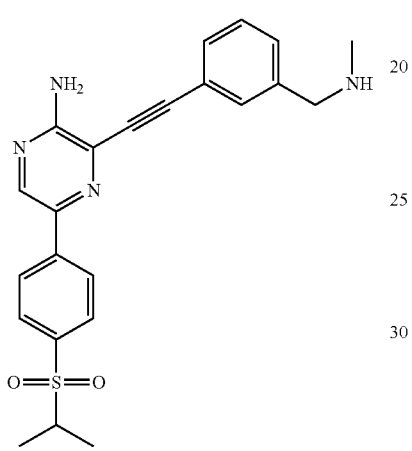

Compound I-28

Method J

Step 1: tert-Butyl 3-bromobenzyl(methyl)carbamate

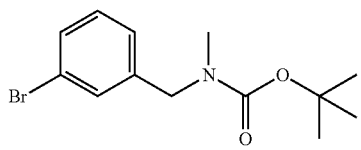 [SMILES: CN(Cc1cccc(Br)c1)C(=O)OC(C)(C)C]

BOC$_2$O (1.309 g, 1.378 mL, 5.998 mmol) was added to a stirred solution of 1-(3-bromophenyl)-N-methyl-methanamine (1 g, 4.998 mmol) and Et$_3$N (606.9 mg, 836.0 μL, 5.998 mmol) in DCM (20 mL) at ambient temperature and the reaction stirred for 16 hours. The reaction mixture was washed with 0.5M HCl (×1), water (×2) and brine (×1). The combined organic extracts were dried (MgSO$_4$), filtered and concentrated in vacuo. The residue was purified by column chromatography (ISCO Companion™, 40 g column, eluting with 0 to 50% EtOAc/Petroleum Ether) to give the sub-title product as a colourless oil (1.44 g, 96% Yield). $^1$H NMR (400.0 MHz, DMSO) d 1.38-1.43 (2×br s, 9H), 2.77 (s, 3H), 4.37 (s, 2H), 7.23 (d, 1H), 7.33 (t, 1H), 7.41 (s, 1H) and 7.48 (d, 1H) ppm; MS (ES$^+$) 302.1.

Step 3: 5-(4-Isopropylsulfonylphenyl)-3-[2-[3-(methylaminomethyl)phenyl]ethynyl]pyrazin-2-amine

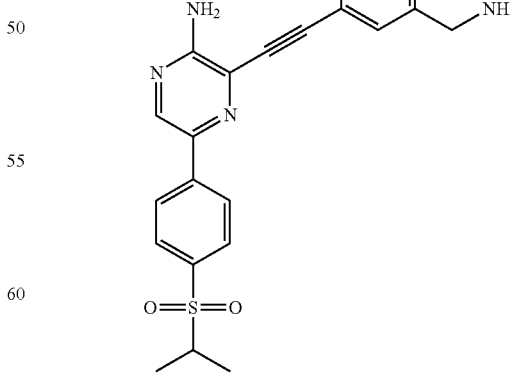

Di-tert-butyl 3-((3-((tert-butoxycarbonyl(methyl)amino) methyl)phenyl)ethynyl)-5-(4-(isopropylsulfonyl)phenyl) pyrazin-2-yliminodicarbonate (60 mg, 0.08323 mmol) was dissolved in DCM (5 mL) and TFA (379.6 mg, 256.5 μL, 3.329 mmol) was added. The reaction was allowed to stir at ambient temperature for 20 hours. The solvent was removed in vacuo and the residue azeotroped with DCM (×3). The residue was dissolved in EtOAc and washed with saturated aqueous NaHCO$_3$. The aqueous layer was extracted with EtOAc (×3) and the combined organic extracts dried (MgSO$_4$), filtered and concentrated in vacuo. The residue was purified by column chromatography (ISCO Companion™, 12 g column, eluting with 0 to 10% MeOH/DCM). The fractions were collected and freeze-dried to give the title compound as a yellow solid (6.5 mg, 18% Yield). $^1$H NMR (400.0 MHz, DMSO) δ 1.18 (d, 6H), 2.27 (s, 3H), 3.41-3.50 (m, 1H), 3.68 (s, 2H), 7.16 (br s, 2H), 7.41-7.42 (m, 2H), 7.64-7.66 (m, 1H), 7.75 (s, 1H), 7.90 (d, 2H), 8.24 (d, 2H) and 8.76 (s, 1H) ppm; MS (ES$^+$) 421.4.

Example 11

3-[2-[3-Amino-6-(4-isopropylsulfonylphenyl)pyrazin-2-yl]ethynyl]benzamide (Compound I-37)

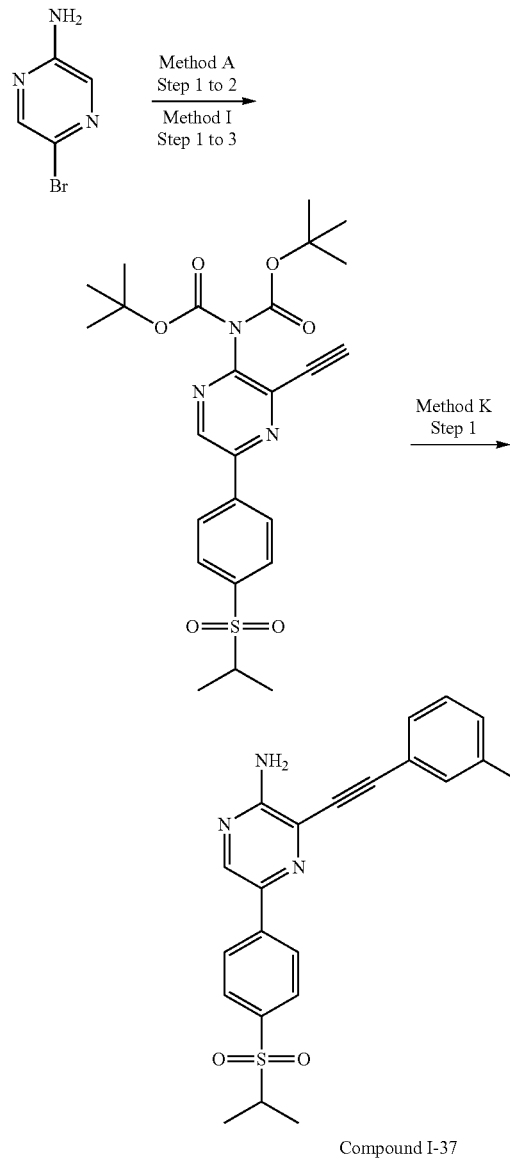

Compound I-37

Method K

Step 1: 3-[2-[3-Amino-6-(4-isopropylsulfonylphenyl)pyrazin-2-yl]ethynyl]benzamide Triethylamine (151.3 mg, 208.4 μL, 1.495 mmol) was added to a stirred solution of tert-butyl N-[5-(4-(isopropylsulfonyl)phenyl)-3-ethynylpyrazin-2-yl]-N-tertbutoxycarbonyl-carbamate (75 mg, 0.1495 mmol), 3-bromobenzamide (44.85 mg, 0.2242 mmol), copper (I) iodide (3.417 mg, 0.01794 mmol) and PdCl$_2$(PPh$_3$)$_2$ (5.247 mg, 0.007475 mmol) in DMF (1.5 mL) and the reaction was stirred at 120° C. for 5 minutes under fixed power (300 W) microwave conditions. The reaction mixture was cooled to ambient temperature and diluted with EtOAc and 1MHCl/brine (1:1). The layers were separated and the aqueous layer was extracted with ethyl acetate (×2). The combined organics extracts washed with brine (×2), dried over (MgSO$_4$) and concentrated in vacuo. The residue was dissolved in DCM (5 mL) and TFA (1 mL, 12.98 mmol) was added. The reaction was stirred at ambient temperature for 40 hours. The solvent was removed in vacuo and the residue azeotroped with DCM (×2) and ether (×2). The material was purified by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The fractions were collected, passed through a sodium bicarbonate cartridge and freeze-dried to give the title compound as a beige solid (11 mg, 17% Yield). $^1$H NMR (400.0 MHz, DMSO) δ 1.18 (d, 6H), 3.45 (sept, 1H), 7.22 (br s, 2H), 7.53 (br s, 1H), 7.57 (t, 1H), 7.91 (d, 2H), 7.94 (d, 2H), 8.10 (s, 1H), 8.24 (d, 2H), 8.29 (d, 1H) and 8.78 (s, 1H) ppm; MS (ES$^+$) 421.1.

Example 12

3-((6-aminopyridin-2-yl)ethynyl)-5-(4-(isopropylsulfonyl)phenyl)pyrazin-2-amine (Compound I-40)

SCHEME XII

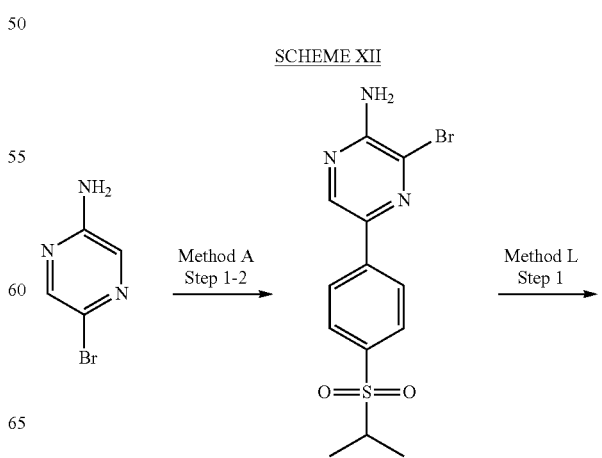

73
-continued

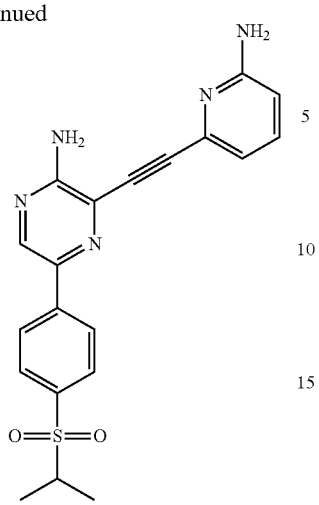

Method L

Step 1: 3-((6-aminopyridin-2-yl)ethynyl)-5-(4-(isopropylsulfonyl)phenyl)pyrazin-2-amine

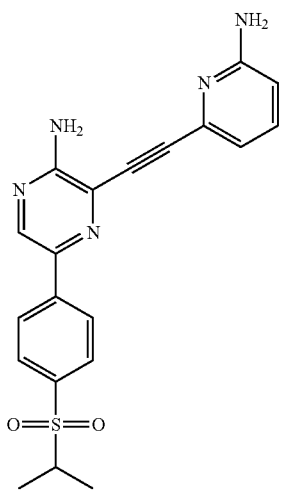 [SMILES: CC(C)S(=O)(=O)c1ccc(-c2cnc(N)c(C#Cc3cccc(N)n3)n2)cc1]

3-bromo-5-(4-(isopropylsulfonyl)phenyl)pyrazin-2-amine (75 mg, 0.2105 mmol), 6-ethynylpyridin-2-amine (29.84 mg, 0.2526 mmol), Pd EnCat 30 (33.68 mg, 0.01347 mmol) and DBU (70.50 mg, 69.25 µL, 0.4631 mmol) were combined in acetonitrile (1.500 mL). The reaction mixture was heated at 100° C. under microwave conditions for 1.5 hours. After this time the solid residue was removed by filtration and the filtrate concentrated in vacuo. The residue was purified by column chromatography (ISCO Companion™, 12 g column, eluting with 0 to 100% EtOAc/Petroleum Ether to 10% MeOH/DCM) to give the titled product as a beige solid (21 mg, 26% Yield). $^1$H NMR (400.0 MHz, DMSO) δ 1.18 (d, 6H), 3.45 (sept, 1H), 6.20 (s, 2H), 6.52 (d, 1H), 7.06 (d, 1H), 7.07 (br s, 2H), 7.45 (dd, 1H), 7.90 (d, 2H), 8.25 (d, 2H) and 8.78 (s, 1H) ppm; MS (ES$^+$) 394.1.

74

Example 13

2-amino-1-(4-((3-amino-6-(4-(isopropylsulfonyl)phenyl)pyrazin-2-yl)ethynyl)phenyl)ethanol (Compound I-41)

SCHEME XIII

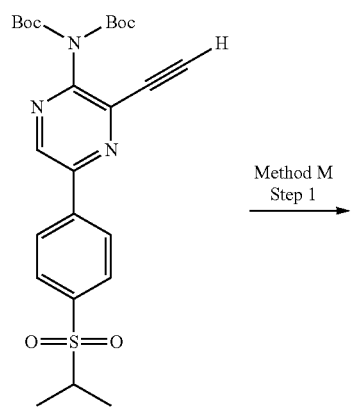

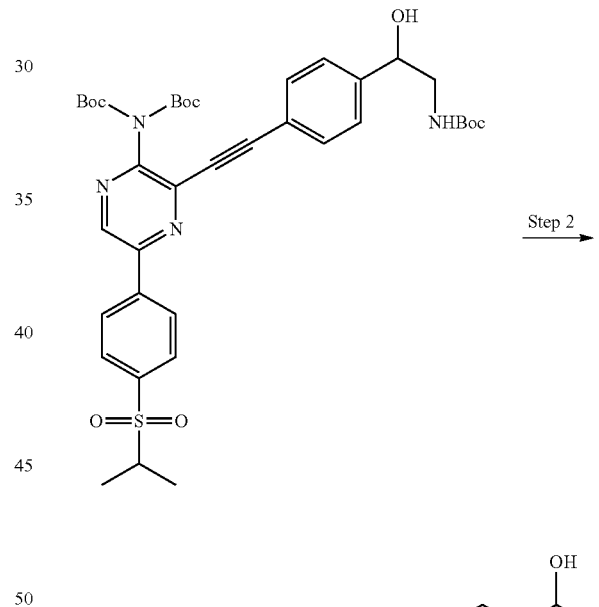

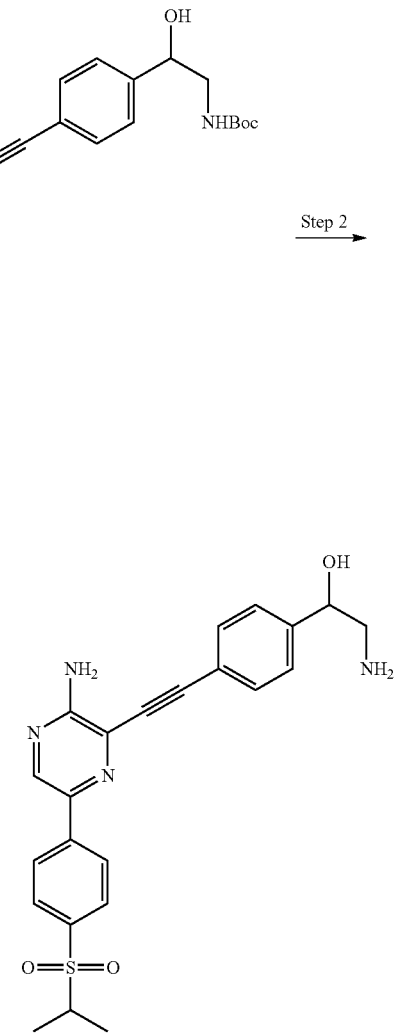

Method M

Step 1: tert-butyl tert-butoxycarbonyl (3-((4-(2-((tert-butoxycarbonyl)amino)-1-hydroxyethyl)phenyl)ethynyl)-5-(4-(isopropylsulfonyl)phenyl)pyrazin-2-yl)carbamate

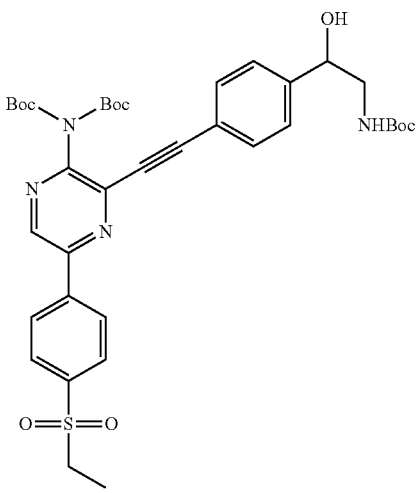 [SMILES: CCS(=O)(=O)c1ccc(-c2cnc(N(C(=O)OC(C)(C)C)C(=O)OC(C)(C)C)c(C#Cc3ccc(C(O)CNC(=O)OC(C)(C)C)cc3)n2)cc1]

Triethyl amine (302.6 mg, 416.8 μL, 2.990 mmol) was added to a solution of tert-butyl N-tert-butoxycarbonyl-N-[3-ethynyl-5-(4-isopropylsulfonylphenyl)pyrazin-2-yl]carbamate (150 mg, 0.2990 mmol), [1-(4-bromophenyl)-2-(tert-butoxycarbonylamino)ethyl]tert-butyl carbonate (186.7 mg, 0.4485 mmol), iodocopper (6.833 mg, 0.03588 mmol) and dichloropalladium; triethylphosphane (6.184 mg, 0.01495 mmol) in DMF (1.500 mL) and the resulting solution was heated at 120° C. for 7 minutes in a sealed tube. The reaction mixture was cooled to ambient temperature and diluted with EtOAc and 1M HCl/brine (1:1). The layers were separated and the aqueous layer was extracted with ethyl acetate. The combined organics extracts were washed with brine, dried over (MgSO$_4$) and concentrated in vacuo.

Step 2: 2-amino-1-(4-((3-amino-6-(4-(isopropylsulfonyl)phenyl)pyrazin-2-yl)ethynyl)phenyl)ethanol

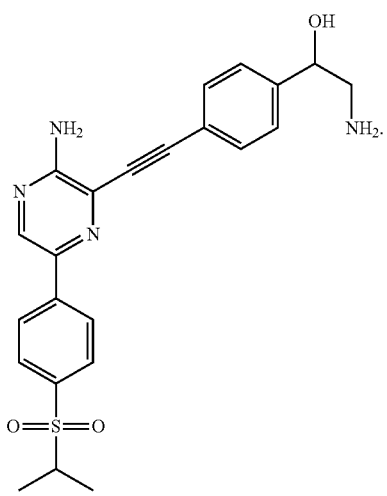 [SMILES: CC(C)S(=O)(=O)c1ccc(-c2cnc(N)c(C#Cc3ccc(C(O)CN)cc3)n2)cc1]

To a solution of [1-[4-[2-[3-[bis(tert-butoxycarbonyl)amino]-6-(4-isopropylsulfonylphenyl)pyrazin-2-yl]ethynyl]phenyl]-2-(tert-butoxycarbonylamino)ethyl]tert-butyl carbonate (250.3 mg, 0.2990 mmol) in DCM (2.503 mL) was added TFA (1 mL, 12.98 mmol) and the mixture was stirred at ambient temperature for 18 hours. After this time ether was added to the reaction mixture, the precipitate which resulted was isolated by filtration and dried under vacuum. The filtrate was recombined with precipitate and re-dissolved in DCM. Polymer supported 3-Mercaptopropyl ethyl sulfide was added to the solution and this was left to stir for 15 minutes at ambient temperature. After this time the resin was removed by filtration and washed with DCM. The filtrate was concentrated in vacuo and the material was purified by reverse phase preparative HPLC [Waters Sunfire C18, 10 μM, 100 Å column, gradient 10%-95% B (solvent A: 0.05% TFA in water; solvent B: CH$_3$CN) over 16 minutes at 25 mL/min]. The fractions were collected, passed through a sodium bicarbonate cartridge to give the titled product as a solid (15.01 mg, 11.5% Yield). $^1$H NMR (400.0 MHz, DMSO) δ 1.18 (d, J=6.8 Hz, 6H), 2.65 (dd, J=8.1, 12.8 Hz, 2H), 3.45 (t, J=6.8 Hz, 1H), 4.58 (dd, J=3.7, 7.9 Hz, 1H), 5.60 (br s, 1H), 7.15 (s, 2H), 7.43 (d, J=8.3 Hz, 2H), 7.76 (d, J=8.2 Hz, 2H), 7.91 (d, J=8.5 Hz, 2H), 8.24 (d, J=8.5 Hz, 2H) and 8.75 (s, 1H) ppm; MS (ES$^+$) 437.1.

Compound I-42: 5-(4-(isopropylsulfonyl)phenyl)-3-((2-(piperazin-1-yl)phenyl)ethynyl)pyrazin-2-amine $^1$H NMR (400.0 MHz, DMSO) δ 1.20 (dd, J=6.9, 9.0 Hz, 6H), 2.80 (s, 2H), 2.92-2.94 (m, 2H), 3.09-3.11 (m, 2H), 3.33 (d, J=9.5 Hz, 2H), 3.45-3.50 (m, 1H), 7.00-7.30 (m, 3H), 7.40-7.50 (m, 1H), 7.70-7.98 (m, 2H), 8.25 (d, J=8.5 Hz, 1.5H), 8.44 (s, 0.5H), 8.76 (s, 0.7H) and 8.96 (s, 0.3H) ppm; MS (ES$^+$) 462.1

Compound I-43: 3-((1H-indazol-4-yl)ethynyl)-5-(4-(isopropylsulfonyl)phenyl)pyrazin-2-amine $^1$H NMR (400.0 MHz, DMSO) δ 1.18 (6H, m), 3.45 (1H, m), 7.16 (2H, br s), 7.45 (1H, t), 7.60 (1H, m), 7.68 (1H, m), 7.91 (2H, m), 8.27-8.31 (3H, m), 8.80 (1H, s) and 11.40 (1H, br s) ppm; MS (ES$^+$) 418.0

Compound I-44: 3-((1H-indazol-5-yl)ethynyl)-5-(4-(isopropylsulfonyl)phenyl)pyrazin-2-amine $^1$H NMR (400.0 MHz, DMSO) δ 1.18 (6H, m), 3.41-3.48 (1H, m), 7.15 (2H, br s), 7.62 (1H, m), 7.72 (1H, m), 7.90 (2H, m), 8.19-8.31 (4H, m), 8.74 (1H, s) and 13.36 (1H, s); MS (ES$^+$) 418.0

Compound I-45: (2-((3-amino-6-(4-(isopropylsulfonyl)phenyl)pyrazin-2-yl)ethynyl)phenyl)methanol $^1$H NMR (400.0 MHz, DMSO) δ 1.21 (d, J=6.7 Hz, 6H), 3.35 (s, 1H), 4.68 (s, 2H), 6.99 (s, 1H), 7.45-7.50 (m, 2H), 7.65 (d, 1H), 7.75 (d, 1H), 7.97 (d, J=8.5 Hz, 2H), 8.45 (d, J=8.5 Hz, 2H) and 8.98 (s, 1H) ppm; MS (ES$^-$) 406.0

Compound I-46: 3-((3-amino-6-(4-(isopropylsulfonyl)phenyl)pyrazin-2-yl)ethynyl)-4-methylphenol $^1$H NMR (400.0 MHz, DMSO) δ 1.18 (d, J=6.7 Hz, 6H), 2.40 (s, 3H), 3.35 (s, 1H), 6.80 (d, 1H), 7.05 (br s, 2H), 7.11 (d, J=2.5 Hz, 2H), 7.90 (d, J=8.5 Hz, 2H), 8.23 (d, J=8.5 Hz, 2H) and 8.75 (s, 1H) ppm; MS (ES$^+$) 408.1

Compound I-47: (3-((3-amino-6-(4-(isopropylsulfonyl)phenyl)pyrazin-2-yl)ethynyl)-5-chlorophenyl)methanol ¹H NMR (400.0 MHz, DMSO) δ 1.18 (d, J=6.8 Hz, 6H), 3.45 (s, 1H), 4.55 (d, J=5.8 Hz, 2H), 5.47 (t, J=5.8 Hz, 1H), 7.25 (s, 2H), 7.47 (s, 1H), 7.67 (s, 1H), 7.85 (s, 1H), 7.91 (d, J=8.5 Hz, 2H), 8.23-8.25 (m, 2H) and 8.78 (s, 1H) ppm; MS (ES⁺) 442.0

Compound I-48: 2-amino-N-(3-((3-amino-6-(4-(isopropylsulfonyl)phenyl)pyrazin-2-yl)ethynyl)phenyl)acetamide ¹H NMR (400.0 MHz, DMSO) δ 1.18 (d, J=6.8 Hz, 6H), 3.45 (s, 1H), 7.17 (s, 2H), 7.42 (d, J=7.9 Hz, 1H), 7.49 (s, 1H), 7.70 (d, 1H), 7.90 (d, J=8.5 Hz, 2H), 8.07 (s, 1H), 8.25 (d, J=8.5 Hz, 2H) and 8.77 (s, 1H) ppm; MS (ES⁺) 450.1

Analytical Data:

| Cmpd No | Exact Mass (ES+) | LCMS Retention Time (min) | HNMR |
|---|---|---|---|
| I-1 | 396 | 0.92 | — |
| I-2 | 428.1 | 10 | H NMR (400.0 MHz, DMSO) d 1.19 (d, J = 6.8 Hz, 6H), 3.46 (sept, 1H), 7.21 (s, 2H), 7.61-7.68 (m, 2H), 7.72-7.76 (m, 1H), 7.93 (d, J = 8.6 Hz, 2H), 8.05-8.14 (m, 3H), 8.29 (d, J = 8.5 Hz, 2H), 8.40 (d, J = 8.5 Hz, 1H) and 8.81 (s, 1H) ppm |
| I-3 | 408.5 | 9.42 | H NMR (400.0 MHz, DMSO) d 1.18 (d, J = 6.7 Hz, 6H), 3.45 (sept, 1H), 3.82 (s, 3H), 7.04-7.07 (m, 1H), 7.18 (br s, 2H), 7.36-7.41 (m, 3H), 7.91 (d, J = 8.6 Hz, 2H), 8.24 (d, J = 8.6 Hz, 2H) and 8.76 (s, 1H) ppm |
| I-4 | 346.1 | 7.47 | H NMR (400.0 MHz, DMSO) d 1.17 (d, J = 6.8 Hz, 6H), 1.44 (d, J = 6.6 Hz, 3H), 3.44 (sept, 1H), 4.69 (q, J = 6.5 Hz, 1H), 5.62 (s, 1H), 6.96 (s, 2H), 7.88 (d, J = 8.4 Hz, 2H), 8.20 (d, J = 8.4 Hz, 2H) and 8.72 (s, 1H) ppm |
| I-5 | 302.12 | 1.28 | H NMR (400.0 MHz, DMSO) d 1.18 (d, J = 6.8 Hz, 6H), 3.44 (t, J = 6.8 Hz, 1H), 4.76 (s, 1H), 7.01 (s, 2H), 7.89 (d, J = 8.5 Hz, 2H), 8.20 (d, J = 8.5 Hz, 2H) and 8.75 (s, 1H) ppm |
| I-6 | 435.26 | 3.38 | H NMR (400.0 MHz, DMSO) d 1.18 (d, J = 6.7 Hz, 6H), 2.08 (s, 3H), 3.45 (t, J = 6.8 Hz, 1H), 7.16 (s, 2H), 7.40 (t, J = 7.9 Hz, 1H), 7.47 (t, J = 1.0 Hz, 1H), 7.49 (s, 1H), 7.89-7.91 (m, 2H), 8.01 (d, J = 1.5 Hz, 1H), 8.25 (dd, J = 1.6, 7.0 Hz, 2H), 8.76 (s, 1H) and 10.11 (s, 1H) ppm |
| I-7 | 378.2 | 3.6 | H NMR (400.0 MHz, DMSO) d 1.19 (d, J = 6.7 Hz, 6H), 3.41-3.50 (m, 1H), 7.14 (br s, 2H), 7.48-7.49 (m, 3H), 7.78-7.81 (m, 2H), 7.91 (d, J = 8.5 Hz, 2H), 8.24 (d, J = 8.5 Hz, 2H) and 8.76 (s, 1H) ppm |
| I-8 | 384.1 | 0.99 | — |
| I-9 | 412.18 | 3.87 | H NMR (400.0 MHz, DMSO) d 1.18 (d, J = 6.8 Hz, 6H), 3.45 (t, J = 6.8 Hz, 1H), 7.25 (s, 2H), 7.48-7.57 (m, 2H), 7.73 (dt, J = 7.5, 2.2 Hz, 1H), 7.91 (d, J = 8.5 Hz, 2H), 8.00 (t, J = 1.7 Hz, 1H), 8.24 (dd, J = 1.6, 7.0 Hz, 2H) and 8.78 (s, 1H) ppm |
| I-10 | 392.21 | 3.68 | H NMR (400.0 MHz, DMSO) d 1.19 (d, J = 6.7 Hz, 6H), 3.45 (m, 1H), 4.19 (s, 2H), 6.47 (s, 1H), 7.25-7.28 (m, 1H), 7.35 (d, J = 6.8 Hz, 4H), 7.95 (d, J = 8.5 Hz, 2H), 8.39 (d, J = 8.5 Hz, 2H), 8.89 (s, 1H) and 12.25 (s, 1H) ppm |
| I-11 | 392.4 | 9.72 | H NMR (400.0 MHz, DMSO) d 1.18 (d, J = 6.9 Hz, 6H), 2.36 (s, 3H), 3.45 (sept, 1H), 7.14 (s, 2H), 7.29-7.30 (m, 1H), 7.36 (t, 1H), 7.58 (d, J = 7.5 Hz, 1H), 7.64 (s, 1H), 7.91 (d, J = 8.5 Hz, 2H), 8.24 (d, J = 8.5 Hz, 2H) and 8.76 (s, 1H) ppm |
| I-12 | 412.18 | 3.84 | H NMR (400.0 MHz, DMSO) d 1.18 (d, J = 6.9 Hz, 6H), 3.45 (t, J = 6.8 Hz, 1H), 7.15 (br s, 2H), 7.46-7.54 (m, 2H), 7.65 (dd, J = 1.1, 7.9 Hz, 1H), 7.90-7.97 (m, 3H), 8.24 (dd, J = 1.6, 7.0 Hz, 2H) and 8.81 (s, 1H) ppm |
| I-13 | 379.18 | 3.32 | H NMR (400.0 MHz, DMSO) d 1.18 (d, J = 6.8 Hz, 6H), 3.45 (t, J = 6.8 Hz, 1H), 7.27 (s, 2H), 7.52 (dd, J = 4.9, 7.9 Hz, 1H), 7.91 (d, J = 8.5 Hz, 2H), 8.20-8.25 (m, 3H), 8.64 (d, J = 3.9 Hz, 1H), 8.79 (s, 1H) and 8.97 (s, 1H) ppm |
| I-14 | 396 | 0.92 | — |
| I-15 | 403 | 0.87 | — |
| I-16 | 347.1 | 1.23 | H NMR (400.0 MHz, DMSO) d 1.38 (d, 6H), 5.11 (sept, 1H), 6.49 (d, 1H), 6.77 (s, 2H), 6.87 (dd, 1H), 7.12 (s, 1H), 7.18 (d, 1H), 7.25 (t, 1H), 7.99 (dd, 1H), 8.20 (d, 1H), 8.55 (s, 1H) and 9.74 (s, 1H) ppm |

| Cmpd No | Exact Mass (ES+) | LCMS Retention Time (min) | HNMR |
|---|---|---|---|
| I-17 | 435.1 | 1.05 | H NMR (400.0 MHz, DMSO) d 1.65-1.74 (m, 2H), 2.06 (d, 2H), 2.85-2.90 (m, 2H), 3.36 (d, 2H), 3.59-3.65 (m, 1H), 6.89 (dd, 1H), 7.14-7.21 (m, 2H), 7.27 (t, 1H), 7.90 (d, 2H), 8.23 (br s, 1H), 8.28 (d, 2H), 8.54 (br s, 1H), 8.77 (s, 1H) and 9.78 (s, 1H) ppm |
| I-18 | 313.1 | 1.35 | H NMR (400.0 MHz, DMSO) d 6.89 (dd, 1H), 7.12 (d, 1H), 7.14 (br s, 2H), 7.18 (d, 1H), 7.25 (t, 1H), 7.59 (dt, 1H), 7.79 (dt, 1H), 7.85 (d, 1H), 7.94 (d, 1H), 8.46 (s, 1H) and 9.77 (s, 1H) ppm |
| I-19 | 408.1 | 0.91 | — |
| I-20 | 479.3 | 0.59 | H NMR (400.0 MHz, DMSO) d 1.18 (d, J = 6.8 Hz, 6H), 2.11-2.15 (m, 2H), 2.84 (d, J = 4.9 Hz, 6H), 3.21-3.27 (m, 2H), 3.45 (sept, 1H), 4.13 (t, 2H), 7.05-7.08 (m, 1H), 7.17 (s, 2H), 7.40 (d, J = 5.0 Hz, 3H), 7.91 (d, J = 8.6 Hz, 2H), 8.23 (d, J = 8.5 Hz, 2H), 8.77 (s, 1H) and 9.34 (s, 1H) ppm |
| I-21 | 393.1 | 8.47 | H NMR (400.0 MHz, DMSO) d 1.18 (d, 6H), 3.44 (sept, 1H), 5.39 (br s, 2H), 6.66-6.69 (m, 1H), 6.93 (d, J = 7.3 Hz, 2H), 7.06-7.13 (m, 3H), 7.90 (d, J = 8.6 Hz, 2H), 8.24 (d, J = 8.5 Hz, 2H) and 8.74 (s, 1H) ppm |
| I-22 | 384.1 | 9.19 | H NMR (400.0 MHz, DMSO) d 1.18 (d, J = 6.9 Hz, 6H), 3.45 (sept, 1H), 7.19 (br s, 2H), 7.18-7.21 (m, 1H), 7.67-7.69 (m, 1H), 7.70-7.79 (m, 1H), 7.90 (d, J = 8.5 Hz, 2H), 8.23 (d, J = 8.5 Hz, 2H) and 8.76 (s, 1H) ppm |
| I-23 | 350.1 | 1.24 | H NMR (400.0 MHz, DMSO) d 3.34 (s, 3H), 5.15 (d, 1H), 6.88 (dd, 1H), 7.09 (br s, 2H), 7.19 (d, 1H), 7.27 (t, 1H), 7.60-7.69 (m, 2H), 7.89 (d, 1H), 8.17 (d, 1H), 8.60 (s, 1H) and 9.76 (s, 1H) ppm |
| I-24 | 451.2 | 0.66 | H NMR (400.0 MHz, DMSO) d 1.18 (d, J = 6.7 Hz, 6H), 2.00-2.06 (m, 2H), 2.97-3.02 (m, 2H), 3.46 (sept, 1H), 4.13 (t, 2H), 7.05-7.08 (m, 1H), 7.17 (s, 2H), 7.39-7.41 (m, 3H), 7.71 (s, 3H), 7.91 (d, J = 8.7 Hz, 2H), 8.23 (d, J = 8.6 Hz, 2H) and 8.77 (s, 1H) ppm |
| I-25 | 437.3 | 0.63 | H NMR (400.0 MHz, DMSO) d 1.18 (d, J = 6.8 Hz, 6H), 3.26-3.29 (m, 2H), 3.45 (sept, 1H), 4.24 (t, J = 5.0 Hz, 2H), 7.09-7.12 (m, 1H), 7.18 (s, 2H), 7.42-7.44 (m, 3H), 7.91 (d, 2H), 7.95 (s, 3H), 8.24 (d, J = 8.6 Hz, 2H) and 8.78 (s, 1H) ppm |
| I-26 | 465.3 | 0.68 | H NMR (400.0 MHz, DMSO) d 1.20 (d, 6H), 2.91 (d, 6H), 3.45 (sept, 1H), 3.55-3.57 (m, 2H), 4.39-4.41 (m, 2H), 7.11-7.14 (m, 1H), 7.18 (s, 2H), 7.41-7.47 (m, 3H), 7.91 (d, 2H), 8.23 (d, 2H), 8.78 (s, 1H) and 9.60 (s, 1H) ppm |
| I-27 | 342.2 | 8.67 | H NMR (400.0 MHz, DMSO) d 0.94-0.97 (m, 4H), 1.17 (d, J = 6.8 Hz, 6H), 1.65-1.71 (m, 1H), 3.43 (sept, 1H), 6.89 (s, 2H), 7.87 (d, J = 8.5 Hz, 2H), 8.18 (d, J = 8.5 Hz, 2H) and 8.65 (s, 1H) ppm |
| I-28 | 421.4 | 2.92 | H NMR (400.0 MHz, DMSO) d 1.18 (d, 6H), 2.27 (s, 3H), 3.41-3.50 (m, 1H), 3.68 (s, 2H), 7.16 (br s, 2H), 7.41-7.42 (m, 2H), 7.64-7.66 (m, 1H), 7.75 (s, 1H), 7.90 (d, 2H), 8.24 (d, 2H) and 8.76 (s, 1H) ppm |
| I-29 | 346.1 | 7.45 | H NMR (400.0 MHz, DMSO) d 1.17 (d, J = 6.8 Hz, 6H), 1.44 (d, J = 6.7 Hz, 3H), 3.43 (sept, 1H), 4.69 (q, 1H), 5.61 (br s, 1H), 6.97 (br s, 2H), 7.88 (dd, J = 1.6, 7.0 Hz, 2H), 8.20 (dd, J = 1.7, 7.0 Hz, 2H) and 8.72 (s, 1H) ppm |
| I-30 | 349.1 | 1.23 | H NMR (400.0 MHz, DMSO) d 1.03 (t, 3H), 1.29 (d, J = 12.1 Hz, 2H), 2.32-2.43 (m, 2H), 3.60-3.67 (m, 2H), 4.14 (d, 2H), 6.47 (s, 1H), 6.74 (s, 2H), 6.86 (dd, 1H), 7.09 (s, 1H), 7.15 (d, 1H), 7.24 (t, 1H), 8.21 (s, 1H) and 9.74 (s, 1H) ppm |
| I-31 | 384 | 0.88 | — |
| I-32 | 379.1 | 1.06 | H NMR (400.0 MHz, DMSO) d 1.18 (d, 6H), 3.45 (sept, 1H), 7.32 (s, 2H), 7.76 (d, 2H), 7.91 (d, 2H), 8.24 (d, 2H), 8.68 (d, 2H) and 8.82 (s, 1H) ppm |
| I-33 | 379.18 | 3.35 | H NMR (400.0 MHz, DMSO) d 1.18 (d, J = 6.8 Hz, 6H), 3.45 (s, 1H), 7.23 (s, 2H), 7.50 (d, 1H), 7.89-7.96 (m, 4H), 8.25-8.27 (m, 2H), 8.66 (s, 1H) and 8.82 (s, 1H) ppm |

| Cmpd No | Exact Mass (ES+) | LCMS Retention Time (min) | HNMR |
|---|---|---|---|
| I-34 | 436.1 | 1.35 | H NMR (400.0 MHz, DMSO) d 1.30-1.41 (m, 2H), 1.56 (d, 2H), 3.07-3.12 (m, 2H), 3.34-3.40 (m, 2H), 3.71 (dd, J = 3.9, 11.4 Hz, 1H), 6.67-6.70 (m, 1H), 6.94 (br s, 2H), 6.95 (d, 1H), 7.01 (d, 1H), 7.07 (t, 1H), 7.70 (d, 2H), 8.05 (d, 2H), 8.55 (s, 1H) and 9.57 (s, 1H) ppm |
| I-35 | 394.2 | 8.6 | H NMR (400.0 MHz, DMSO) d 1.18 (d, J = 6.9 Hz, 6H), 3.45 (sept, 1H), 6.87-6.90 (m, 1H), 7.13-7.15 (m, 3H), 7.19-7.21 (m, 1H), 7.23-7.29 (m, 1H), 7.90 (d, J = 8.6 Hz, 2H), 8.24 (d, J = 8.6 Hz, 2H), 8.75 (s, 1H) and 9.77 (s, 1H) ppm |
| I-36 | 507.3 | 0.58 | H NMR (400.0 MHz, DMSO) d 1.09 (d, J = 6.8 Hz, 6H), 3.22-3.25 (m, 2H), 3.41-3.74 (m, 7H), 4.01 (d, J = 12.6 Hz, 2H), 4.43 (s, 2H), 6.98 (d, 2H), 7.14 (d, J = 7.4 Hz, 1H), 7.41-7.48 (m, 3H), 7.92 (d, J = 8.5 Hz, 2H), 8.23 (d, 2H), 8.78 (s, 1H) and 9.88 (s, 1H) ppm |
| I-37 | 421.1 | 1.28 | H NMR (400.0 MHz, DMSO) d 1.18 (d, 6H), 3.45 (sept, 1H), 7.22 (br s, 2H), 7.53 (br s, 1H), 7.57 (t, 1H), 7.91 (d, 2H), 7.94 (d, 2H), 8.10 (s, 1H), 8.24 (s, 2H), 8.29 (d, 1H) and 8.78 (s, 1H) ppm |
| I-38 | 393.1 | 0.83 | H NMR (400.0 MHz, DMSO) d 1.18 (d, J = 6.9 Hz, 6H), 3.44 (t, J = 6.8 Hz, 1H), 5.67 (s, 2H), 6.59 (t, J = 7.5 Hz, 1H), 6.77 (d, J = 8.0 Hz, 1H), 7.07 (s, 2H), 7.15 (dd, J = 1.5, 15.4 Hz, 1H), 7.43 (dd, J = 1.4, 7.7 Hz, 1H), 7.90 (d, J = 8.5 Hz, 2H), 8.25 (d, J = 8.5 Hz, 2H) and 8.72 (s, 1H) ppm |
| I-39 | 382.1 | 0.69 | H NMR (400.0 MHz, DMSO) d 1.18 (d, J = 6.8 Hz, 6H), 3.43-3.46 (m, 1H), 3.78 (s, 3H), 7.12 (s, 2H), 7.53 (br s, 1H), 7.86 (br s, 1H), 7.90 (d, J = 8.5 Hz, 2H), 8.23 (d, J = 8.5 Hz, 2H) and 8.77 (s, 1H) ppm |
| I-40 | 396.3 | 0.91 | H NMR (400.0 MHz, DMSO) d 1.18 (d, J = 6.8 Hz, 6H), 3.45 (t, J = 6.8 Hz, 1H), 7.15 (s, 2H), 7.33 (td, J = 7.5, 2.8 Hz, 2H), 7.55 (s, 1H), 7.90-7.93 (m, 3H), 8.24 (d, J = 8.5 Hz, 2H) and 8.80 (s, 1H) ppm |
| I-41 | 394.1 | 1.1 | H NMR (400.0 MHz, DMSO) d 1.18 (d, 6H), 3.45 (sept, 1H), 6.20 (s, 2H), 6.52 (d, 1H), 7.06 (d, 1H), 7.07 (br s, 2H), 7.45 (dd, 1H), 7.90 (d, 2H), 8.25 (d, 2H) and 8.78 (s, 1H) ppm |
| I-42 | 437.1 | 0.61 | H NMR (400.0 MHz, DMSO) d 1.18 (d, J = 6.8 Hz, 6H), 2.65 (dd, J = 8.1, 12.8 Hz, 2H), 3.45 (t, J = 6.8 Hz, 1H), 4.58 (dd, J = 3.7, 7.9 Hz, 1H), 5.60 (br s, 1H), 7.15 (s, 2H), 7.43 (d, J = 8.3 Hz, 2H), 7.76 (d, J = 8.2 Hz, 2H), 7.91 (d, J = 8.5 Hz, 2H), 8.24 (d, J = 8.5 Hz, 2H) and 8.75 (s, 1H) ppm |
| I-43 | 462.1 | 0.71 | H NMR (400.0 MHz, DMSO) d 1.20 (dd, J = 6.9, 9.0 Hz, 6H), 2.80 (s, 2H), 2.92-2.94 (m, 2H), 3.09-3.11 (m, 2H), 3.33 (d, J = 9.5 Hz, 2H), 3.45-3.50 (m, 1H), 7.00-7.30 (m, 3H), 7.40-7.50 (m, 1H), 7.70-7.98 (m, 2H), 8.25 (d, J = 8.5 Hz, 1.5H), 8.44 (s, 0.5H), 8.76 (s, 0.7H) and 8.96 (s, 0.3H) ppm |
| I-44 | 418 | 0.78 | (DMSO) 1.18 (6H, m), 3.45 (1H, m), 7.16 (2H, br s), 7.45 (1H, t), 7.60 (1H, m), 7.68 (1H, m), 7.91 (2H, m), 8.27-8.31 (3H, m), 8.80 (1H, s) and 11.40 (1H, br s) ppm |
| I-45 | 418 | 0.76 | (DMSO) 1.18 (6H, m), 3.41-3.48 (1H, m), 7.15 (2H, br s), 7.62 (1H, m), 7.72 (1H, m), 7.90 (2H, m), 8.19-8.31 (4H, m), 8.74 (1H, s) and 13.36 (1H, s) |
| I-46 | — | — | H NMR (400.0 MHz, DMSO) d 1.21 (d, J = 6.7 Hz, 6H), 3.35 (s, 1H), 4.68 (s, 2H), 6.99 (s, 1H), 7.45-7.50 (m, 2H), 7.65 (d, 1H), 7.75 (d, 1H), 7.97 (d, J = 8.5 Hz, 2H), 8.45 (d, J = 8.5 Hz, 2H) and 8.98 (s, 1H) ppm |
| I-47 | 408.1 | 0.83 | H NMR (400.0 MHz, DMSO) d 1.18 (d, J = 6.7 Hz, 6H), 2.40 (s, 3H), 3.35 (s, 1H), 6.80 (d, 1H), 7.05 (br s, 2H), 7.11 (d, J = 2.5 Hz, 2H), 7.90 (d, J = 8.5 Hz, 2H), 8.23 (d, J = 8.5 Hz, 2H) and 8.75 (s, 1H) ppm |
| I-48 | 442 | 0.85 | H NMR (400.0 MHz, DMSO) d 1.18 (d, J = 6.8 Hz, 6H), 3.45 (s, 1H), 4.55 (d, J = 5.8 Hz, 2H), 5.47 (t, J = 5.8 Hz, 1H), 7.25 (s, 2H), 7.47 (s, 1H), 7.67 (s, 1H), 7.85 (s, 1H), 7.91 (d, J = 8.5 Hz, 2H), 8.23-8.25 (m, 2H) and 8.78 (s, 1H) ppm |
| I-49 | 450.1 | 0.66 | H NMR (400.0 MHz, DMSO) d 1.18 (d, J = 6.8 Hz, 6H), 3.45 (s, 1H), 7.17 (s, 2H), 7.42 (d, J = 7.9 Hz, 1H), 7.49 (s, 1H), 7.70 (d, 1H), 7.90 (d, J = 8.5 Hz, 2H), 8.07 (s, 1H), 8.25 (d, J = 8.5 Hz, 2H) and 8.77 (s, 1H) ppm |

Examples 14

Cellular ATR Inhibition Assay

Compounds can be screened for their ability to inhibit intracellular ATR using an immunofluorescence microscopy assay to detect phosphorylation of the ATR substrate histone H2AX in hydroxyurea treated cells. HT29 cells are plated at 14,000 cells per well in 96-well black imaging plates (BD 353219) in McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds are then added to the cell media from a final concentration of 25 µM in 3-fold serial dilutions and the cells are incubated at 37° C. in 5% $CO_2$. After 15 min, hydroxyurea (Sigma H8627) is added to a final concentration of 2 mM.

After 45 min of treatment with hydroxyurea, the cells are washed in PBS, fixed for 10 min in 4% formaldehyde diluted in PBS (Polysciences Inc 18814), washed in 0.2% Tween-20 in PBS (wash buffer), and permeabilised for 10 min in 0.5% Triton X-100 in PBS, all at room temperature. The cells are then washed once in wash buffer and blocked for 30 min at room temperature in 10% goat serum (Sigma G9023) diluted in wash buffer (block buffer). To detect H2AX phosphorylation levels, the cells are then incubated for 1 h at room temperature in primary antibody (mouse monoclonal anti-phosphorylated histone H2AX Ser139 antibody; Upstate 05-636) diluted 1:250 in block buffer. The cells are then washed five times in wash buffer before incubation for 1 h at room temperature in the dark in a mixture of secondary antibody (goat anti-mouse Alexa Fluor 488 conjugated antibody; Invitrogen A11029) and Hoechst stain (Invitrogen H3570); diluted 1:500 and 1:5000, respectively, in wash buffer. The cells are then washed five times in wash buffer and finally 100 ul PBS is added to each well before imaging.

Cells are imaged for Alexa Fluor 488 and Hoechst intensity using the BD Pathway 855 Bioimager and Attovision software (BD Biosciences, Version 1.6/855) to quantify phosphorylated H2AX Serl 39 and DNA staining, respectively. The percentage of phosphorylated H2AX-positive nuclei in a montage of 9 images at 20× magnification is then calculated for each well using BD Image Data Explorer software (BD Biosciences Version 2.2.15). Phosphorylated H2AX-positive nuclei are defined as Hoechst-positive regions of interest containing Alexa Fluor 488 intensity at 1.75-fold the average Alexa Fluor 488 intensity in cells not treated with hydroxyurea. The percentage of H2AX positive nuclei is finally plotted against concentration for each compound and IC50s for intracellular ATR inhibition are determined using Prism software (GraphPad Prism version 3.0cx for Macintosh, GraphPad Software, San Diego Calif., USA).

The compounds described herein can also be tested according to other methods known in the art (see Sarkaria et al, "Inhibition of ATM and ATR Kinase Activities by the Radiosensitizing Agent, Caffeine: *Cancer Research* 59: 4375-5382 (1999); Hickson et al, "Identification and Characterization of a Novel and Specific Inhibitor of the Ataxia-Telangiectasia Mutated Kinase ATM" *Cancer Research* 64: 9152-9159 (2004); Kim et al, "Substrate Specificities and Identification of Putative Substrates of ATM Kinase Family Members" *The Journal of Biological Chemistry*, 274(53): 37538-37543 (1999); and Chiang et al, "Determination of the catalytic activities of mTOR and other members of the phosphoinositide-3-kinase-related kinase family" *Methods Mol. Biol.* 281:125-41 (2004)).

Example 15

ATR Inhibition Assay

Compounds were screened for their ability to inhibit ATR kinase using a radioactive-phosphate incorporation assay. Assays were carried out in a mixture of 50 mM Tris/HCl (pH 7.5), 10 mM $MgCl_2$ and 1 mM DTT. Final substrate concentrations were 10 µM [γ-33P]ATP (3mCi 33P ATP/mmol ATP, Perkin Elmer) and 800 µM target peptide (ASELPAS-QPQPFSAKKK (SEQ. ID NO: 1)).

Assays were carried out at 25° C. in the presence of 5 nM full-length ATR. An assay stock buffer solution was prepared containing all of the reagents listed above, with the exception of ATP and the test compound of interest. 13.5 µL of the stock solution was placed in a 96 well plate followed by addition of 2 µL of DMSO stock containing serial dilutions of the test compound (typically starting from a final concentration of 15 µM with 3-fold serial dilutions) in duplicate (final DMSO concentration 7%). The plate was pre-incubated for 10 minutes at 25° C. and the reaction initiated by addition of 15 µL [γ-33P]ATP (final concentration 10 µM).

The reaction was stopped after 24 hours by the addition of 30 µL 0.1M phosphoric acid containing 2 mM ATP. A multiscreen phosphocellulose filter 96-well plate (Millipore, Cat no. MAPHN0B50) was pretreated with 100 µL 0.2M phosphoric acid prior to the addition of 45 µL of the stopped assay mixture. The plate was washed with 5×200 µL 0.2M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Below is a chart showing the ATR Inhibition Ki values of compounds of the disclosure. Compounds with a Ki value of ≤100 nM are marked with "+++." Compounds with a Ki value >100 nM but ≤1 uM are marked with "++." Compounds with a Ki value >1 uM but ≤13 uM are marked with "+." Compounds with % inhibition values reported instead are marked with *.

| Compound No. | Ki |
|---|---|
| I-1 | +++ |
| I-2 | +++ |
| I-3 | +++ |
| I-4 | ++ |
| I-5 | ++ |
| I-6 | +++ |
| I-7 | +++ |
| I-8 | ++ |

| Compound No. | Ki |
|---|---|
| I-9 | +++ |
| I-10 | + |
| I-11 | +++ |
| I-12 | +++ |
| I-13 | +++ |
| I-14 | +++ |
| I-15 | + |
| I-16 | +++ |
| I-17 | +++ |
| I-18 | +++ |
| I-19 | ++ |
| I-20 | +++ |
| I-21 | +++ |
| I-22 | +++ |
| I-23 | +++ |
| I-24 | +++ |
| I-25 | +++ |
| I-26 | ++ |
| I-27 | ++ |
| I-28 | +++ |
| I-29 | + |
| I-30 | +++ |
| I-31 | ++ |
| I-32 | +++ |
| I-33 | +++ |
| I-34 | +++ |
| I-35 | +++ |
| I-36 | ++ |
| I-37 | +++ |
| I-38 | ++ |
| I-39 | +++ |
| I-40 | +++ |
| I-41 | +++ |
| I-42 | +++ |
| I-43 | +++ |
| I-44 | +++ |
| I-45 | +++ |
| I-46 | * |
| I-47 | +++ |
| I-48 | +++ |
| I-49 | +++ |

% Inhibition

Alternatively, a compound's percent inhibition at a single concentration can also be reported. Compound I-46 had 30% inhibition of ATR at 15 uM.

Example 14

Cisplatin Sensitization Assay

Compounds can be screened for their ability to sensitize HCT116 colorectal cancer cells to Cisplatin using a 96 h cell viability (MTS) assay. HCT116 cells, which possess a defect in ATM signaling to Cisplatin (see, Kim et al.; *Oncogene* 21:3864 (2002); see also, Takemura et al.; *JBC* 281:30814 (2006)) are plated at 470 cells per well in 96-well polystyrene plates (Costar 3596) in 150 µl of McCoy's 5A media (Sigma M8403) supplemented with 10% foetal bovine serum (JRH Biosciences 12003), Penicillin/Streptomycin solution diluted 1:100 (Sigma P7539), and 2 mM L-glumtamine (Sigma G7513), and allowed to adhere overnight at 37° C. in 5% $CO_2$. Compounds and Cisplatin are then both added simultaneously to the cell media in 2-fold serial dilutions from a top final concentration of 10 µM as a full matrix of concentrations in a final cell volume of 200 µl, and the cells are then incubated at 37° C. in 5% $CO_2$. After 96 h, 40 µl of MTS reagent (Promega G358a) is added to each well and the cells are incubated for 1 h at 37° C. in 5% $CO_2$. Finally, absorbance is measured at 490 nm using a SpectraMax Plus 384 reader (Molecular Devices) and the concentration of compound required to reduce the IC50 of Cisplatin alone by at least 3-fold (to 1 decimal place) can be reported (CP3 shift).

| Cmpd No. | CP3 Shift (uM) |
|---|---|
| I-7 | 2.5 |
| I-21 | 0.312 |
| I-22 | 1.25 |
| I-33 | 2.5 |
| I-34 | 0.079 |
| I-35 | 0.118 |
| I-40 | 2.5 |

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

The invention claimed is:
1. A compound of formula I:

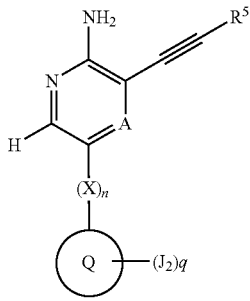

or a pharmaceutically acceptable salt thereof, wherein
A is N;
X is NR", C(O)NR", NR"CO, C(O)O, —C(R")═C(R")—, or
n is 0 or 1;
Q is a 5-7 membered monocyclic fully saturated, partially unsaturated, or aromatic ring containing 0-4 heteroatoms independently selected from nitrogen, oxygen, or sulfur; or
an 8-10 membered bicyclic fully saturated, partially unsaturated, or aromatic ring containing 0-6 heteroatoms independently selected from nitrogen, oxygen, or sulfur;
$R^5$ is H, $C_{1-6}$aliphatic, a 3-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur; $R^5$ is optionally substituted with 1-5 $J^5$ groups;
$J^5$ is halo, oxo, CN, $NO_2$, $X^1$—R, or —$(X^1)_p$-$Q^4$;
$X^1$ is $C_{1-10}$aliphatic; wherein 1-3 methylene units of said $C_{1-10}$aliphatic are optionally replaced with —NR'—, —O—, —S—, C(O), $S(O)_2$, or S(O); wherein $X^1$ is optionally and independently substituted with 1-4 occurrences of $NH_2$, $NH(C_{1-4}aliphatic)$, $N(C_{1-4}aliphatic)_2$, halogen, $C_{1-4}$-aliphatic, OH, $O(C_{1-4}$-aliphatic), $NO_2$, CN, $CO(C_{1-4}$-aliphatic), $CO_2H$, $CO_2(C_{1-4}$-aliphatic), $C(O)NH_2$, $C(O)NH(C_{1-4}$-aliphatic), $C(O)N(C_{1-4}$-aliphatic)_2$, $SO(C_{1-4}$-aliphatic), $SO_2(C_{1-4}$-aliphatic), $SO_2NH(C_{1-4}$-aliphatic), $SO_2N(C_{1-4}$-aliphatic)_2$, $NHC(O)(C_{1-4}aliphatic)$, $N(C_{1-4}$-aliphatic)$C(O)(C_{1-4}aliphatic)$, $NHSO_2(C_{1-4}aliphatic)$, or $N(C_{1-4}aliphatic)SO_2(C_{1-4}aliphatic)$, wherein said $C_{1-4}$aliphatic is optionally substituted with 1-3 occurrences of halo;
$Q^4$ is a 3-8 membered saturated, partially unsaturated, or fully unsaturated monocyclic ring having 0-4 heteroatoms independently selected from nitrogen, oxygen, or sulfur, or a 8-10 membered saturated, partially unsaturated, or fully unsaturated bicyclic ring having 0-6 heteroatoms independently selected from nitrogen, oxygen, or sulfur; each $Q^4$ is optionally substituted with 1-5 $J^{Q4}$;
$J^{Q4}$ is halo, CN, or $C_{1-4}$alkyl wherein up to 2 methylene units are optionally replaced with O, NR*, S, C(O), S(O), or $S(O)_2$;
R is H or $C_{1-4}$alkyl wherein said $C_{1-4}$alkyl is optionally substituted with 1-4 halo;
$J_2$ is halo, CN, or V, or $(V)_t$—$R^1$;

V is a $C_{1-10}$aliphatic group wherein up to 2 methylene units are optionally replaced with 0, NR", C(O), S, S(O), or $S(O)_2$; wherein said $C_{1-10}$aliphatic group is optionally substituted with 1-3 halo or CN;
$R^1$ is 3-7 membered aromatic or nonaromatic monocyclic ring having 0-3 heteroatoms selected from oxygen, nitrogen, or sulfur; wherein said monocyclic ring is optionally substituted with 1-3 occurrences of $C_{1-6}$aliphatic wherein up to 3 methylene units can be replaced with NR', O, S, CO, halo, CN, or a $C_{3-6}$cycloalkyl;
q is 0, 1, or 2;
p is 0 or 1;
t is 0 or 1;
R', R", and R* are each independently H or $C_1$-$C_4$ alkyl.
2. The compound of claim 1, wherein $R^5$ is optionally substituted $C_{1-6}$aliphatic, 3-7 membered monocyclic fully saturated, partially unsaturated, or aromatic ring containing 0-4 heteroatoms independently selected from nitrogen, oxygen, or sulfur; or an 8-10 membered bicyclic fully saturated, partially unsaturated, or aromatic ring containing 0-6 heteroatoms independently selected from nitrogen, oxygen, or sulfur.
3. The compound of claim 2, wherein n is 0.
4. The compound of claim 3, wherein Q is tetrahydropyridin-4-yl or pyridin-2-one-5-yl.
5. The compound of claim 3, wherein Q is an aromatic ring.
6. The compound of claim 5, wherein Q is a 5-6 membered ring.
7. The compound of claim 5, wherein Q is phenyl.
8. The compound of claim 1 or claim 7, wherein q is 1.
9. The compound of claim 6, wherein q is 1 and Ring Q is a 6-membered aromatic ring substituted in the para position with $J_2$.
10. The compound of claim 9, wherein $J_2$ is V.
11. The compound of claim 10, wherein V is a $C_{1-6}$aliphatic group wherein one methylene unit is optionally replaced with $S(O)_2$.
12. The compound of claim 11, wherein V is —$S(O)_2$ ($C_{1-4}$alkyl).
13. The compound of claim 12, wherein V is $S(O)_2CH(CH_3)_2$.
14. The compound of claim 8, wherein $J_2$ is CN and substituted in the ortho position.
15. The compound of claim 9, wherein $J_2$ is —$(V)_t$—$R^1$.
16. The compound of claim 15, wherein V is —$S(O)_2$.
17. The compound of claim 16, wherein $R^1$ is a 4-6 membered nonaromatic monocyclic ring having 1 heteroatom selected from oxygen, nitrogen, or sulfur.
18. The compound of claim 17, wherein the heteroatom is nitrogen or oxygen.
19. The compound of claim 18, wherein $J_2$ is —$S(O)_2$— piperidine or —$S(O)_2$— tetrahydropyran.
20. The compound of claim 1, wherein $R^5$ is a 3-7 membered monocyclic fully saturated, partially unsaturated, or aromatic ring containing 0-4 heteroatoms independently selected from nitrogen, oxygen, or sulfur.
21. The compound of claim 20, wherein $R^5$ is an aromatic ring containing 1-2 heteroatoms selected from oxygen, nitrogen, or sulfur.
22. The compound of claim 20, wherein $R^5$ is phenyl, naphthyl, thienyl, or pyridinyl.
23. The compound of claim 22, wherein $R^5$ is phenyl.
24. The compound of claim 23, wherein $R^5$ is substituted in the meta position with $J^5$.

25. The compound of claim 24, wherein $J^5$ is halo, oxo, CN, $X^1$—R, or —$(X^1)_p$-$Q^4$; wherein
   $X^1$ is $C_{1-10}$aliphatic; wherein 1-2 methylene units of said $C_{1-10}$aliphatic are optionally replaced with C(O), —NR'—, or —O—;
   $Q^4$ is a 3-8 membered saturated, partially unsaturated, or fully unsaturated monocyclic ring having 0-4 heteroatoms independently selected from nitrogen, oxygen, or sulfur; each $Q^4$ is optionally substituted with 1-5 $J^{Q4}$;
   $J^{Q4}$ is halo, CN, or $C_{1-4}$alkyl;
   R is H or $C_{1-4}$alkyl wherein said $C_{1-4}$alkyl is optionally substituted with 1-4 halo.

26. The compound of claim 25, wherein $J^5$ is halo, CN, $C_{1-4}$alkyl, OH, O($C_{1-4}$alkyl), —NH($C_{1-4}$alkyl), —O—($C_{1-4}$alkyl)-NH($C_{1-4}$alkyl), —O—($C_{1-4}$alkyl)-N($C_{1-4}$alkyl)$_2$, —O—($C_{1-4}$alkyl)-NH$_2$, —($C_{1-4}$alkyl)-NH($C_{1-4}$alkyl), —($C_{1-4}$alkyl)-NH$_2$, —($C_{1-4}$alkyl)-N($C_{1-4}$alkyl)$_2$, or —O—($C_{1-4}$alkyl)-(morpholinyl).

27. The compound of claim 25, wherein $J^5$ is halo, $C_{1-4}$alkyl, OH, NH$_2$, phenyl, —NH($C_{1-4}$alkyl), or O($C_{1-4}$alkyl).

28. The compound of claim 27, wherein $J^5$ is OH or NH$_2$.

29. The compound of claim 20, wherein $R^5$ is a 3-6 membered cycloalkyl ring.

30. The compound of claim 1, having formula Ia:

Ia wherein
   $R^5$ is an aromatic ring optionally containing 1-3 heteroatoms selected from nitrogen or sulfur; $R^5$ is optionally substituted with 1-5 $J^5$ groups;
   $J_2$ is V or —(V)$_t$—$R^1$;
   V is a $C_{1-6}$aliphatic group wherein one methylene unit is optionally replaced with S(O)$_2$;
   $R^1$ is a 5-6 membered nonaromatic monocyclic ring having 1 heteroatom selected from oxygen, nitrogen, or sulfur;
   t is 0 or 1.

31. The compound according to claim 30, wherein $R^5$ is optionally substituted phenyl.

32. The compound according to claim 31, wherein $J_2$ is S(O)$_2$($C_{1-6}$alkyl).

33. The compound of claim 32, wherein $J_2$ is S(O)$_2$CH(CH$_3$)$_2$.

34. The compound according to claim 30, wherein $R^5$ is phenyl and $J^5$ is fluoro, chloro, methyl, cyano, OH, OCH$_3$, —O(CH$_2$)$_2$N(CH$_3$)$_2$, —O(CH$_2$)$_3$N(CH$_3$)$_2$, CH$_2$NH(CH$_3$), NH$_2$, CH(CH$_3$)OH, NHC(O)CH$_3$, NHC(O)CH$_2$NH$_2$, —C(O)NH$_2$, CH$_2$OH, CH(OH)CH$_2$NH$_2$, piperazinyl, or —O—(CH$_2$)$_2$-(morpholinyl).

35. The compound of any one of claims 31-34, wherein $R^5$ is substituted in the meta position by one occurrence of $J^5$.

36. A compound selected from the following:

I-1

I-2

I-3

I-4

I-5

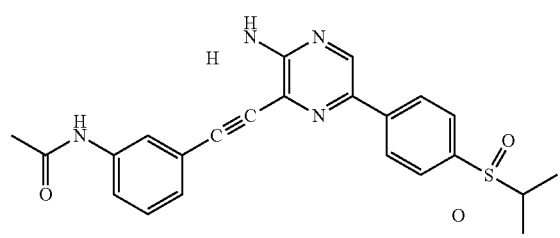
I-6
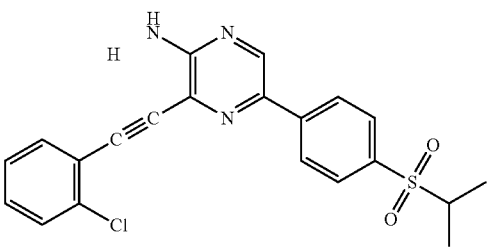
I-12
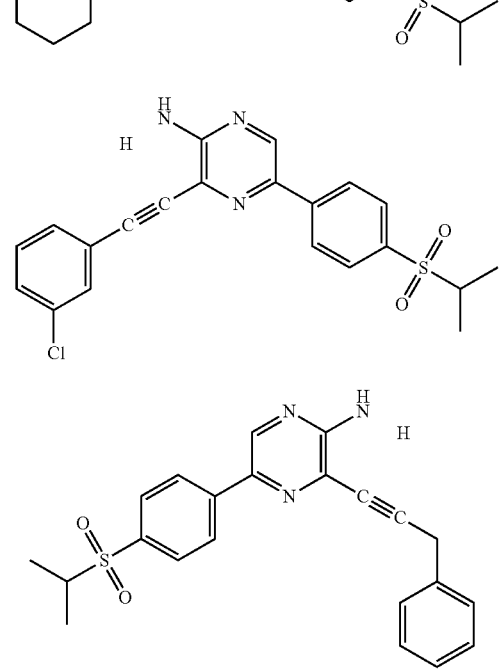
I-7
I-8
I-9
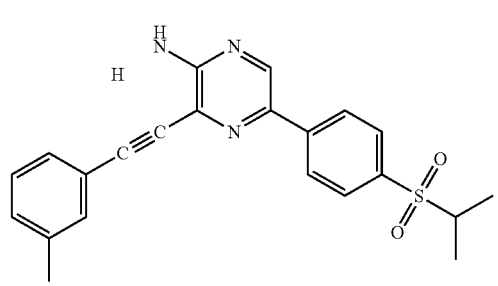
I-10
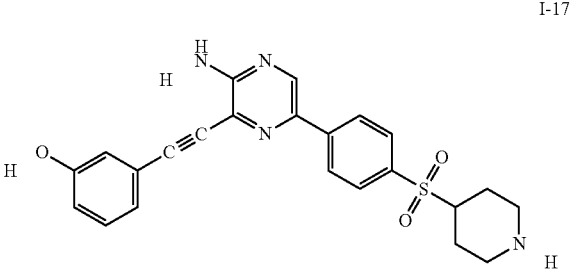
I-13
I-14
I-15
I-16
I-11
I-17

I-18
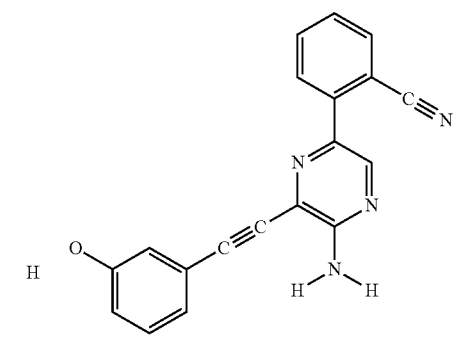
I-19
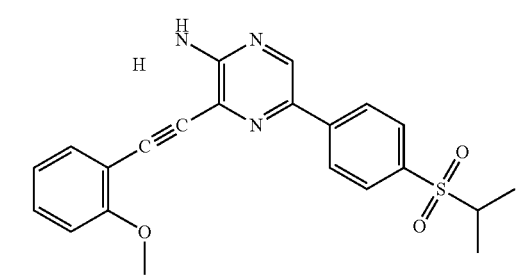
I-20
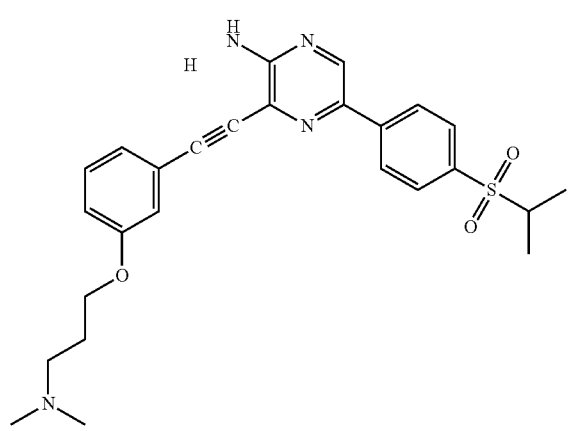
I-21
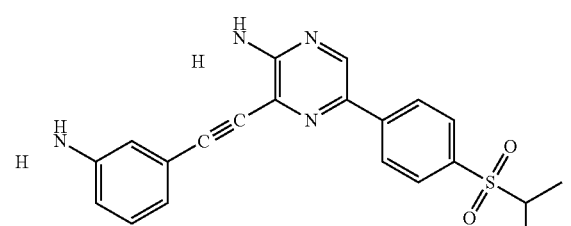
I-22
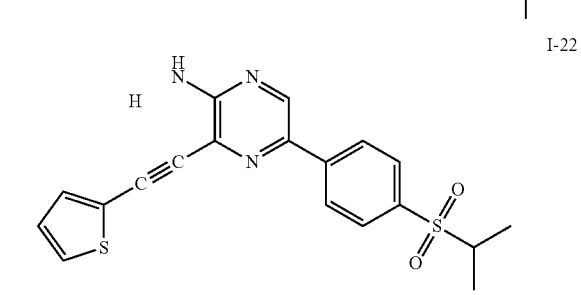
I-23
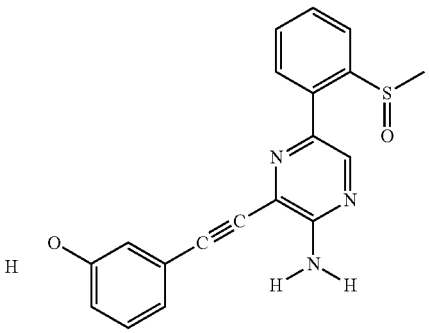
I-24
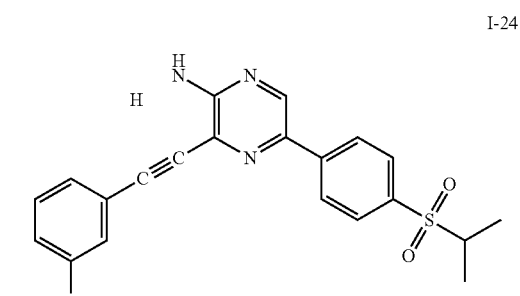
I-25
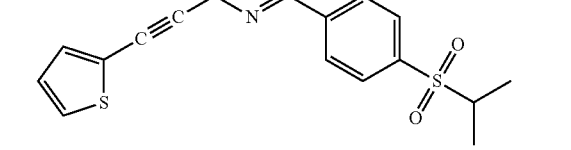
I-26
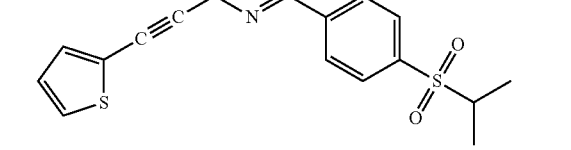

I-27 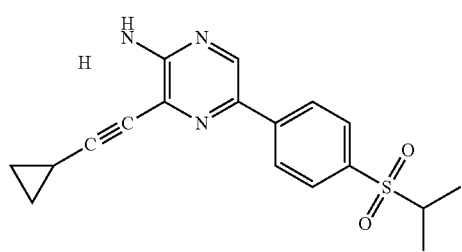
I-28 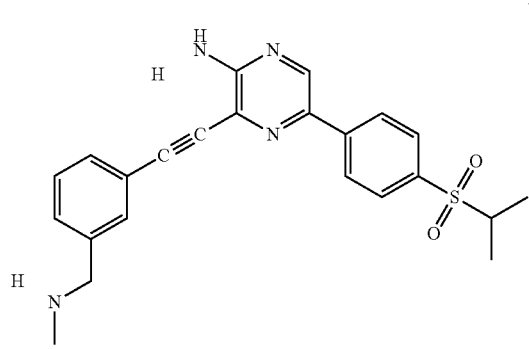
I-29 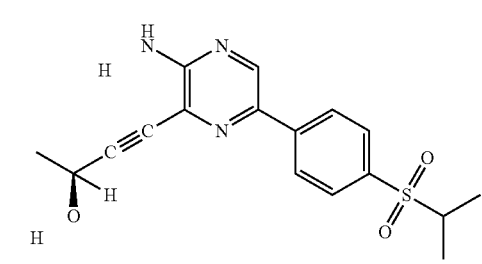
I-30 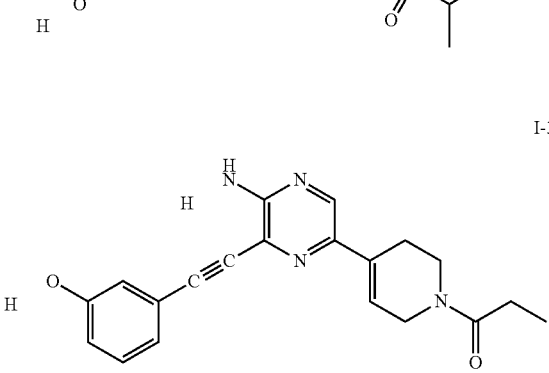
I-31 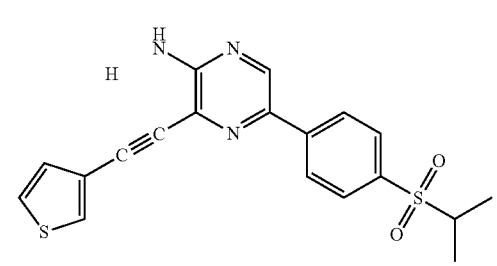
I-32 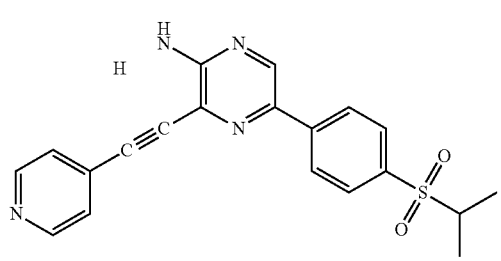
I-33 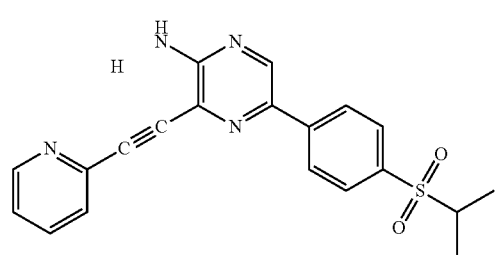
I-34 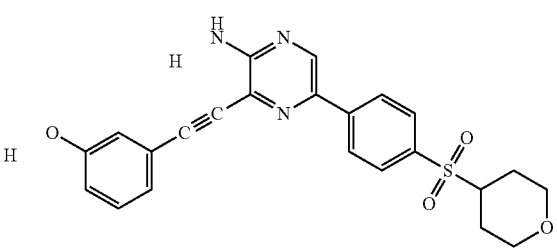
I-35 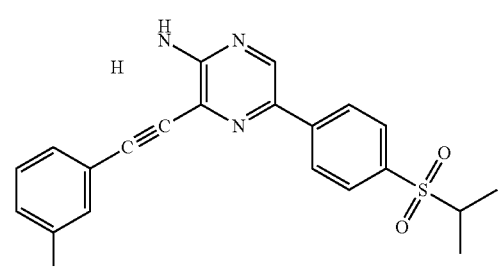
I-36 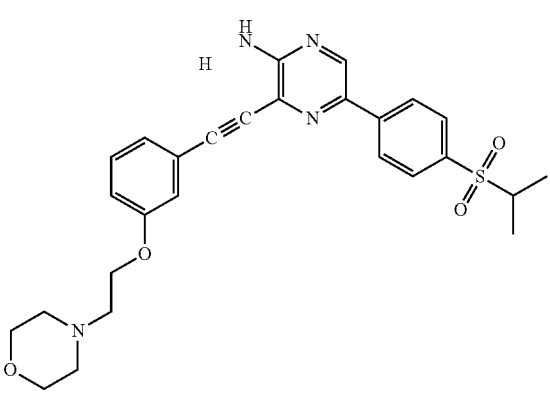

I-37 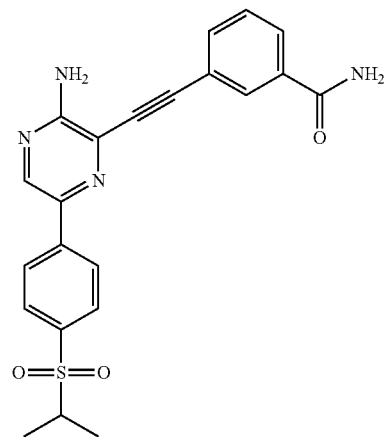
I-38 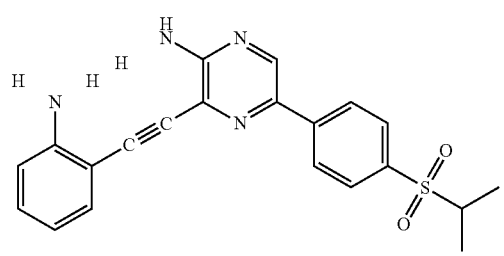
I-39 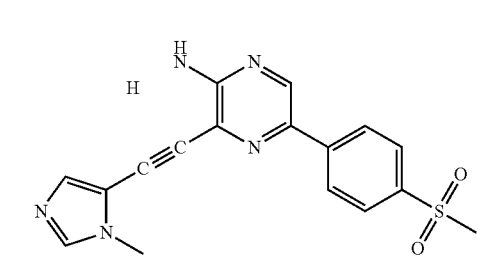
I-40 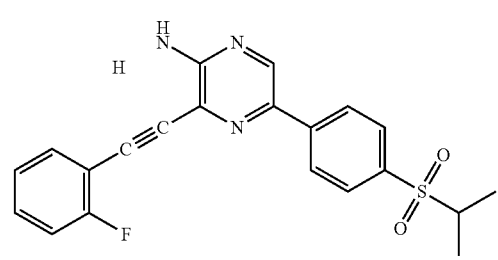
I-41 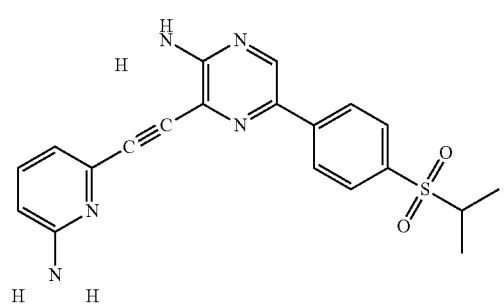
I-42 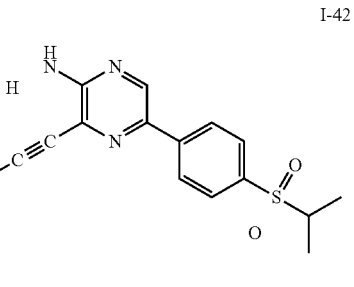
I-43 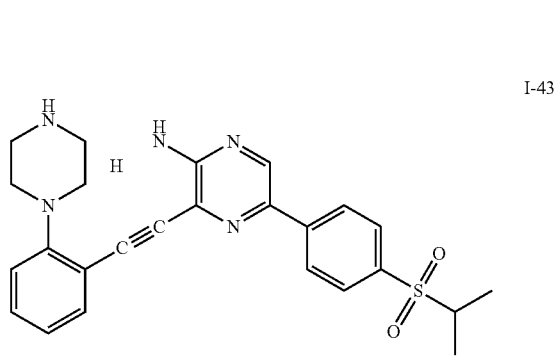
I-44 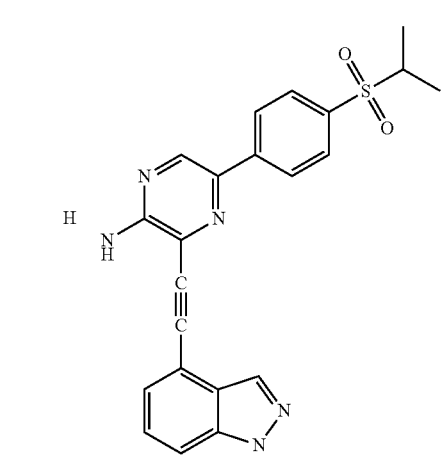
I-45 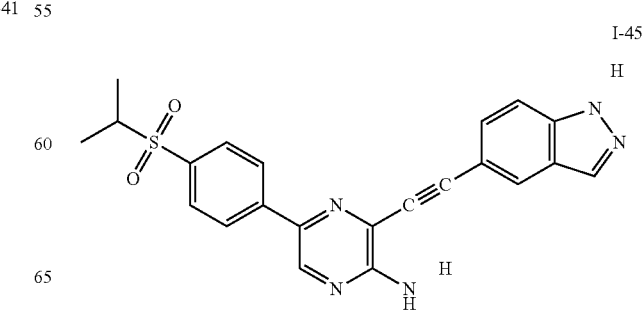

I-46
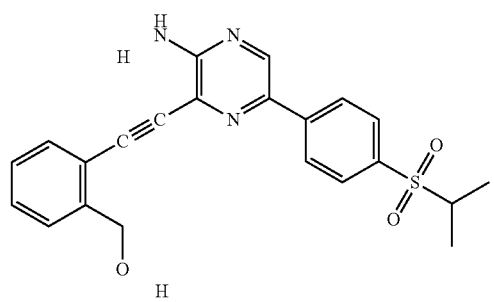
I-48
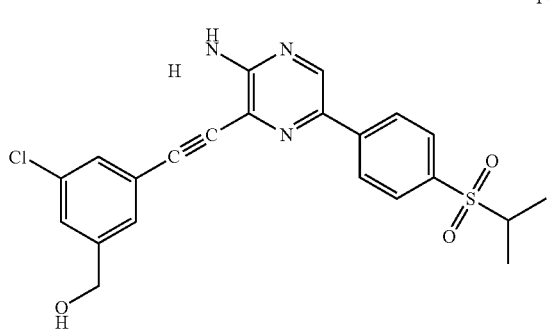
I-47
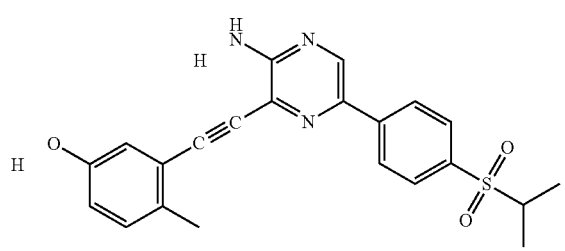
I-49
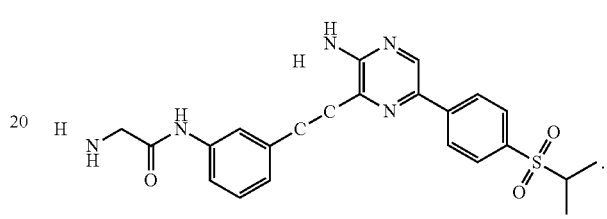
37. A pharmaceutical composition comprising a compound of claim 1 and a pharmaceutically acceptable carrier.
* * * * *

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ser Glu Leu Pro Ala Ser Gln Pro Gln Pro Phe Ser Ala Lys Lys
1               5                   10                  15

Lys